US008852867B2

(12) United States Patent
Kurn et al.

(10) Patent No.: US 8,852,867 B2
(45) Date of Patent: *Oct. 7, 2014

(54) NUCLEIC ACID AMPLIFICATION PROCEDURE USING RNA AND DNA COMPOSITE PRIMERS

(75) Inventors: Nurith Kurn, Palo Alto, CA (US); Shenglong Wang, San Ramon, CA (US)

(73) Assignee: Nugen Technologies, Inc., San Carlos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/103,865

(22) Filed: May 9, 2011

(65) Prior Publication Data

US 2012/0045797 A1    Feb. 23, 2012

Related U.S. Application Data

(63) Continuation of application No. 12/091,843, filed as application No. PCT/US2006/035154 on Sep. 7, 2006, now Pat. No. 7,939,258.

(60) Provisional application No. 60/714,966, filed on Sep. 7, 2005.

(51) Int. Cl.
C12Q 1/68         (2006.01)
C12P 19/34        (2006.01)

(52) U.S. Cl.
CPC .................................. *C12Q 1/6865* (2013.01)
USPC ........................................ 435/6.12; 435/91.2

(58) Field of Classification Search
USPC ................................................ 435/6.12, 91.2
See application file for complete search history.

(56) References Cited

U.S. PATENT DOCUMENTS

| | | |
|---|---|---|
| 3,996,345 A | 12/1976 | Ullman et al. |
| 3,999,345 A | 12/1976 | McKelvey |
| 4,174,384 A | 11/1979 | Ullman et al. |
| 4,261,968 A | 4/1981 | Ullman et al. |
| 4,362,867 A | 12/1982 | Paddock |
| 4,458,066 A | 7/1984 | Caruthers et al. |
| 4,582,788 A | 4/1986 | Erlich |
| 4,683,194 A | 7/1987 | Saiki et al. |
| 4,786,600 A | 11/1988 | Kramer et al. |
| 4,876,187 A | 10/1989 | Duck et al. |
| 4,908,385 A | 3/1990 | Bar-Tana et al. |
| 4,996,143 A | 2/1991 | Heller et al. |
| 5,011,769 A | 4/1991 | Duck et al. |
| 5,043,272 A | 8/1991 | Hartley |
| 5,090,591 A | 2/1992 | Long |
| 5,106,727 A | 4/1992 | Hartley et al. |
| 5,130,238 A | 7/1992 | Malek et al. |
| 5,169,766 A | 12/1992 | Schuster et al. |
| 5,175,243 A | 12/1992 | Ash |
| 5,185,243 A | 2/1993 | Ullman et al. |
| 5,194,370 A | 3/1993 | Berninger et al. |
| 5,262,311 A | 11/1993 | Pardee et al. |
| 5,270,184 A | 12/1993 | Walker et al. |
| 5,328,985 A | 7/1994 | Sano et al. |
| 5,340,716 A | 8/1994 | Ullman et al. |
| 5,399,491 A | 3/1995 | Kacian et al. |
| 5,403,711 A | 4/1995 | Walder et al. |
| 5,409,818 A | 4/1995 | Davey et al. |
| 5,427,911 A | 6/1995 | Ruano |
| 5,427,929 A | 6/1995 | Richards et al. |
| 5,427,930 A | 6/1995 | Birkenmeyer et al. |
| 5,437,990 A | 8/1995 | Burg et al. |
| 5,455,166 A | 10/1995 | Walker |
| 5,480,784 A | 1/1996 | Kacian et al. |
| 5,491,063 A | 2/1996 | Fisher et al. |
| 5,508,178 A | 4/1996 | Rose et al. |
| 5,510,270 A | 4/1996 | Fodor et al. |
| 5,545,522 A | 8/1996 | Van Gelder et al. |
| 5,554,516 A | 9/1996 | Kacian et al. |
| 5,554,517 A | 9/1996 | Davey et al. |
| 5,556,752 A | 9/1996 | Lockhart et al. |
| 5,556,771 A | 9/1996 | Shen et al. |
| 5,565,322 A | 10/1996 | Heller |
| 5,571,669 A | 11/1996 | Lu et al. |
| 5,578,832 A | 11/1996 | Trulson et al. |
| 5,589,339 A | 12/1996 | Hampson et al. |
| 5,595,891 A | 1/1997 | Rose et al. |

(Continued)

FOREIGN PATENT DOCUMENTS

| | | |
|---|---|---|
| EP | 0050424 A1 | 4/1982 |
| EP | 0084796 B1 | 8/1983 |

(Continued)

OTHER PUBLICATIONS

Miyachi et al., Application of chimeric RNA—DNA oligonucleotides to the detection of pathogenic microorganisms using surface plasmon resonance, Analytica Chimica Acta 407 (2000) 1-10.*
U.S. Appl. No. 13/349,927, filed Jan. 13, 2012, Kurn et al.
Office action dated Jan. 19, 2012 for U.S. Appl. No. 12/792,702.
Office action dated Jan. 19, 2012 for U.S. Appl. No. 13/211,996.
U.S. Appl. No. 13/206,309, filed Aug. 9, 2011, Kurn.
European search report and search opinion dated Jul. 1, 2011 for Application No. 9711405.2.
Japanese Office Action for Japanese Patent Application No. 2006-513320 dated Jul. 22, 2010 (English Translation of Japanese Office Action).
Office action dated Aug. 2, 2011 for U.S. Appl. No. 12/792,702.
U.S. Appl. No. 13/282,732, filed Oct. 27, 2011, Kurn.

(Continued)

*Primary Examiner* — Kenneth R. Horlick
*Assistant Examiner* — Joyce Tung
(74) *Attorney, Agent, or Firm* — Wilson Sonsini Goodrich & Rosati

(57) ABSTRACT

The invention provides methods for amplification of polynucleotide sequences using primers containing single-stranded RNA. The methods employ use of an enzyme capable of cleaving single-stranded RNA, such as RNase I, to degrade a first RNA-containing primer prior to addition of a second RNA-containing primer. The invention also provides compositions and kits for practicing the amplification methods, as well as methods which use the amplification products.

10 Claims, 11 Drawing Sheets

(56) References Cited

U.S. PATENT DOCUMENTS

| | | |
|---|---|---|
| 5,616,478 A | 4/1997 | Chetverin et al. |
| 5,627,275 A | 5/1997 | Roll |
| 5,641,658 A | 6/1997 | Adams et al. |
| 5,648,211 A | 7/1997 | Fraiser et al. |
| 5,654,142 A | 8/1997 | Kievits et al. |
| 5,660,988 A | 8/1997 | Duck et al. |
| 5,665,539 A | 9/1997 | Sano et al. |
| 5,665,545 A | 9/1997 | Malek et al. |
| 5,665,845 A | 9/1997 | Allman |
| 5,679,512 A | 10/1997 | Laney et al. |
| 5,679,524 A | 10/1997 | Nikiforov et al. |
| 5,683,879 A | 11/1997 | Laney et al. |
| 5,686,272 A | 11/1997 | Marshall et al. |
| 5,688,648 A | 11/1997 | Mathies et al. |
| 5,693,502 A | 12/1997 | Gold et al. |
| 5,700,642 A | 12/1997 | Monforte et al. |
| 5,708,154 A | 1/1998 | Smith et al. |
| 5,709,994 A | 1/1998 | Pease et al. |
| 5,710,028 A | 1/1998 | Eyal et al. |
| 5,712,124 A | 1/1998 | Walker |
| 5,712,127 A | 1/1998 | Malek et al. |
| 5,714,320 A | 2/1998 | Kool |
| 5,716,785 A | 2/1998 | Van Gelder et al. |
| 5,731,146 A | 3/1998 | Duck et al. |
| 5,731,171 A | 3/1998 | Bohlander |
| 5,744,308 A | 4/1998 | Guillou-Bonnici et al. |
| 5,744,312 A | 4/1998 | Mamone et al. |
| 5,747,255 A | 5/1998 | Brenner |
| 5,763,178 A | 6/1998 | Chirikjian et al. |
| 5,766,846 A | 6/1998 | Schlossmacher et al. |
| 5,766,849 A | 6/1998 | McDonough et al. |
| 5,773,601 A | 6/1998 | Agrawal |
| 5,811,238 A | 9/1998 | Stemmer et al. |
| 5,824,517 A | 10/1998 | Cleuziat et al. |
| 5,824,518 A | 10/1998 | Kacian et al. |
| 5,829,547 A | 11/1998 | Fujii et al. |
| 5,830,655 A | 11/1998 | Monforte et al. |
| 5,830,721 A | 11/1998 | Stemmer et al. |
| 5,837,832 A | 11/1998 | Chee et al. |
| 5,846,710 A | 12/1998 | Bajaj |
| 5,849,478 A | 12/1998 | Cashman |
| 5,849,542 A | 12/1998 | Reeve et al. |
| 5,849,547 A | 12/1998 | Cleuziat et al. |
| 5,854,033 A | 12/1998 | Lizardi et al. |
| 5,858,665 A | 1/1999 | Hepp et al. |
| 5,871,697 A | 2/1999 | Rothberg et al. |
| 5,876,976 A | 3/1999 | Richards et al. |
| 5,882,867 A | 3/1999 | Ullman et al. |
| 5,888,779 A | 3/1999 | Kacian et al. |
| 5,888,819 A | 3/1999 | Goelet et al. |
| 5,916,777 A | 6/1999 | Kacian et al. |
| 5,925,517 A | 7/1999 | Tyagi et al. |
| 5,932,449 A | 8/1999 | Emanuel et al. |
| 5,932,450 A | 8/1999 | Dattagupta et al. |
| 5,932,451 A | 8/1999 | Wang et al. |
| 5,958,681 A | 9/1999 | Wetmur et al. |
| 5,962,271 A | 10/1999 | Chenchik et al. |
| 5,962,272 A | 10/1999 | Chenchik et al. |
| 5,965,409 A | 10/1999 | Pardee et al. |
| 5,985,548 A | 11/1999 | Collier et al. |
| 6,004,744 A | 12/1999 | Goelet et al. |
| 6,004,745 A | 12/1999 | Arnold, Jr. et al. |
| 6,013,431 A | 1/2000 | Soderlund et al. |
| 6,027,889 A | 2/2000 | Barany et al. |
| 6,027,923 A | 2/2000 | Wallace |
| 6,030,774 A | 2/2000 | Laney et al. |
| 6,037,152 A | 3/2000 | Richards et al. |
| 6,040,138 A | 3/2000 | Lockhart et al. |
| 6,060,288 A | 5/2000 | Adams et al. |
| 6,083,689 A | 7/2000 | Martinelli et al. |
| 6,087,103 A | 7/2000 | Burmer |
| 6,090,591 A | 7/2000 | Burg et al. |
| 6,096,715 A | 8/2000 | Rossi et al. |
| 6,107,032 A | 8/2000 | Kilger et al. |
| 6,107,061 A | 8/2000 | Johnson |
| 6,124,120 A | 9/2000 | Lizardi |
| 6,132,997 A | 10/2000 | Shannon |
| 6,136,533 A | 10/2000 | Bekkaoui et al. |
| 6,140,086 A | 10/2000 | Fox et al. |
| 6,143,495 A | 11/2000 | Lizardi et al. |
| 6,159,685 A | 12/2000 | Pinkel et al. |
| 6,183,960 B1 | 2/2001 | Lizardi |
| 6,210,884 B1 | 4/2001 | Lizardi |
| 6,218,105 B1 | 4/2001 | Hall et al. |
| 6,218,151 B1 | 4/2001 | Cleuziat et al. |
| 6,251,600 B1 | 6/2001 | Winger et al. |
| 6,251,639 B1 | 6/2001 | Kurn |
| 6,255,060 B1 | 7/2001 | Eberwine et al. |
| 6,270,961 B1 | 8/2001 | Drmanac |
| 6,271,002 B1 | 8/2001 | Linsley et al. |
| 6,280,935 B1 | 8/2001 | Macevicz |
| 6,280,949 B1 | 8/2001 | Lizardi |
| 6,291,166 B1 | 9/2001 | Gerdes et al. |
| 6,291,170 B1 | 9/2001 | Van Gelder et al. |
| 6,300,073 B1 | 10/2001 | Zhao et al. |
| 6,306,365 B1 | 10/2001 | Ruoslahti et al. |
| 6,309,842 B1 | 10/2001 | Dower et al. |
| 6,309,843 B1 | 10/2001 | Timms |
| 6,316,229 B1 | 11/2001 | Lizardi et al. |
| 6,319,714 B1 | 11/2001 | Crameri et al. |
| 6,326,142 B1 | 12/2001 | Royer |
| 6,335,160 B1 | 1/2002 | Patten et al. |
| 6,344,356 B1 | 2/2002 | Stemmer |
| 6,358,712 B1 | 3/2002 | Jarrell et al. |
| 6,365,375 B1 | 4/2002 | Dietmaier et al. |
| 6,376,191 B1 | 4/2002 | Yu et al. |
| 6,410,278 B1 | 6/2002 | Notomi et al. |
| 6,485,944 B1 | 11/2002 | Church et al. |
| 6,617,137 B2 | 9/2003 | Dean et al. |
| 6,642,034 B2 | 11/2003 | Lizardi |
| 6,673,549 B1 | 1/2004 | Furness et al. |
| 6,686,156 B2 | 2/2004 | Kurn |
| 6,692,918 B2 | 2/2004 | Kurn |
| 6,794,138 B1 | 9/2004 | Cao et al. |
| 6,815,164 B2 | 11/2004 | Kurn |
| 6,858,413 B2 | 2/2005 | Kurn |
| 6,927,024 B2 | 8/2005 | Dodge et al. |
| 6,946,251 B2 | 9/2005 | Kurn |
| 6,949,633 B1 | 9/2005 | Monforte et al. |
| 6,951,722 B2 | 10/2005 | Mukai et al. |
| 7,056,671 B2 | 6/2006 | Enoki et al. |
| 7,094,536 B2 | 8/2006 | Kurn |
| 7,176,025 B2 * | 2/2007 | Kurn et al. ............ 435/440 |
| 7,294,461 B2 | 11/2007 | Kurn |
| 7,351,557 B2 | 4/2008 | Kurn |
| 7,354,717 B2 | 4/2008 | Kurn |
| 7,402,386 B2 | 7/2008 | Kurn et al. |
| 7,534,569 B2 | 5/2009 | Chang et al. |
| 7,824,890 B2 | 11/2010 | Hoser et al. |
| 7,833,716 B2 | 11/2010 | Becker et al. |
| 7,846,666 B2 | 12/2010 | Kurn |
| 7,939,258 B2 * | 5/2011 | Kurn et al. ............ 435/6.12 |
| 8,034,568 B2 | 10/2011 | Kurn et al. |
| 8,071,311 B2 | 12/2011 | Kurn et al. |
| 8,334,116 B2 | 12/2012 | Kurn |
| 8,465,950 B2 | 6/2013 | Kurn et al. |
| 8,492,095 B2 | 7/2013 | Kurn |
| 8,512,956 B2 | 8/2013 | Kurn |
| 2001/0000077 A1 | 3/2001 | Engelhardt et al. |
| 2001/0034048 A1 | 10/2001 | Kurn |
| 2001/0041334 A1 | 11/2001 | Rashtchian et al. |
| 2002/0028447 A1 | 3/2002 | Li et al. |
| 2002/0058270 A1 | 5/2002 | Kurn |
| 2002/0064837 A1 | 5/2002 | Trinh et al. |
| 2002/0106666 A1 * | 8/2002 | Hayashizaki ............ 435/6 |
| 2002/0115088 A1 | 8/2002 | Kurn |
| 2002/0127575 A1 | 9/2002 | Hoke et al. |
| 2002/0142309 A1 | 10/2002 | Dattagupta |
| 2002/0164628 A1 | 11/2002 | Kurn |
| 2002/0177141 A1 | 11/2002 | Chee et al. |
| 2003/0017591 A1 | 1/2003 | Kurn |
| 2003/0049657 A1 | 3/2003 | Cherry |
| 2003/0073081 A1 | 4/2003 | Mukai et al. |
| 2003/0087251 A1 | 5/2003 | Kurn |

(56) References Cited

U.S. PATENT DOCUMENTS

| | | | |
|---|---|---|---|
| 2003/0104460 A1 | 6/2003 | Rabbani et al. |
| 2003/0186234 A1 | 10/2003 | Kurn |
| 2003/0204331 A1 | 10/2003 | Whitney et al. |
| 2003/0215926 A1* | 11/2003 | Kurn et al. .................. 435/91.2 |
| 2004/0005614 A1 | 1/2004 | Kurn et al. |
| 2004/0023271 A1 | 2/2004 | Kurn et al. |
| 2004/0033499 A1 | 2/2004 | Ilsley |
| 2004/0096853 A1 | 5/2004 | Mayer |
| 2004/0203019 A1 | 10/2004 | Kurn et al. |
| 2004/0203025 A1 | 10/2004 | Kurn |
| 2005/0003441 A1 | 1/2005 | Kurn |
| 2005/0014192 A1 | 1/2005 | Kurn |
| 2005/0019793 A1 | 1/2005 | Kurn et al. |
| 2005/0037351 A1 | 2/2005 | Kanno et al. |
| 2005/0064456 A1 | 3/2005 | Kurn |
| 2005/0079510 A1 | 4/2005 | Berka et al. |
| 2005/0123950 A1 | 6/2005 | Mukai et al. |
| 2005/0130173 A1 | 6/2005 | Leamon et al. |
| 2005/0208538 A1 | 9/2005 | Kurn et al. |
| 2006/0008824 A1 | 1/2006 | Ronaghi et al. |
| 2006/0014182 A1 | 1/2006 | Kurn |
| 2006/0183132 A1 | 8/2006 | Fu et al. |
| 2006/0246434 A1 | 11/2006 | Erlander et al. |
| 2006/0257879 A1 | 11/2006 | Wilson et al. |
| 2006/0269934 A1 | 11/2006 | Woudenberg et al. |
| 2007/0054301 A1 | 3/2007 | Becker et al. |
| 2008/0176311 A1 | 7/2008 | Kurn |
| 2008/0182300 A1 | 7/2008 | Kurn |
| 2009/0036663 A1 | 2/2009 | Kurn |
| 2009/0068709 A1 | 3/2009 | Kurn et al. |
| 2009/0130721 A1 | 5/2009 | Kurn et al. |
| 2009/0203085 A1 | 8/2009 | Kurn et al. |
| 2009/0203531 A1 | 8/2009 | Kurn et al. |
| 2009/0233804 A1 | 9/2009 | Kurn et al. |
| 2009/0239232 A1 | 9/2009 | Kurn et al. |
| 2009/0275486 A1 | 11/2009 | Kurn et al. |
| 2010/0022403 A1 | 1/2010 | Kurn et al. |
| 2010/0159559 A1 | 6/2010 | Kurn et al. |
| 2010/0167354 A1 | 7/2010 | Kurn et al. |
| 2010/0311066 A1 | 12/2010 | Kurn |
| 2011/0105364 A1 | 5/2011 | Kurn |
| 2011/0189679 A1 | 8/2011 | Kurn et al. |
| 2011/0224105 A1 | 9/2011 | Kurn et al. |
| 2011/0294132 A1 | 12/2011 | Kurn |
| 2012/0190587 A1 | 7/2012 | Kurn et al. |
| 2013/0231253 A1 | 9/2013 | Amorese et al. |
| 2014/0038188 A1 | 2/2014 | Kurn |
| 2014/0038236 A1 | 2/2014 | Kurn et al. |

FOREIGN PATENT DOCUMENTS

| | | | |
|---|---|---|---|
| EP | 0201184 B1 | 11/1986 |
| EP | 0237362 B1 | 9/1987 |
| EP | 0258017 B1 | 3/1988 |
| EP | 0320308 B1 | 6/1989 |
| EP | 0365627 B1 | 5/1990 |
| EP | 0395398 A2 | 10/1990 |
| EP | 0395398 A3 | 10/1990 |
| EP | 0497272 B1 | 8/1992 |
| EP | 0500224 A2 | 8/1992 |
| EP | 0505012 B1 | 9/1992 |
| EP | 0543612 B1 | 5/1993 |
| EP | 0329822 B1 | 6/1994 |
| EP | 0667393 A2 | 8/1995 |
| EP | 0667393 A3 | 8/1995 |
| EP | 0497271 B1 | 10/1996 |
| EP | 0878553 B1 | 11/1998 |
| EP | 0971039 A2 | 1/2000 |
| EP | 0971039 A3 | 1/2000 |
| EP | 1055736 A1 | 11/2000 |
| EP | 1167524 A1 | 1/2002 |
| EP | 1273737 A2 | 1/2003 |
| EP | 1275737 A2 | 1/2003 |
| EP | 1281757 A1 | 2/2003 |
| EP | 1312682 A1 | 5/2003 |
| JP | 6327500 A | 11/1994 |
| JP | 7023799 A | 1/1995 |
| WF | WO 97/32040 A3 | 10/1997 |
| WO | WO 88/02746 A1 | 4/1988 |
| WO | WO 88/10315 A1 | 12/1988 |
| WO | WO 89/01050 A1 | 2/1989 |
| WO | WO 89/06700 A1 | 7/1989 |
| WO | WO 90/01069 | 2/1990 |
| WO | WO 92/15712 | 9/1992 |
| WO | WO 92/18521 A1 | 10/1992 |
| WO | WO 93/15229 A2 | 8/1993 |
| WO | WO 95/03426 A2 | 2/1995 |
| WO | WO 93/15229 A3 | 3/1995 |
| WO | WO 95/21271 A1 | 8/1995 |
| WO | WO 97/03207 A1 | 1/1997 |
| WO | WO 97/04123 A1 | 2/1997 |
| WO | WO 97/04126 A1 | 2/1997 |
| WO | WO 97/32040 A2 | 9/1997 |
| WO | WO 98/01050 A1 | 1/1998 |
| WO | WO 98/06736 A1 | 2/1998 |
| WO | WO 98/28443 A1 | 7/1998 |
| WO | WO 98/44151 A1 | 10/1998 |
| WO | WO 98/59066 A1 | 12/1998 |
| WO | WO 99/18241 A1 | 4/1999 |
| WO | WO 99/23256 A1 | 5/1999 |
| WO | WO 99/25873 A1 | 5/1999 |
| WO | WO 99/29901 A1 | 6/1999 |
| WO | WO 99/37808 A1 | 7/1999 |
| WO | WO 99/40219 A1 | 8/1999 |
| WO | WO 99/42618 A1 | 8/1999 |
| WO | WO 99/55912 A1 | 11/1999 |
| WO | WO 00/08208 A2 | 2/2000 |
| WO | WO 00/09745 A1 | 2/2000 |
| WO | WO 00/08208 A3 | 5/2000 |
| WO | WO 00/28082 A1 | 5/2000 |
| WO | WO 00/40715 A2 | 7/2000 |
| WO | WO 00/52191 A1 | 9/2000 |
| WO | WO 00/56877 A1 | 9/2000 |
| WO | WO 00/56925 A2 | 9/2000 |
| WO | WO 00/56925 A3 | 9/2000 |
| WO | WO 00/70095 A2 | 11/2000 |
| WO | WO 01/20035 A2 | 3/2001 |
| WO | WO 01/20035 A3 | 3/2001 |
| WO | WO 01/23613 A1 | 4/2001 |
| WO | WO 00/70095 A3 | 8/2001 |
| WO | WO 01/64952 A2 | 9/2001 |
| WO | WO 01/73134 A2 | 10/2001 |
| WO | WO 02/00938 A2 | 1/2002 |
| WO | WO 02/06533 A2 | 1/2002 |
| WO | WO 02/28876 A2 | 4/2002 |
| WO | WO 02/29117 A2 | 4/2002 |
| WO | WO 02/048402 A2 | 6/2002 |
| WO | WO 02/057487 A2 | 7/2002 |
| WO | WO 02/057487 A3 | 7/2002 |
| WO | WO 02/028876 A3 | 8/2002 |
| WO | WO 02/072772 A2 | 9/2002 |
| WO | WO 02/072773 A2 | 9/2002 |
| WO | WO 01/64952 A3 | 12/2002 |
| WO | WO 02/103013 A2 | 12/2002 |
| WO | WO 01/73134 A3 | 1/2003 |
| WO | WO 03/012100 A2 | 2/2003 |
| WO | WO 03/012100 A3 | 2/2003 |
| WO | WO 03/012142 A1 | 2/2003 |
| WO | WO 02/103013 A3 | 3/2003 |
| WO | WO 02/06533 A3 | 4/2003 |
| WO | WO 02/000938 A3 | 8/2003 |
| WO | WO 02/029117 A3 | 8/2003 |
| WO | WO 02/072772 A3 | 9/2003 |
| WO | WO 03/078645 A2 | 9/2003 |
| WO | WO 03/078645 A3 | 9/2003 |
| WO | WO 03/083435 A2 | 10/2003 |
| WO | WO 03/083435 A3 | 10/2003 |
| WO | WO 2004/011665 A2 | 2/2004 |
| WO | WO 02/48402 A3 | 4/2004 |
| WO | WO 2004/069849 A2 | 8/2004 |
| WO | WO 2004/092418 A2 | 10/2004 |
| WO | WO 2004/092418 A3 | 12/2004 |
| WO | WO 2004/069849 A3 | 3/2005 |

(56) References Cited

FOREIGN PATENT DOCUMENTS

| WO | WO 2004/011665 A3 | 7/2005 |
|---|---|---|
| WO | WO 2005/065321 A2 | 7/2005 |
| WO | WO 2006/138257 A2 | 12/2006 |
| WO | WO 2007/030759 A2 | 3/2007 |
| WO | WO 2004/069849 A3 | 4/2007 |
| WO | WO 2007/041201 A2 | 4/2007 |
| WO | WO 2007/030759 A3 | 6/2007 |
| WO | WO 2007/041201 A3 | 11/2007 |
| WO | WO 2007/136717 A1 | 11/2007 |
| WO | WO 2008/005459 A2 | 1/2008 |
| WO | WO 2008/05459 A3 | 2/2008 |
| WO | WO 2006/138257 A3 | 12/2008 |
| WO | WO 2012/103154 A1 | 8/2012 |
| WO | PCT/US2013/032606 | 3/2013 |
| WO | WO 2013/059746 A1 | 4/2013 |

OTHER PUBLICATIONS

Notice of allowance dated Sep. 2, 2011 for U.S. Appl. No. 12/615,958.
Office action dated Apr. 6, 2012 for U.S. Appl. No. 13/282,732.
Office action dated May 1, 2012 for U.S. Appl. No. 13/349,927.
Office action dated May 7, 2012 for U.S. Appl. No. 13/206,309.
Office action dated Jul. 23, 2012 for U.S. Appl. No. 13/211,996.
Claims filed Jun. 27, 2012 for U.S. Appl. No. 12/792,702.
Claims filed Jul. 9, 2012 for U.S. Appl. No. 13/282,732.
Claims filed Aug. 1, 2012 for U.S. Appl. No. 13/349,927.
Office action dated Sep. 14, 2012 for U.S. Appl. No. 13/282,732.
Office action dated Nov. 2, 2012 for U.S. Appl. No. 13/206,309.
U.S. Appl. No. 60/255,638, filed Dec. 13, 2000, Kurn.
U.S. Appl. No. 60/381,457, filed May 17, 2002, Kurn.
U.S. Appl. No. 60/533,381, flied Dec. 29, 2003, Kurn et al.
U.S. Appl. No. 13/918,636, filed Jun. 14, 2013, Kurn et al.
U.S. Appl. No. 13/922,146, filed Jun. 19, 2013, Kurn.
U.S. Appl. No. 13/938,059, filed Jul. 9, 2013, Schroeder et al.
U.S. Appl. No. 13/939,025, filed Jul. 10, 2013, Kurn et al.
U.S. Appl. No. 14/030,761, filed Sep. 18, 2013, Kurn et al.
Abravaya et al. Detection of point mutations with modified ligase chain reaction (Gap-LCR). Nucleic Aids Research. 1995;23(4):675-682.
Adessi et al. Solid Phase DNA amplification: characterisation of primer attachment and amplification mechanisms Nucleic Acids Research. 2000;28(20):E87.
Agrawal et al. Site Specific Functionalization of Oligonucleotides for Attaching Two Different Reporter Groups. Nucleic Acids Research. 1990;18(18):5419-5423.
Akhras et al. Connection inversion probe technology: a powerful one-printer multiplex DNA amplification system for numerous scientific mapplications. PLoS ONE 2007;2(9):e915.
Andras, et al. Strategies for signal amplification in nucleic acid detection. Mol Biotechnol. Sep. 2001; 19(1):29-44.
Arashi-Heese et al. XcmI site-containing vector for direct cloning and in vitro transcription of PCR product. Molecular Biotechnology, 1999:12(3):281-3.
Ausubel et al. (eds.) Current Protocols in Molecular Biology. John Wiley & Sons, Inc.; 1995:iii-xii (Table of Contents Only.).
Baner et al. Parallel gene analysis with allele-specific padlock probes and tag microarrays. Nucleic Acids Research. 2003;31(17):e103.
Barbas III et al. In Vitro Evolution of a Neutralizing Human Antibody to Human Immunodeficiency Virus Type I to Enhance Affinity and Broaden Strain Cross-Reactivity. Proc. Natl. Acad. Sci. USA. 1994;91:3809-3813.
Barker et al. Increased DNA microarray hybridization specificity using sscDNA targets. BMC Genomics. 2000:6(1):57.
Barth et al. Combining Phage Display and Screening of cDNA Expression Libraries: A New Approach for Identifying the Target Antigen of an scFv Preselected by Phase Display. Journal of Molecular Biology. 2000;301:751-757.
Beaucage et al. Deoxynucleoside Phosphoramidites—A New Class of Key Intermediates for Deoxypolynucleotide Synthesis. Teterahedron Letters. 1981;22(20):1859-1862.
Beggs, et al. Characterization of *Mycobacterium tuberculosis* complex direct repeat sequence for us in cycling probe reaction. J Clin Microbiol. Dec. 1996;34(12):2985-9.
Bekkaoui et al. Rapid detection of the mecA gene in methicillin resistant *Staphylococci* using a colorimetric cycling probe technology. Diagnostic Microbiology and Infectious Disease. 1999;34(2):83-90.
Ben-Artzi, et al. Double-stranded RNA -dependent RNase activity associated with human immunodeficiency virus type 1 reverse transcriptase. Proc Natl Acad Sci U S A. Feb. 1, 1992;89(3):927-31.
Bing, et al. Bridge Amplification: A Solid Phase PCR System for the Amplification and Detection of Allelic Differences in Single Copy Genes. Genetic Identity Conference Proceedings. 1996, Available at http://www.promega.com/geneticidproc/ussymp7proc/0726.html. Accessed Dec. 22, 2009.
Blanchard et al. High-density oligonucleotide arrays. Biosensors & Bioelectronics. 1996;11(6/7):687-690.
Brenner et al. Gene expression analysis by massively parallel signature sequencing (MPSS) on microbead arrays. Nature Biotechnology. 2000;18(6):630-634.
Brown et al. Chemical Synthesis and Cloning of a Tyrosine tRNA Gene. Methods In Enzymology. 1979;68:109-151.
Brown., T.A. Ed. Molecular Biology, LabFax. Bios Scientific Publishers. Academic Press. 1991; pp. 147-148.
Caruthers et al. Chemical synthesis of deoxyoligonucleotides by the phosphoramidite method. Methods In Enzymology. 1987;154:287-313.
Chetverin et al. On the nature of spontaneous RNA synthesis by Q beta replicase. Journal of Molecular Biology. 1991;222(1):3-9.
Church, Genomes for ALL. Scientific American. 2006;294(1):46-54.
Coco et al. DNA Shuffling Method for Generating Highly Recombined Genes and Evolved Enzymes. Nature Biotechnology. 2001;19:354-359.
Cohen et al. Construction of biologically functional bacterial plasmids in vitro. Pro. Natl. Acad. Sci. USA. 1973;70(11):3240-4.
Coljee et al. Seamless Gene Engineering Using RNA- and DNA-Overhang Cloning. Nature Biotechnology. 2000;18:789-791.
Crameri et al. Molecular Evolution of an Arsenate Detoxification Pathway by DNA Shuffling. Nature Biotechnology. 1997;15:436-438.
Dafforn et al. Linear mRNA amplification from as little as 5 ng total RNA for global gene expression analysis. Biotechniques. 2004;37(5)854-857.
Dahl et al. Multigene amplification and massively parallel sequencing for cancer mutation discovery. Proc. Natl. Acad. Sci. USA. 2007;104(22):9387-9392.
Daigo et al. Degenerate Oligonucleotide Primed-Polymerase Chain Reaction-Based Array Comparative Genomic Hybridization for Extensive Amplicon profiling of Breast Cancers. American Journal of Pathology. 2001;158(5):1623-1631.
Database WPI, Section Ch, Week 199507, Derwent Publications Ltd., London, GB; Class B04; AN 1995-047919, XP002276586 & JP 06 327500 A (Toyobo KK), Nov. 29, 1994. (Abstract Only). 1 page total.
Dean ete al. Comprehensive Human Genome Amplification Using Multiple Displacement Amplification. Proc. Natl. Acad. Sci. USA. 2002;99(8):5261-5266.
Deiman et al. Characteristics and applications of nucleic acid sequence-base amplification (NASBA). Mol Biotechnol. Feb. 2002;20(2):163-79.
Derisi et al. Use of cDNA microarray to analyse gene expression patterns in human cancer. Nature Genetics. 1996:14:457-460.
Dietmaier et al. Multiple Mutation Analyses in Single Tumor cells with Improved Whole Genome Amplification. American Journal of Pathology. 1999;154(1):83-95.
Dressman et al. Transforming single DNA molecules into fluorescent magnetic particles for detection and enumeration of genetic variations. Proc. Natl. Acad. Sci. USA. 2003;100(15):8817-8822.
European Search Report (Supplementary partial) mailed Dec. 22, 2005 for European Patent Application No. 0273119.0.
European search report dated Mar. 13, 2006 for Application No. 02731119.

(56) References Cited

OTHER PUBLICATIONS

European search report dated Sep. 17, 2009 for Application No. 04002084.4
European search report dated Nov. 11, 2008 for Application No. 3718172.4.
European search report dated Nov. 13, 2006 for Application No. 03717952.
European Search Report mailed on May 13, 2004 for patent application No. 02721342.0-2402.
Fan et al. Highly parallel genomic assays. Nature Reviews Genetics. 2006;7(8):632-644.
Flanagan et al., A Cytosine Analog That Confers Enhances Potency to Antisense Oligonucleotides. Proc. Natl. Acad. Sci. USA. 1999;96(7);3513-3518.
Fodor et al. Light-Directed. Spatially addressable parallel chemical synthesis. Science. 1991;251:767-773.
Freier et al. Improved Free-Energy Parameters for Predictions of RNA Duplex Stability. Proc. Natl. Acad. Sci. USA. 1986;83:9373-9377.
Freshney. Ed. Animal Cell Culture. IRL Press: Oxford: 1987: vii-xii (Table of Contents Only.).
Frohman, M.A. RACE: Rapid amplification of cDNA ends. In: PCR Protocols: A Guide to Methods and Applications. Academic Press, NY, 1990;28-38.
Fu et al. Sequencing Double-Stranded DNA by Strand Displacement. Nucleic Acids Research. 1997;25(3):677-679.
Gait. Oligonucleotide Synthesis: A Practical Approach. ed. IRL Press: Oxford; 1984:vii-xii (Table of Contents).
Gasparini et al. Scanning the First Part of the Neurofibromatosis Type 1 Gene by RNA-SSCP: Identification of Three Novel Mutations and of Two New Polymorphisms. Human Genetics. 1996;97:492-495.
Ghadessy et al. Directed evolution of polymerase function by compartmentalized self-replication. Proc. Natl. Acad. Sci. USA. 2001:98(8):4552-4557.
Go. Protein Structures and Split Genes. Advances in Biophysics. 1985;19:91-131.
Goodchild. Conjugates of Oligonucleotides and Modified Oligonucleotides: A Review of Their Synthesis and Properties. Bioconjugate Chemistry. 1990;1(3):165-187.
Guatelli et al. Isothermal, In Vitro Amplification of Nucleic Acids by a Multienzyme Reaction Modeled After Retroviral Replication. Proc. Natl. Acad. Sci. USA. 1990;87:1874-1878.
Gubler et al. A simple and very efficient method for generating cDNA libraries. Gene. 1983;25:263-269.
Gulick et al. Forced Evolution of Glutathione S-Transferase to Create a More Efficient Drug Detoxication Enzyme. Proc. Natl. Acad. Sci. USA. 1995;92:8140-8144.
Habermann et al. Clostridial Neurotoxins: Handling and Action at the Cellular and Molecular Level. Current Topic in Microbiology and Immunology. 1986;129:93-179.
Hatch, et al. Rolling circle amplification of DNA immobilized on solid surfaces and its application to multiplex mutation detection. Genet Anal. Apr. 1999;15(2)35-40.
Hawkins, et al. Whole genome amplification—applications and advances. Curr Opin Biotechnol. Feb. 2002;13(1):65-7.
Heim et al. Engineering Green Fluorescent Protein for Improved Brightness, Longer Wavelengths and Fluorescence Resonance Energy Transfer. Current Biology. 1996;6:178-182.
Hendrickson et al. High sensitivity Multianalyte immunoassay using covalent DNA-labeled antibodies and polymerase chain reaction. Nucleic Acids Research. 1995;23: 522-529.
Hottiger, et al. Strand displacement activity of the human immunodeficiency virus type 1 reverse transcriptase heterodimer and its individual subunits. J Biol Chem Jan. 14, 1994;269(2):986-91.
Huber, et al. Processing of the primer for plus strand DNA synthesis by human immunodeficiency virus 1 reverse transcriptase. J Biol Chem. Jun. 25, 1990:265(18):10565-73.
Hutchison et al. Cell-free cloning using phi29 DNA polymerase. Proc. Natl. Acad. Sci. USA. 2005;102(48):17332-17336.
Innis et al. PCR Protocols: A Guide to Methods and Applications. Eds. Academic Press. 1990:v-x (Table of Contents).
Inoue, et al. Synthesis and hybridization studies on two complementary nona(2'-O-methyl)ribonucleotides. Nucleic Acids Res. Aug. 11, 1987;15(15):6131-48.
International preliminary report on patentability dated Aug. 26, 2010 for PCT Application No. US2009/33936.
International preliminary report on patentability dated Aug. 26, 2010 for PCT Application No. US2009/033964.
International search report dated Feb. 3, 2003 for PCT Application No. US2001/047775.
International search report dated Mar. 9, 2007 for PCT Application No. US2006/035154.
International search report dated Mar. 18, 2003 for PCT Application No. US2001/020660.
International search report dated Jun. 23, 2003 for PCT Application No. US2002/007306.
International search report dated Jul. 3, 2001 for PCT Application No. US2000/025104.
International search report dated Sep. 28, 2009 for PCT Application No. US2009/033964.
International search report dated Oct. 20, 2009 for PCT Application No. US2009/037870.
International search report dated Nov. 29, 2009 for PCT Application No. US2009/033936.
International Search Report mailed Aug. 8, 2003 for PCT Application No. PCT/US02/007377.
International Search Report mailed on Jan. 8, 2004, for PCT patent application No. PCT/US03/007425 filed on Mar. 11, 2003.
International Search Report mailed on Oct. 15, 2004 for PCT Application No. PCT/US2004/012779 filed on Apr. 14, 2004.
International Search mailed on Oct. 30, 2003, for PCT patent application No. PCT/US03/10148 filed on Mar. 31, 2003.
Joyce. Directed Molecular Evolution. Scientific American. 1992;267(6):90-97.
Kass et al. Inter-alu polymerase chain reaction: advancements and applications. Analytical Biochemistry. 1955;228(2):185-193.
Khrapko et al. A method for DNA sequencing by hybridization with oligonucleotide matrix. DNA Sequence. 1991;1:375-388.
Kikuchi et al. An Effective Family Shuffling Method Using Single-Stranded DNA. Gene. 2000;243:133-137.
Kikuchi et al. Novel Family Shuffling Methods for the in vitro Evolution of Enzymes. Gene. 1999;236:159-167.
Kojima et al. PCR amplification from single DNA molecules on magnetic beads in emulsion: application for high-throughput screening of transcription factor targets. Nucleic Acids Research. 2005;33(17):e150.
Kolkman et al. Directed Evolution of Proteins by Exon Shuffling. Nature Biotechnology. 2001;19:423-428.
Kricka. Nonisotopic DNA Probe Techniques. Academic Press. 1992. (Table of Contents only).
Kumar et al. The First Analogues of LNA (Locked Nucleic Acids): Phosphorothioate LNA and 2'-Thio-LNA. Bioorganic & Medicinal Chemistry Letters. 1998;8:2219-2222.
Kurn et al. Novel isothermal, linear nucleic acid amplification systems for highly multiplexed applications. Clinical Chemistry. 2005:51(10):1973-1981.
Kurtzman et al. Advances in Directed Protein Evolution by Recursive Genetic Recombination: Applications to Therapeutic Proteins. Current Opinion in Biotechnology. 2001;12:361-370.
Kwoh et al. Transcription-Based Amplification System and Detection of Amplified Human Immunodeficiency Virus Type 1 with a Bead-Based Sandwich Hybridization Format. Proc. Natl. Acad. Sci. USA. 1989;86:1173-1177.
Li et al. Amplification and analysis of DNA sequences in single human sperm and diploid cells. Nature. 1988;335(6189):414-417.
Lishanski et al. Branch Migration Inhibition in PCR-Amplified DNA: Homogeneous Mutation Detection. Nucleic Acids Research. 2000;28(9):E42, pp. i-vii.
Lizardi et al. Mutation detection and single-molecule counting using isothermal rolling-circle amplification. Nature Genetics. 1998;19(3):225-232.

(56) References Cited

OTHER PUBLICATIONS

Lockhart et al. Expression Monitoring by hybridization to highly-density oligonucleotide arrays. Nature Biotechnology. 1996;14:1675-1680.
MacMillan et al. Synthesis of Functionally Tethered Oligodeoxynycleotides by the Convertible Nucleoside Approach. The Journal of Organic Chemistry. 1990;55:5931-5933.
Makos et al. Oligonucleotide Hybridisations on Glass Supports: A Novel Linker for Oligonucleotide Synthesis and Hybridisation Properties of Oligonucleotides Synthesised in situ. Nucleic Acids Research. 1992;20(7):1679-1684.
Marcy et al. Nanoliter reactors improve multiple displacement amplification of genomes from single cells. PLoS Genetics 2007;3(9):1702-1708.
Marshall et al. DNA chips: An array of possibilities. Nature Biotehnology, 1998;16:27-31.
Maskos et al. Oligonucleotide hybridisations on glass supports: a novel linker for oligonucleotide synthesis and hybridisation properties of oligonucleotides synthesised in situ. Nucleic Acids Research. 1992;20(7):1679-1684.
Matson et al. Biopolymer synthesis on polypropylene supports: Oligonucleotide arrays. Analytical Biochemistry, 1995;224(1):110-116.
Medical Dictionary, online, definition of RNase I, pp. 1-3, retrieved 2009, from: http://www.mondofacto.com/facts/dictionary?Escherichia+coli+RNase+1.
Mitra et al. In situ localized amplification and contact replication of many individual DNA molecules. Nucleic Acids Research. 1999;27(24):e34.
Mullis et al. PCR: Polymerase Chain Reaction. eds. Birkhauser; Boston: 1994:xv-xvii (Table of Contents).
Mullis et al. Specific Enzymatic Amplification of DNA In Vitro: the Polymerase Chain Reaction. Cold Spring Harbor Symposia on Quantitative Biology, 1986;51:263-273.
Mullis et al. Specific synthesis of DNA in vitro via a polymerase-catalyzed chain reaction. Methods in Enzymology. 1987;155:3365-350.
Nakano et al. Single-molecule PCR using water-in-oil emulsion. Journal of Biotechnology. 2003:102(2):117-24.
Narang et al. Improved Phosphotriester Method for the Synthesis of Gene Fragments. Methods of Enzymology. 1979:68:90-99.
New England Biolab Polymerases Polymerases from NEB. 2008;p. 1-2. Available at http://www.neb.com/nebecomm/tech_reference/polymerases/polymeraes_from_neb.as p. Accessed Jun. 30, 2008.
Nugen, Inc. Ovation Biotin RNA Amplification and Labeling System User Guide, Catalog #2300-12, Published 2004.
Nugen, Inc. Technical Report #1. The Ovation Biotin System Validation for Use with Affymetrix GeneChip Arrays. Published 2004.
Office action dated Feb. 17, 2010 for U.S. Appl. No. 11/933,258.
Office action dated Feb. 17, 2010 for U.S. Appl. No. 11/933,332.
Ohara, et al. One-sided polymerase chain reaction: the amplification of cDNA. Proc Natl Acad Sci U S A. Aug. 1989;86(15):5673-7.
Okayama et al. High Efficiency Cloning of Fall-Length cDNA. Molecular and Cell Biology. 1982;2:161-170.
Orita et al. Detection of Polymorphisms of Human DNA by Gel Electrophoresis as Single-Strand Conformation Polymorphisms. Proc. Natl. Acad. Sci. USA. 1989;86(8)2766-2770.
Orita et al. Rapid and sensitive detection of point mutations and DNA polymorphisms using the polymerase chain reaction. Genomics. 1989;5(4):874-879.
Patel et al. Formation of chimeric DNA primer extension products by template switching onto an annealed downstream oligonucleotide. Proc. Natl. Acad. Sci. USA. 1996;93:2969-2974.
Pease et al. Light-generated oligonucleotide arrays for rapid DNA sequene analysis. Proc. Natl. Acad. Sci. USA Biochemistry. 1994;91:5022-5026.
Pieles et al. Preparation of Novel Psoralen Containing Deoxyadenosine Building Block for the Facile Solid Phase Synthesis of Psoralen-Modified Oligonucleotides for a Sequence Specific Crosslink to a Given Target Sequence. Nucleic Acids Research. 1989;17(22):8967-8978.
Pluckthun et al. In Vitro Selection and Evolution of Proteins. Advances in Protein Chemistry. 2001;55:367-403.
Ramsay, DNA chips: State-of-the art. Nature Biotechnology. 1998;16:40-44.
Roget et al. Synthesis and Use of Labelled Nucleoside Phosphoramidite Building Blocks Bearing a Reporter Group: Biotinyl, Dinitrophenyl, Pyrenyl. Nucleic Acids Research. 1989;17:7643-7651.
Saiki et al. Primer-directed enzymatic amplification of DNA with thermostable DNA polymerase. Science. 1988;239-487-491.
Sambrook et al. (eds). Molecular Cloning—A Laboratory Manual, 1989, Second Edition, Cold Spring Harbor Laboratory Press, Cold Spring Harbor, New York, pp. xi-xxxviii (Table of Contents Only).
Sano et al. Immuno-PCR: very sensitive antigen detection by means of specific antibody-DNA conjugates. Science. 1992;258:120-122.
Sarkar et al. Screening for Mutations by RNA Single-Strand Conformation Polymorphism (rSSCP): Comparison with DNA-SSCP. Nucleic Acids Research. 1992;20(4):871-878.
Sasaki et al. Transcriptional sequencing: A method for DNA sequencing using RNA polymerase. Biochemistry. 1998;95:3455-3460.
Scaringe et al. Novel RNA synthesis method using 5'-0-silyl-2'-0-orthoester protecting groups. Journal of American Chemical Society: 1998;120:11820-11821.
Scaringe. Advanced 5'-Silyl-2'-Orthoester Approach to RNA Oligonucleotide Synthesis. Methods Enzymology. 2000;317:3-18.
Schena et al. Parallel Human Genome Analysis: Microarray-Based Expression Monitoring of 1000 Genes. Proc. Natl. Acad. Sci. USA. 1996;93:10614-10619.
Schena et al. Quantitative monitoring of gene expression patterns with a complementary DNA microarray. Science, 1995:270:467-470.
Schmidt-Dannert. Directed Evolution of Single Proteins, Metabolic Pathways, and Viruses. Biochemistry. 2001;40(44):13125-13136.
Schweitzer et al. Immunoassays with rolling circle DNA amplification: a versatile platform for ultrasensitive antigen detection. Proc. Natl. Acad. Sci. USA. 2000;97(18):10113-10119.
Scott et al. Production of Cyclic Peptides and Proteins in vivo. Proc. Natl. Acad. Sci. USA. 1999;96(24):13638-13643.
Shalon et al. A DNA microarray system for analyzing complex DNA samples using two-color fluorescent probe hybridization. Genome Research. 1996;6:639-645.
Shendure et al. Accurate multiplex polony sequencing of an evolved bacterial genome. Science. 2005;309(5741):1728-32.
Stemmer. DNA Shuffling by Random Fragmentation and Reassembly: In Vitro Recombination for Molecular Evolution. Proc. Natl. Acad. Sci. USA. 1994;91:10747-10751.
Stemmer. Rapid Evolution of a Protein In Vitro by DNA Shuffling. Nature, 1994;370:389-391.
Stoecklein et al. SCOMP is Superior to Degenerated Oliugonucleotide Primed Polymerase Chain Reaction for Global Amplifiation of Minute Amounts of DNA from Microdissected Archival Tissue Samples. American Journal of Pathology. 2002;161(1)43-51.
Stratagene Catalog. 1998; p. 39. Gene Characterization Kits. Table of Contents.
Stump et al. The Use of Modified Primers of Eliminate Cycle Sequencing Artifacts. Nucleic Acids Research. 1999;27(23):4642-4648.
Suzuki, et al. Detection of ras Gene Mutations in Human Lung Cancers by Single Strand Conformation Polymorphism Analysis of Polymerase Chain Reaction Products. Oncogene. 1990;5(7):1037-1043.
Tesler et al. Synthesis and Characterization of DNA Oligomers and Duplexes Containing Covalently attached Molecular Labels: Comparison of Biotin, Fluoreseein, and Pyrene Labels by Thermodynamic and Optical Spectroscopic Measurements. Journal of the American Chemical Society. 1989;111:6966-6976.
Tuessen. Hybridization with Nucleic Acid Probes. Elsevier Science Publishers. 1993. (Table of Contents).

(56) References Cited

OTHER PUBLICATIONS

Tinoco et al. Improved Estimation of Secondary Structure in Ribonucleic Acids. Nature New Biology. 1973;246:40-41.

Traut, Are Proteins Made of Modules? Molecular and Cellular Biochemistry. 1986;70:3-10.

Vogelstein et al. Digital PCR. Proc. Natl. Acad. Sci USA. 1999;96(16):9236-41.

Volkov et al. Recombination and Chimeragenesis by in vitro Heteroduplex Formation and in vivo Repair. Nucleic Acids Research. 1992;27(18):e18i-e18vi.

Wadenback et al. Comparison of standard exponential and linear techniques to amplify small cDNA samples for microarrays. BMC Genomics. 2005:6(1):61.

Wahlestedt et al. Potent and nontoxic antisense oligonucleotides containing locked nucleic acids. Proc. Natl. Acad. Sci. USA. 2000;97(10):5633-5638.

Walker et al. Isothermal In Vitro Amplification of DNA by Restriction Enzyme/DNA Polymerase System. Proc. Natl. Acad. Sci. USA. Applied Biological Sciences. 1992:89:392-396.

Walker et al. Strand displacement amplification—an isothermal, in vitro DNA amplification technique. Nucleic Acids Research 1992;20(7):1691-1696.

Wang et al. Whole genome amplification and high-throughput allelotyping identified five distinct deletion regions on chromosomes 5 and 6 in microdissected early-stage ovarian tumors. Cancer Research. 2001;61;4169-4174.

Wang et al. High-fidelity mRNA amplification for gene profiling. Nature Biotechnology. 2000;18: 457-459.

Wang, et al. Relative stabilities of triple helices composed of combinations of DNA, RNA and 2'-O-methyl-RNA backbones: chimeric circular oligonucleotides as probes Nucleic Acids Res. Apr. 11, 1995;23(7):1157-64.

Westin, et al. Anchored multiplex amplification on a microelectronic chip array. Nat Biotechnol. Feb. 2000; 18(2):199-204.

Wiltshire et al. Detection of Multiple Allergen-Specific IgEs on Microarrays by Immunoassay with Rolling Circle Amplification. Clinical Chemistry, 2000;46(12):1990-1993.

Wu et al. Detection of *Clostridium botulinum* neurotoxin type a using immuno-PCR. Letters in Applied Microbiology. 2001;32:321-325.

Wu et al. The Ligation Amplification Reaction (LAR)-Amplification of Specific DNA Sequences Using Sequential Rounds of Template-Dependent Ligation. Genomics. (1989;4;560-569.
You et al. Directed Evolution of Subtilisin E in *Bacillus subtilis* to Enhance Total Activity in Acqueous Dimethylformamide. Protein Engineering. 1994;9(1):77-83.
Zhang et al. Directed Evolution of a Fucosidase From a Galactosidase by DNA Shuffling and Screening. Proc. Natl. Acad. Sci. USA. 1997;94:4504-4509.
Zhang et al. Protein quantification from complex protein mixtures using a proteomics methodology with single-cell resolution. Proc. Natl. Acad. Sci. USA. 2001;98(10):5497-5502.
Zheng et al. Whole Genome Amplification Increases the Efficiency and Validity of Buccal Cell Genotyping in Pediatric Populations. Cancer Epidermiology. 2001;10;697-700.

* cited by examiner

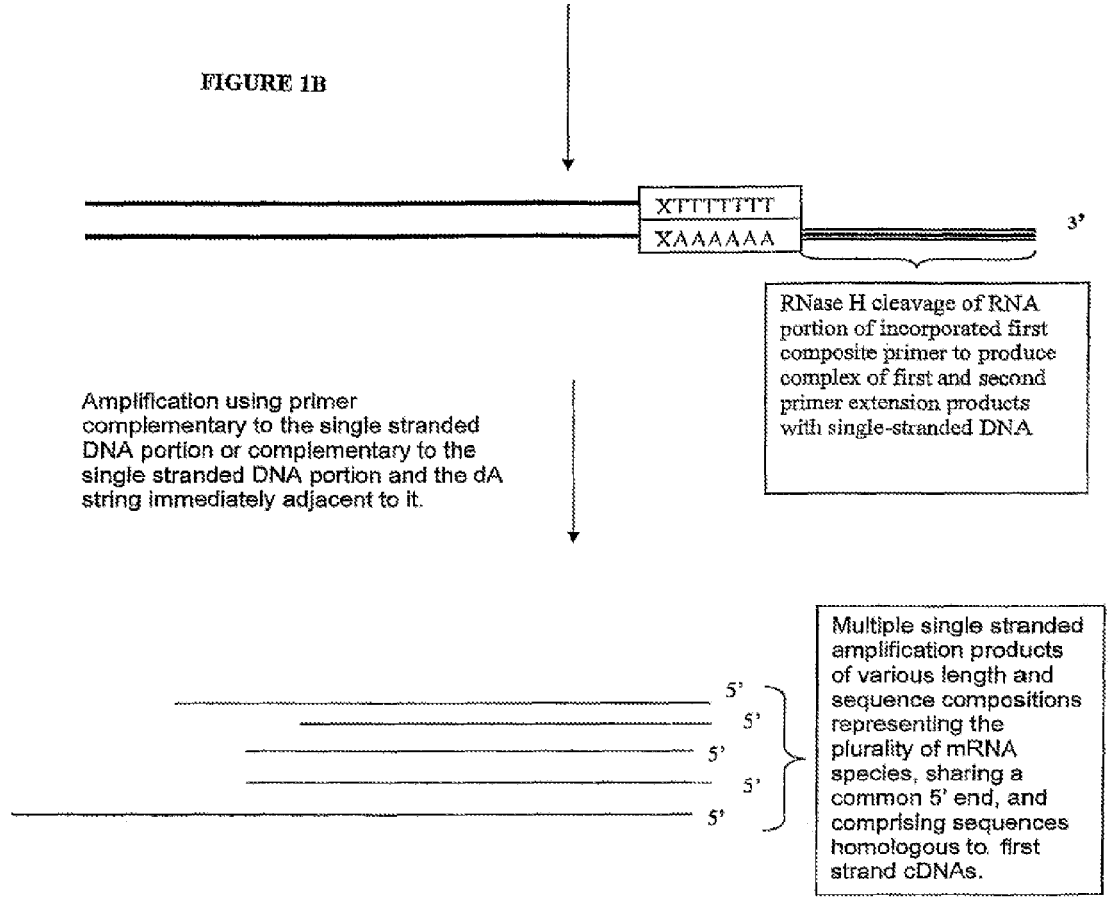

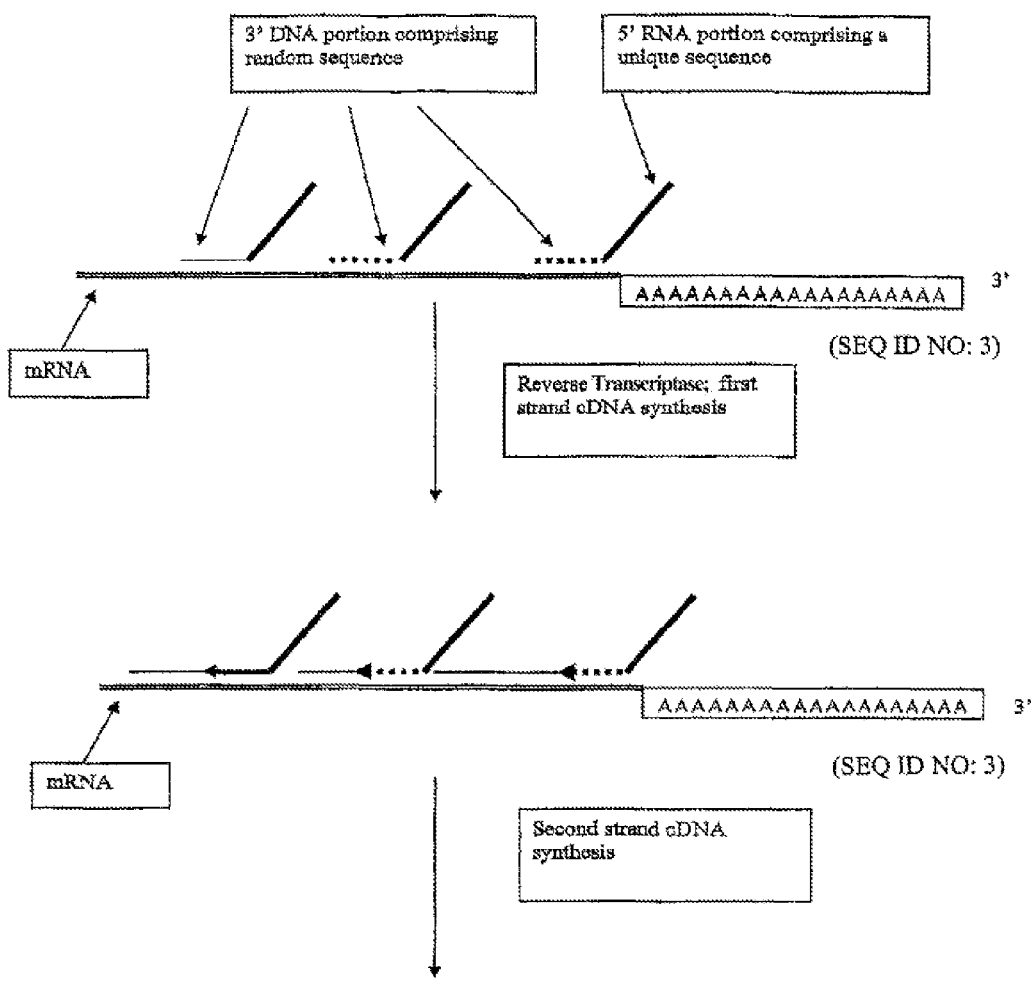

Isothermal linear amplification of the above products using a 3' DNA-5' RNA composite primer complementary to the single stranded DNA tail of the above products and reaction components and conditions as described.

Hybridization of a plurality of first strand chimeric primers

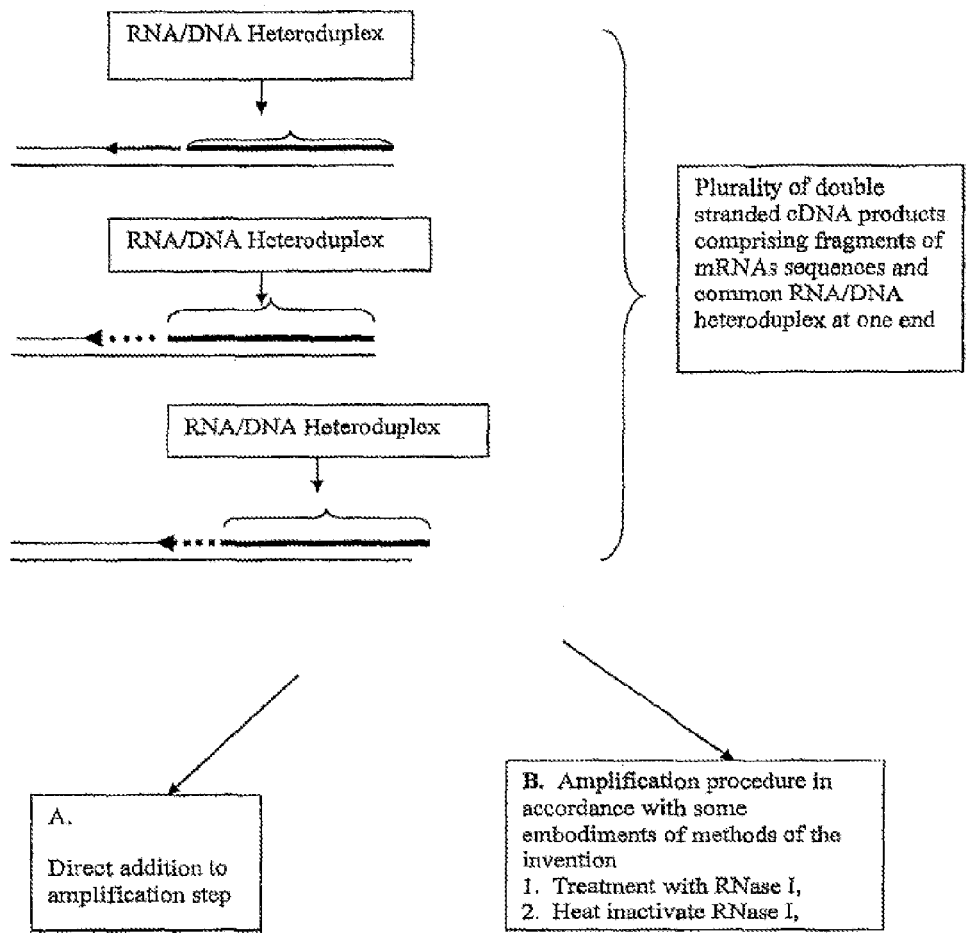

FIGURE 3C Amplification step:
Initial degradation of the RNA portion of the heteroduplex of the double-stranded cDNA (similar reaction with or without RNase I treatment)
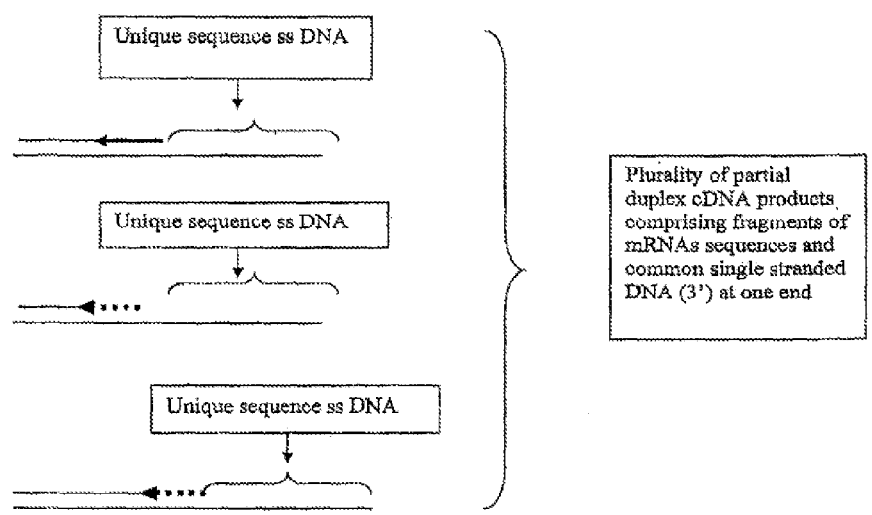

Amplification step in the presence of amplification composite primer and first strand cDNA synthesis chimeric primer that is carried over from the first and second strand cDNA synthesis.

Amplification step following treatment with RNase I:

High efficiency amplification in the absence of competition from first strand-cDNA composite primer.

SEQUENCE LISTING

```
<160> NUMBER OF SEQ ID NOS: 3

<210> SEQ ID NO 1
<211> LENGTH: 19
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(1)
<223> OTHER INFORMATION: n is a, c, g, or t

<400> SEQUENCE: 1
naaaaaaaaa aaaaaaaa                                                 19

<210> SEQ ID NO 2
<211> LENGTH: 21
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(1)
<223> OTHER INFORMATION: n is a, c, g, or t

<400> SEQUENCE: 2
naaaaaaaaa aaaaaaaaaa a                                             21

<210> SEQ ID NO 3
<211> LENGTH: 19
<212> TYPE: DNA
<213> ORGANISM: Artificial Sequence
<220> FEATURE:
<223> OTHER INFORMATION: primer

<400> SEQUENCE: 3
aaaaaaaaaa aaaaaaaa                                                 19
```

NUCLEIC ACID AMPLIFICATION PROCEDURE USING RNA AND DNA COMPOSITE PRIMERS

CROSS-REFERENCE TO RELATED APPLICATIONS

This application claims the benefit of and is a Continuation Application of U.S. application Ser. No. 12/091,843, filed Oct. 3, 2008, now U.S. Pat. No. 7,939,258, which claims the benefit of PCT patent application no. PCT/US2006/035154 filed Sep. 7, 2006, which claims the benefit of U.S. Provisional Application No. 60/714,966, filed on Sep. 7, 2005, all of which is hereby incorporated by reference in its entirety.

The instant application contains a Sequence Listing which has been submitted in ASCII format via EFS-Web and is hereby incorporated by reference in its entirety. Said ASCII copy, created on Aug. 30, 2011, is named 25115-713.301Seqlist.txt and is 2 Kilobytes in size.

FIELD OF THE INVENTION

The invention relates generally to methods and compositions for improved efficiency of nucleic acid amplification procedures, and more specifically to use of a ribonuclease that is specific for single-stranded RNA to remove or reduce the concentration of single-stranded RNA of primers used in amplification procedures.

BACKGROUND

Composite primers comprising a 3'-DNA portion and an RNA portion are employed in previously-described DNA and RNA amplification methods, for example, as described in U.S. Pat. Nos. 6,251,639, 6,692,918, 6,815,164, 6,858,413, and 6,686,156, and in U.S. Application Nos. 2003-0087251, 2003-0003441, 2005-0014192, 2002-0164628, 2003-0215926, 2004-0023271, 2004-0005614, and 2005-0019793. Amplification of an RNA target, for example, as described in U.S. Application Nos. 20030087251, 2005-0003441, and 2005-0014192, and in PCT Application No. WO 02/072772, is initiated by a procedure for the generation of cDNA which utilizes composite primers (comprising an RNA and a 3'-DNA portion) for first strand cDNA synthesis. The RNA portion of the composite primer may comprise a sequence which does not hybridize to the target RNA sequence. The 3'-DNA portion comprises a sequence that hybridizes to the target RNA sequence. The 3'-DNA portion of the first strand cDNA primer may comprise a sequence that is complementary to the poly-A tail of mRNA, or a random sequence that is hybridizable to sequences across the RNA target sequence. Alternatively the 3'-DNA portion may comprise a sequence that is complementary to specific sequence(s) of the RNA target. The first strand cDNA synthesis is carried out by a reverse transcriptase, which extends the hybridized primer along the target RNA to form a cDNA/RNA heteroduplex. Any combination of first strand composite cDNA primers is possible. Thus, first strand cDNA synthesis may be carried out using a single composite primer, a mixture of composite primers with a random 3'.-DNA sequence, such as a random hexamer, a combination of composite primers comprising random and sequence-specific 3'-DNA portions, etc. Second strand cDNA synthesis along the first strand cDNA, and reverse transcription of the RNA portion of the first strand primer extension product, results in the formation of unique double stranded cDNA molecules with a DNA/RNA heteroduplex at one end. The heteroduplex at the end of the double-stranded cDNA is a substrate for RNase H, which can degrade RNA of this heteroduplex to generate a unique partial duplex cDNA with a single-stranded DNA portion at the 3'-end of the second strand cDNA. This single-stranded sequence comprises a sequence that is complementary to the RNA portion of the first strand cDNA composite primer utilized, and serves as a priming site for subsequent amplification using a composite DNA/RNA amplification primer. Amplification is carried out using a composite amplification primer comprising a 3'-DNA portion and an RNA portion, a DNA polymerase with strand displacement activity, and an enzyme capable of degrading RNA in an RNA/DNA heteroduplex, such as RNase H.

In one procedure for amplifying an RNA target as described above, the first strand cDNA chimeric primer comprises a RNA portion that is not hybridizable to the target RNA sequence and comprises a sequence of the chimeric amplification primer. The double stranded cDNA generated at the completion of second strand cDNA synthesis, comprises a unique DNA/RNA heteroduplex at one end. The appended sequence at one end of the double stranded cDNA comprises the RNA portion of the first strand cDNA chimeric primer and its DNA complement. Incubation of this product with an enzyme that degrades RNA in an RNA/DNA heteroduplex, such as RNase H, results in the degradation of the RNA portion of the heteroduplex, releasing a site for primer hybridization to permit amplification with the chimeric amplification primer. Insofar as the amplification priming site contains sequences that are complementary to sequences in both the first strand cDNA chimeric primer and the chimeric amplification primer, any remaining first strand cDNA chimeric primer, which was not engaged in the synthesis of first strand cDNA, is capable of competing with the amplification chimeric primer for binding at the amplification primer binding site. This competition has the potential of impacting amplification efficiency.

This competition is dependent on the concentrations of the two primers.

Whereas the chimeric amplification primer is typically added to the amplification reaction mixture at high concentration sufficient for effective productive hybridization and subsequent amplification to generate multiple copies of the single-stranded amplification products, the first strand primer is carried over into the amplification reaction mixture with the cDNA reaction mixture. The amount of first strand cDNA chimeric primer carried over into the amplification reaction mixture will be dependent on the amount added to the first strand synthesis reaction mixture, and the complexity of the primer composition. For example, the total amount of first strand chimeric primer may be particularly high when the primer employed is designed for random priming throughout the length of RNA transcripts, in contrast to a primer employed for cDNA synthesis which is initiated at defined sequences of RNA transcripts in the sample. The initiation of cDNA synthesis at specific sequences of RNA transcripts may entail hybridization and initiation of synthesis at the poly-A tail of eukaryotic mRNAs, or at sequences specific for defined internal mRNA species, such as a sequence common to a family of transcripts.

The amount (concentration) of the first strand chimeric primer added to a reaction mixture is often determined based on efficient priming and may therefore be in excess to the amount of RNA transcripts in the samples. Chimeric DNA/RNA primers designed to randomly prime cDNA synthesis throughout the length of an RNA transcript comprise a large population of primer sequences to accommodate the representation of random sequence at the 3' end, and thus require a large concentration of the total population of primers, for effective representation of each of the priming sequences. Similarly, the total concentration of primers added for priming at multiple transcript sequences will also be higher than that required for any single primer. Effective linear amplification of the entire population of transcripts in the mixture can be achieved with the use of a single amplification primer, when all the chimeric primers employed for first strand cDNA synthesis comprise an RNA portion of the same sequence. Thus, the effective combined concentration of the RNA portion of the chimeric primer is particularly high whereas the concentration of any of the 3' DNA portions is relatively low. The first strand cDNA chimeric primer remaining in the reaction mixture following the second strand synthesis reaction, and carried over into the amplification reaction mixture, is high when employing a random priming strategy. Insofar as all the RNA portions of the first strand chimeric primers include the RNA sequence of the chimeric amplification primer, the amplification efficiency may be impacted by competition of both sets of primers for binding to the priming site on the amplification target.

There is a need for an improved amplification procedure in which single-stranded RNA of a first single-stranded-RNA-containing primer is degraded prior to a second reaction employing a second single-stranded-RNA-containing primer, to prevent or reduce competition between the two primers for binding to the target in an amplification reaction employing the second primer.

BRIEF SUMMARY OF THE INVENTION

The invention provides methods, compositions, and kits for amplification using primers containing single-stranded RNA, e.g., RNA/DNA composite primers, as well as applications of the amplification methods. The methods described herein employ an enzyme capable of cleaving single-stranded RNA (i.e., specific for single-stranded RNA) to cleave the RNA portion of excess unhybridized first composite primer prior to amplification with a composite amplification primer, and/or single-stranded RNA portions of amplification products Accordingly, in one aspect, the invention provides methods for amplification of a template polynucleotide. In one embodiment, the method comprises: (a) extending a first primer hybridized to the polynucleotide template with at least one enzyme comprising a DNA polymerase activity, wherein the first primer is a composite primer comprising an RNA portion and a 3' DNA portion, whereby a complex comprising a first primer extension product and the template polynucleotide is produced (b) extending a second primer hybridized to the first primer extension product to produce a complex comprising a first primer extension product and a second primer extension product; (c) incubating the reaction mixture comprising the products of step (b) with an enzyme that is capable of cleaving single-stranded RNA, whereby unhybridized single-stranded RNA of the RNA portion of the first primer is cleaved; (d) inactivating the enzyme that is capable of cleaving single-stranded RNA; (e) cleaving RNA from the first primer in the complex of first primer extension product and second primer extension product with at least one enzyme that cleaves RNA from an RNA/DNA hybrid such that a composite amplification primer hybridizes to the second primer extension product, wherein the composite amplification primer comprises an RNA portion and a 3' DNA portion; and (f) extending the composite amplification primer hybridized to the second primer extension product with at least one enzyme comprising DNA-dependent DNA polymerase activity, whereby the first primer extension product is displaced, RNA is cleaved from the composite amplification primer and another composite amplification hybridizes such that primer extension and strand displacement are repeated, and whereby multiple copies of a polynucleotide amplification product are generated.

In another embodiment, the method comprises: (a) incubating a reaction mixture, said reaction mixture comprising: (i) a template polynucleotide; (ii) a first primer, wherein. the first primer is a composite primer that is hybridizable to at least one (i.e., one or a multiplicity) template polynucleotide site(s), wherein the composite primer comprises an RNA portion and a 3' DNA portion; and (iii) a DNA-dependent DNA polymerase and/or an RNA-dependent DNA polymerase (which may be present as a separate enzyme or as an enzyme comprising both DNA-dependent DNA polymerase and RNA-dependent DNA polymerase activities); wherein the incubation is under conditions that permit composite primer hybridization and primer extension, whereby a complex comprising a first primer extension product and the template polynucleotide is generated; (b) incubating a reaction mixture, said reaction mixture comprising: (i) the first primer extension product; (ii) a second primer; (iii) at least one enzyme comprising DNA-dependent DNA polymerase activity; (iv) at least one enzyme comprising RNA-dependent DNA polymerase activity; and (v) optionally, at least one enzyme capable of cleaving RNA from an RNA/DNA hybrid; wherein the incubation is under conditions permitting formation of a complex comprising the first primer extension product and a second primer extension product; (c) incubating the reaction mixture of (b) (or an aliquot thereof) with an enzyme capable of cleaving single-stranded RNA (e.g., RNase I); (d) inactivating the enzyme capable of cleaving single-stranded RNA (e.g., by elevating the temperature of the reaction mixture) or removing the enzyme capable of cleaving single-stranded RNA from the reaction mixture; and (e) incubating a reaction mixture, said reaction mixture comprising (i) the reaction products generated according to steps (a), (b), (c), and (d) (or an aliquot thereof); (ii) a composite amplification primer, wherein the composite amplification primer comprises an RNA portion and a 3' DNA portion; (iii) a DNA-dependent DNA polymerase; and (iv) an enzyme that cleaves RNA from an RNA/DNA hybrid, e.g., RNase H; wherein the incubation is under conditions that permit RNA cleavage from an RNA/DNA heteroduplex, primer hybridization, primer extension, and displacement of the first primer extension product from the complex comprising the first primer extension product and the second primer extension product, whereby another composite amplification primer hybridizes and primer extension and strand displacement are repeated; whereby multiple copies of a polynucleotide (generally, DNA) amplification product are generated.

In another embodiment, the method comprises: (i) contacting a reaction mixture comprising a first primer and a complex of first primer extension product and second primer extension product with an enzyme capable of cleaving single-stranded RNA, wherein the complex of first primer extension product and second primer extension product is produced by extension of a first primer hybridized to the template polynucleotide with a DNA polymerase, wherein the first primer is a composite primer comprising an RNA portion and a 3' DNA portion, wherein the second primer extension product is generated by extension of a second primer hybridized to the first primer extension product; (ii) inactivating the enzyme capable of cleaving single-stranded RNA; and (iii) contacting the complex of first primer extension product and second primer extension product with at least one enzyme that cleaves RNA from an RNA/DNA hybrid and a composite amplification primer, said composite amplification primer comprising an RNA portion and a 3' DNA portion, wherein the composite amplification primer hybridizes to the second primer extension product; whereby said first primer extension product is displaced, RNA is cleaved from the composite amplification primer, and another composite amplification primer hybridizes such that primer extension and strand displacement are repeated; and whereby multiple copies of a polynucleotide amplification product are generated.

In some embodiments, the first composite primer comprises a random sequence or a partially randomized sequence. In embodiments utilizing a composite primer with random or partially random sequence, the composite primer may be a population or pool of different primers comprising at least 2, at least 3, at least 4, at least 5, at least 10, at least 15, at least 20, at least 30, at least 40, at least 50, or at least 100 different sequences. In other embodiments, the composite primer contains one or more "degenerate" nucleotides that are able to hybridize to multiple different nucleotide bases (e.g., inosine, which is able to hybridize to all four canonical bases).

The methods are applicable to amplifying any target polynucleotide, including, for example, DNA (such as genomic DNA, including human and other mammalian, bacterial, or viral genomic DNA, or any other species or combination of species) and RNA (including synthetic or natural RNA, such as total RNA, mRNA, noncoding RNA, ribosomal RNA, or viral RNA). One or more steps may be combined and/or performed sequentially (often in any order, as long as the requisite product(s) are able to be formed), and as is evident, the invention includes various combinations of the steps described herein. It is also evident, and is described herein, that the invention encompasses methods in which the initial, or first, step is any of the steps described herein. For example, the methods of the invention do not require that the first step be hybridization of first composite primer. Methods of the invention encompass embodiments in which later, "downstream" steps are an initial step.

In another aspect, the invention provides methods for amplification of an RNA sequence of interest. In one embodiment, the invention provides a method for generating multiple copies of a sequence complementary to an RNA sequence of interest, comprising: (a) extending a first primer hybridized to a target RNA with at least one enzyme comprising RNA-dependent DNA polymerase activity, wherein the first primer is a composite primer comprising an RNA portion and a 3' DNA portion, whereby a complex comprising a first primer extension product and the target RNA is produced; (b) cleaving the target RNA in the complex of step (a); (c) extending a second primer hybridized to the first primer extension product with at least one enzyme comprising DNA-dependent DNA polymerase activity and at least one enzyme comprising RNA-dependent DNA polymerase activity, whereby a second primer extension product is produced to form a complex of first and second primer extension products; (d) incubating the reaction mixture comprising the products of step (c) and excess first primer, if any, with an enzyme that is capable of cleaving single-stranded RNA, whereby unhybridized single-stranded RNA of the RNA portion of the first primer is cleaved; (e) inactivating the enzyme that is capable of cleaving single-stranded RNA; (f) cleaving RNA from the first primer in the complex of first and second primer extension products with at least one enzyme that cleaves RNA from an RNA/DNA hybrid such that a composite amplification primer hybridizes to the second primer extension product, wherein the composite amplification primer comprises an RNA portion and a 3' DNA portion; and (g) extending the composite amplification primer hybridized to the second primer extension product with at least one enzyme comprising DNA-dependent DNA polymerase activity; whereby said first primer extension product is displaced, RNA is cleaved from the composite amplification primer and another composite amplification primer hybridizes such that primer extension and strand displacement are repeated, and whereby multiple copies of a polynucleotide sequence complementary to the RNA sequence of interest are generated.

In another embodiment, the invention provides a method of generating multiple copies of an RNA sequence of interest, comprising: (a) extending a first primer hybridized to a target RNA with at least one enzyme comprising RNA-dependent DNA polymerase activity, wherein the first primer is a composite primer comprising an RNA portion and a 3' DNA portion, whereby a complex comprising a first primer extension product and the target RNA is produced; (b) cleaving the target RNA in the complex of step (a); (c) extending a second primer hybridized to the first primer extension product with at least one enzyme comprising DNA-dependent DNA polymerase activity and at least one enzyme comprising RNA-dependent DNA polymerase activity, whereby a second primer extension product is produced to form a complex of first and second primer extension products; (d) incubating the reaction mixture comprising the products of step (c) and excess first primer, if any, with an enzyme that is capable of cleaving single-stranded RNA, whereby unhybridized single-stranded RNA of the RNA portion of the first primer is cleaved; (e) inactivating the enzyme that is capable of cleaving single-stranded RNA; (f) cleaving RNA from the first primer in the complex of first and second primer extension products with at least one enzyme that cleaves RNA from an RNA/DNA hybrid such that a composite amplification primer hybridizes to the second primer extension product, wherein the composite amplification primer comprises an RNA portion and a 3' DNA portion; (g) extending said composite amplification primer hybridized to the second primer extension product with at least one enzyme comprising DNA-dependent DNA polymerase activity, whereby said first primer extension product is displaced, RNA is cleaved from the composite amplification primer and another composite amplification primer hybridizes such that primer extension and strand displacement are repeated; and (h) hybridizing the displaced first primer extension product with a polynucleotide comprising a propromoter and a region which is hybridizable to the displaced first primer extension product under conditions which allow transcription to occur by RNA polymerase, such that RNA transcripts are produced comprising sequences complementary to the displaced first primer extension product, whereby multiple copies of the RNA sequence of interest are generated.

In another embodiment, the invention provides a method of generating multiple copies of a polynucleotide sequence complementary to an RNA sequence of interest comprising: (a) incubating a reaction mixture, said reaction mixture comprising: (i) a target RNA; (ii) a first primer that is hybridizable to a target RNA, wherein the first primer is a composite primer comprising an RNA portion and a 3' DNA portion; and (iii) at least one enzyme comprising RNA-dependent DNA polymerase activity, wherein the incubation is under conditions that permit primer hybridization and primer extension, whereby a complex comprising a first primer extension product and the target RNA is formed; (b) incubating a reaction mixture, said reaction mixture comprising: (i) the first primer extension product; (ii) a second primer; (iii) at least one enzyme comprising DNA-dependent DNA polymerase activity; (iv) at least one enzyme comprising RNA-dependent DNA polymerase activity; and (v) optionally, at least one enzyme capable of cleaving RNA from an RNA/DNA hybrid; wherein the incubation is under conditions permitting formation of a complex comprising the first primer extension product and a second primer extension product; (c) incubating at least a portion of the reaction mixture of (b) with an enzyme capable of cleaving single-stranded RNA; (d) inactivating the enzyme capable of cleaving single-stranded RNA; and (e) incubating a reaction mixture, said reaction mixture comprising: (i) the reaction products generated according to steps (a), (b), (c), and (d); (ii) at least one enzyme capable of cleaving RNA from an RNA/DNA hybrid; (iii) a composite amplification primer, wherein the composite amplification primer comprises a RNA portion and a 3' DNA portion; (iv) at least one enzyme comprising DNA-dependent DNA polymerase activity, wherein the incubation is under conditions that permit cleavage of RNA, composite primer hybridization, primer extension, and displacement of the first primer extension product from the complex comprising the first primer extension product and the second primer extension product, whereby another composite amplification primer hybridizes and primer extension and strand displacement are repeated; whereby multiple copies of a polynucleotide sequence complementary to the RNA sequence of interest are generated.

In another embodiment, the invention comprises a method of generating multiple copies of a polynucleotide sequence complementary to an RNA sequence of interest, said method comprising: (i) contacting a reaction mixture comprising a complex of first and second primer extension products and a first primer with an enzyme capable of cleaving single-stranded RNA, wherein the first primer extension product is produced by extension of the first primer hybridized to a target RNA with at least one enzyme comprising RNA-dependent DNA polymerase activity, wherein the first primer is a composite primer comprising an RNA portion and a 3' DNA portion, wherein the second primer extension product is generated by extension of a second primer hybridized to the first primer extension product; (ii) inactivating the enzyme capable of cleaving single-stranded RNA; and (iii) contacting the complex of first and second primer extension products with a composite amplification primer and at least one enzyme that cleaves RNA from an RNA/DNA hybrid, said composite amplification primer comprising an RNA portion and a 3' DNA portion, wherein the composite amplification primer hybridizes to the second primer extension product; whereby said first primer extension product is displaced, RNA is cleaved from the composite amplification primer and another composite amplification primer hybridizes such that primer extension and strand displacement are repeated; and whereby multiple copies of a polynucleotide sequence complementary to the RNA sequence of interest are generated.

In some embodiments of the methods described herein, the RNA portion of the first primer and/or amplification primer is 5' with respect to the 3' DNA portion. In some embodiments, the 5' RNA portion of the first primer and/or amplification primer is adjacent to the 3' DNA portion. In some embodiments, the first primer comprises a random sequence. In some embodiments, the first primer is hybridizable to a multiplicity of template polynucleotide sites. In some embodiments, the first primer is a tailed primer that comprises a 5' portion that is not hybridizable to the target RNA under conditions in which the first primer hybridizes to the target RNA. In some embodiments for amplification of mRNA, the 3' DNA portion of the first primer comprises a poly-dT sequence, and optionally comprises at least 1 random nucleotide at the 3' end.

In some embodiments, the second primer comprises DNA. In some embodiments, the second primer is a random primer. In some embodiments in which the target polynucleotide is RNA, the second primer comprises a fragment of the target RNA hybridized to the first primer extension product.

The enzymes which may be used in the methods and compositions are described herein. For example, the enzyme that cleaves RNA from an RNA/DNA heteroduplex may be an RNase H, and the RNA-dependent DNA polymerase may be reverse transcriptase. The RNA-dependent DNA polymerase may comprise an RNase H enzyme activity, or separate enzymes may be used. Similarly, a DNA polymerase may comprise both RNA-dependent and DNA-dependent DNA polymerase enzyme activities, or separate enzymes may be used. A DNA-dependent DNA polymerase, an RNA-dependent DNA polymerase, and the enzyme that cleaves RNA can also be the same enzyme, or separate enzymes comprising each of these activities may be used. The enzyme that is capable of cleaving single-stranded RNA may be, for example, RNase I, RNase T, RNase A, or combination thereof. Generally, an enzyme with little or no sequence specificity, and an enzyme that does not cleave the RNA in an RNA/DNA heteroduplex, is preferred. In some embodiments, the enzyme capable of cleaving single-stranded RNA is RNase I. In one embodiment, the RNase I is inactivated by heat.

In some embodiments, methods of the invention are used to generate labeled polynucleotide products (generally DNA products). In some embodiments of methods for generating labeled amplification, e.g., DNA, products, at least one type of nucleotide, e.g.; dNTP, used is a labeled nucleotide, e.g., dNTP. In other embodiments, a labeled nucleotide terminator is incorporated, for use in sequencing applications. In other embodiments of methods for generating labeled polynucleotide, e.g., DNA, products, a labeled composite primer is used.

In some embodiments, a non-canonical nucleotide is incorporated into the amplification products by extension of the composite amplification primer in the presence of a non-canonical nucleotide. In one embodiment, the non-canonical nucleotide is dUTP. In some embodiments, polynucleotide products comprising a non-canonical nucleotide are fragmented and/or labeled, for example, according to methods described in U.S. Patent Application No. 2004/0005614.

In any of the methods described herein, the amplification products may be contacted with an enzyme that is capable of cleaving single-stranded RNA, e.g., RNase I.

In another aspect, the invention provides methods for amplifying a polynucleotide sequence complementary to a target polynucleotide sequence, comprising: (a) extending a composite primer in a complex comprising (i) a polynucleotide template comprising the target sequence; and (ii) the composite primer, said composite primer comprising an RNA portion and a 3' DNA portion, wherein the composite primer is hybridized to the polynucleotide template; (b) cleaving the RNA portion of the annealed composite primer with an enzyme that cleaves RNA from an RNA/DNA hybrid such that another composite primer hybridizes to the template and repeats primer extension and strand displacement, whereby multiple copies of the complementary sequence of the target sequence are produced; and (c) incubating said multiple copies of the complementary sequence of the target sequence with an enzyme that is capable of cleaving single-stranded RNA, wherein RNA from the composite primer is cleaved.

In another aspect, the invention provides a method of generating multiple copies of a polynucleotide sequence complementary to an RNA sequence of interest, said method comprising: (a) extending a composite amplification primer in a complex comprising: (i) a complex of first and second primer extension products, wherein the first primer extension product is produced by extension of a first primer hybridized to a target RNA with at least one enzyme comprising RNA-dependent DNA polymerase activity, wherein the first primer is a composite primer comprising an RNA portion and a 3' DNA portion, wherein the second primer extension product is generated by extension of a second primer hybridized to the first primer extension product, and wherein RNA from the complex of first and second primer extension products is cleaved with at least one enzyme that cleaves RNA from an RNA/DNA hybrid; and (ii) a composite amplification primer, said composite amplification primer comprising an RNA portion and a 3' DNA portion, wherein the composite amplification primer is hybridized to the second primer extension product; whereby said first primer extension product is displaced, RNA is cleaved from the composite amplification primer and another composite amplification primer hybridizes such that primer extension and strand displacement are repeated; and whereby multiple copies of a polynucleotide sequence complementary to the RNA sequence of interest are generated; and (b) contacting said multiple copies of the complementary sequence of the RNA sequence of interest with an enzyme that is capable of cleaving single-stranded RNA, wherein RNA from the composite primer is cleaved.

The invention also provides methods which employ (usually, analyze) the products of the amplification methods of the invention, such as detection of sequence alteration(s) (e.g., genotyping, nucleic acid mutation detection, analysis of splice variants, and the like); determining presence or absence of a sequence of interest; quantifying a sequence of interest; gene expression profiling; subtractive hybridization; preparation of subtractive hybridization probe; differential amplification; preparation of libraries (including genomic, cDNA and differential expression libraries); preparation of an immobilized nucleic acid (which can be a nucleic acid immobilized on a microarray, preparing labeled probes for analysis on arrays (including high density arrays) for the detection and quantification of sequences of interest, including, for example, sequence determination, detecting sequence variation and genotyping; comparative genome hybridization; detection and/or identification of novel RNAs; and characterizing nucleic acids using the amplification nucleic acid products generated by the methods of the invention. Amplification products generated as described herein may also be used in gene expression analysis, including gene expression profiling or analysis of differential gene expression, for example, by quantitative PCR or analysis on microarrays for example, low, medium, or high density oligonucleotide or cDNA arrays.

Any of the methods of the invention can be used to generate polynucleotide products that are suitable for characterization of a polynucleotide sequence of interest in a sample. In one embodiment, the invention provides methods for characterizing (for example, detecting (presence or absence) and/or quantifying) a polynucleotide sequence of interest comprising: (a) amplifying a target polynucleotide by any of the methods described herein; and (b) analyzing the amplification products. Step (b) of analyzing the amplification products can be performed by any method known in the art or described herein, for example by detecting and/or quantifying amplification products that are hybridized to a probe. These amplification products may or may not be labeled. Any of the methods of the invention can be used to generate polynucleotide (such as DNA) products that are labeled by incorporating labeled nucleotides and/or labeled composite primers into appropriate step(s) of the methods. These labeled products are particularly suitable for quantification and/or identification by methods known in the art, which include the use of arrays such as cDNA microarrays and oligonucleotide arrays. In one aspect, the invention provides a method of characterizing a polynucleotide sequence of interest, comprising (a) amplifying a target polynucleotide by a method described herein to generate labeled polynucleotide products; and (b) analyzing the labeled polynucleotide products. In some embodiments, the step of analyzing polynucleotide products comprises determining amount of said products, whereby the amount of the polynucleotide sequence of interest present in a sample is quantified.

The amplification products can also serve as templates for further analysis such as sequence analysis, polymorphism detection (including multiplex SNP detection) using, e.g., oligonucleotide ligation-based assays, analysis using Invader, Cleavase or limited primer extension, and other methods known in the art. For methods that generally require larger volumes of input material, the methods of the invention may be used to "pre" amplify a pool of polynucleotides to generate sufficient input material for subsequent analysis.

In another embodiment, the polynucleotide products can be analyzed by, for example, contacting them with at least one probe. In some embodiments, the at least one probe is provided as a microarray. The microarray can comprise at least one probe immobilized on a solid or semi-solid substrate fabricated from a material selected from the group consisting of paper, glass, ceramics, plastic, polypropylene, polystyrene, nylon, polyacrylamide, nitrocellulose, silicon, other metals, and optical fiber. A probe can be immobilized on the solid or semi-solid substrate in a two-dimensional configuration or a three-dimensional configuration comprising pins, rods, fibers, tapes, threads, beads, particles, microtiter wells, capillaries, and cylinders.

In another aspect, the invention provides methods of determining a gene expression profile in a sample, the methods comprising (a) amplifying RNA templates in a sample using any of the methods described herein; and (b) determining an amount of amplification products of each RNA sequence of interest in the sample, whereby the gene expression profile of the sample is determined. The invention further provides methods of determining a gene expression profile by determining an amount of amplification products of each RNA sequence of interest in a sample, the sample comprising multiple copies of RNA template amplified by any of the methods described herein, whereby the gene expression profile of the sample is determined.

Additionally, the invention also provides methods for archiving polynucleotide templates. In some embodiments, the amplification methods of the invention provide representative amplification of the sequences of the template polynucleotide, and amplified products produced by the methods may be used as an archival source for the original template polynucleotide. Accordingly, the invention provides methods for archiving a polynucleotide template by storing the amplification products produced by the methods of the invention. The archived amplification products may be analyzed as described herein, or may be subjected to further amplification in accordance with the methods of the invention.

In one aspect, the invention provides methods for degrading excess RNA-containing primer in a nucleic acid amplification mixture that contains the RNA-containing primer and amplification products, by incubating the amplification mixture with an enzyme that specifically cleaves single-stranded RNA, such as RNase I, prior to use of the amplification products in subsequent applications.

In another aspect, the invention provides products (e.g., multiple copies of a template polynucleotide or complement thereof) produced by the methods disclosed herein.

The invention also provides compositions, kits, complexes, reaction mixtures and systems comprising various components (and various combinations of the components) used in the amplification methods described herein.

In another aspect, the invention provides compositions comprising any of the complexes (which are generally considered as intermediates with respect to the final amplification products), for example a complex of first and second primer extension product in a reaction mixture which has been incubated with an enzyme capable of cleaving single-stranded RNA, as described herein.

In another aspect, the invention includes any one or more products (including intermediates) and compositions comprising the products (including intermediates) produced by any aspect of the methods of the invention.

In another aspect, the invention provides reaction mixtures (or compositions comprising reaction mixtures) which contain various combinations of components described herein.

In another aspect, the invention provides kits for conducting the methods described herein. These kits, in suitable packaging and generally (but not necessarily) containing suitable instructions, contain one or more components used in the amplification methods.

In another aspect, the invention provides systems for effecting the amplification methods described herein.

BRIEF DESCRIPTION OF THE DRAWINGS

FIG. 1A depicts first and second strand synthesis. A first composite primer comprising a 3' poly-dT DNA sequence and a random nucleotide at the 3' end hybridizes to the poly-A tail of mRNA (SEQ ID NO: 1; SEQ ID NO: 2). The primer also includes a 5' RNA sequence which is not complementary to the mRNA sequences (unique sequence not complementary). After extension of the first primer, a second primer extension product is generated, forming a complex of first and second primer extension products with an RNA/DNA heteroduplex at one end. FIG. 1B depicts cleavage of RNA from the first primer in the RNA/DNA heteroduplex with RNase H, which permits binding of an amplification primer and amplification of the target sequence using a DNA polymerase with strand displacement activity.

FIG. 2. Schematic description of an RNA amplification method utilizing 3' DNA-5' RNA composite primers comprising a 3' portion comprising a random DNA sequence (SEQ ID NO: 3). FIG. 2A: The amplification is initiated by hybridization of first composite primers to complementary sequences of the one or more (plurality of) mRNA species in the sample, and synthesis of first strand cDNAs by reverse transcriptase. Multiple first primer extension products are generated from the extension of the various random primers, each of the products comprising a 5' RNA sequence which is unique and non-complementary to the mRNA.

FIG. 3 schematically depicts RNA amplification using chimeric primers (SEQ ID NO: 3), incorporating treatment with RNase I following second strand cDNA synthesis. FIG. 3B: Formation of a double-stranded cDNA product with an RNA/DNA heteroduplex. FIG. 3C: Degradation of RNA in the RNA/DNA heteroduplex to form product with 3' single-stranded DNA at one end.

DETAILED DESCRIPTION

Figure 1:
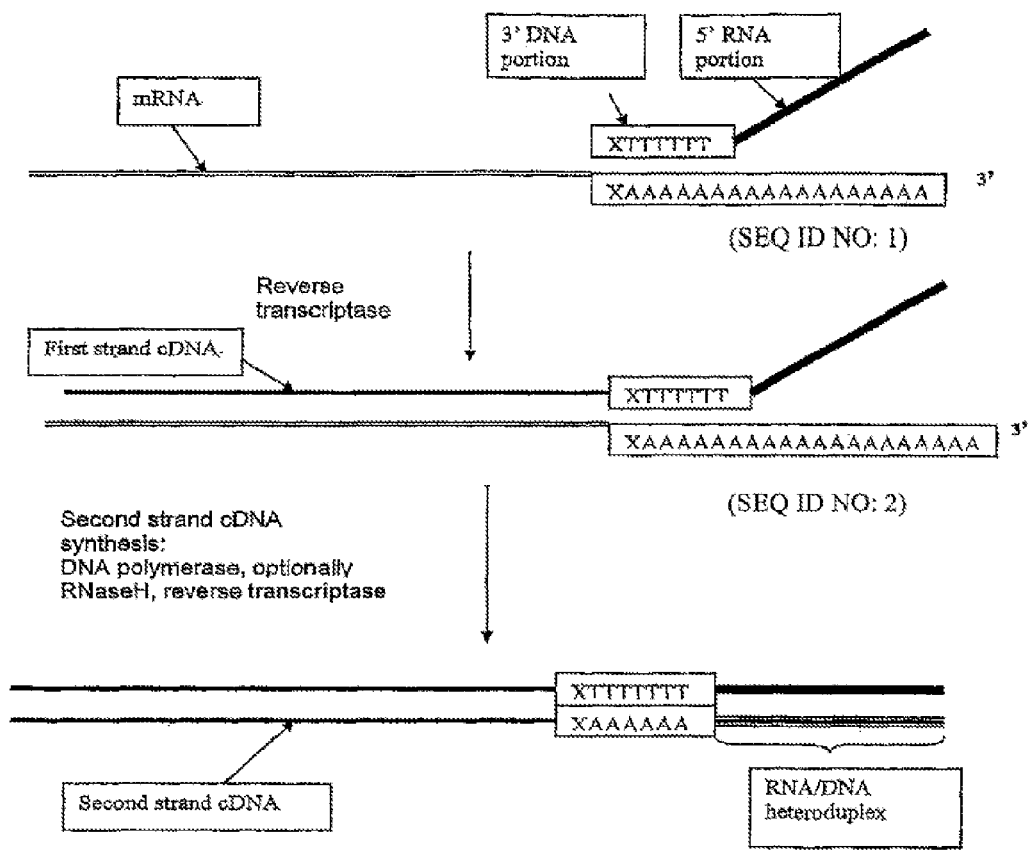
FIG. 1. Schematic description of a procedure for mRNA amplification.
Figure 2B:
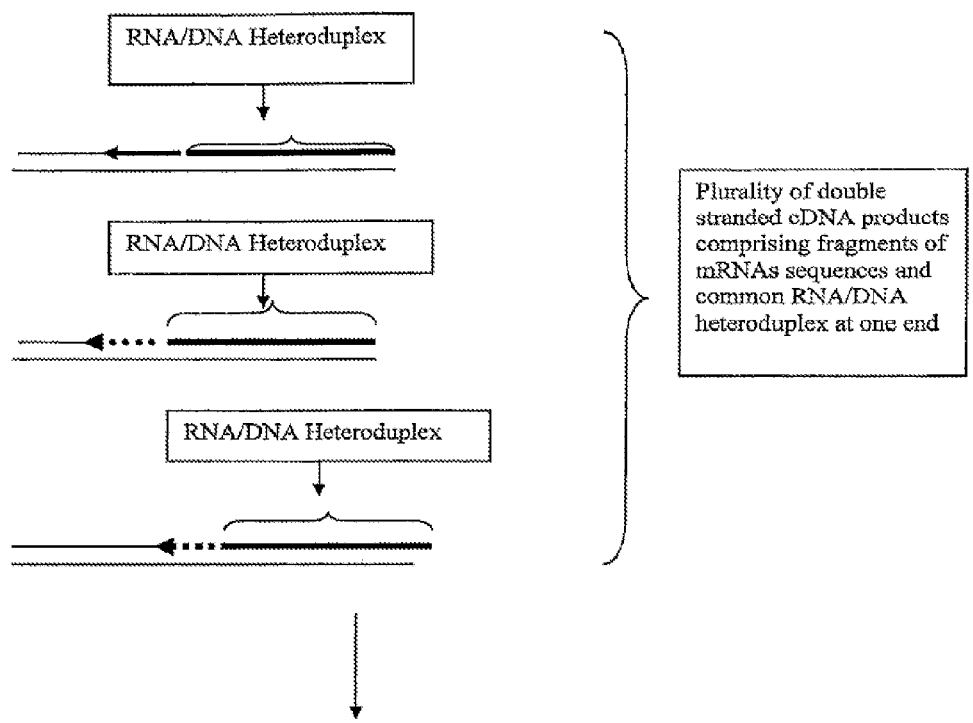
FIG. 2B: Second strand cDNA synthesis is carried out to generate multiple double stranded products comprising a common 5' end RNA/DNA heteroduplex.
Figure 2C:
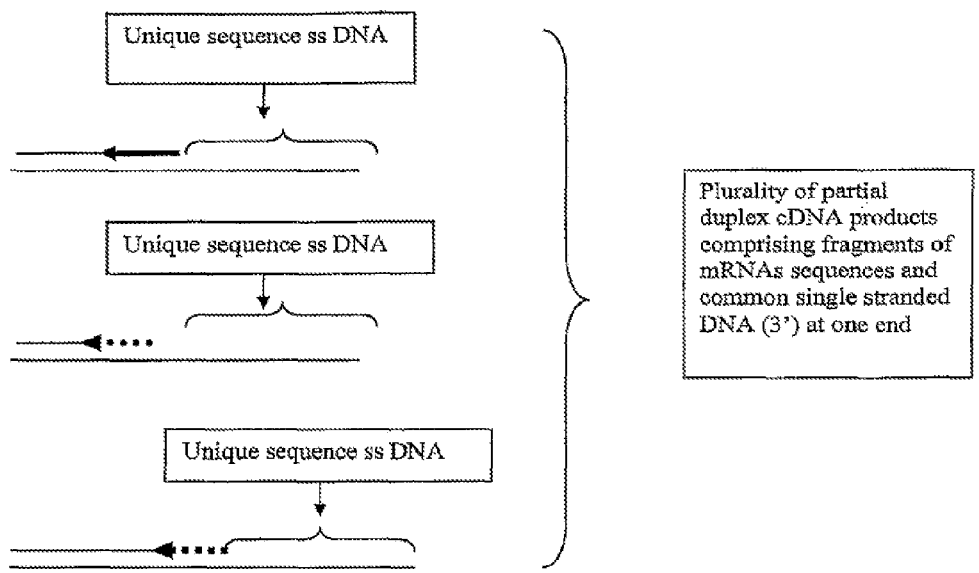
FIG. 2C: RNase H activity cleaves the RNA portion of the heteroduplex to generate multiple partial duplex products comprising double stranded portions having sequence identity to the mRNAs in the sample, and a single-stranded DNA tail at one end comprising a unique sequence complementary to the unique RNA sequence of the composite primer.
Figure 2D:
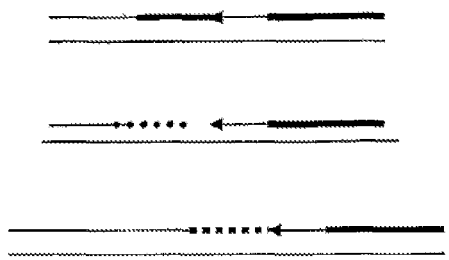
FIG. 2D: These partial duplex products are substrates for amplification with a composite amplification primer. The composite amplification primer may be complementary to the cDNA complement of the unique sequence from the first primer, which may result in competition between the first composite primer and the composite amplification primer for binding to the single-stranded DNA sequence.
Figure 2D:
Figure 2D:
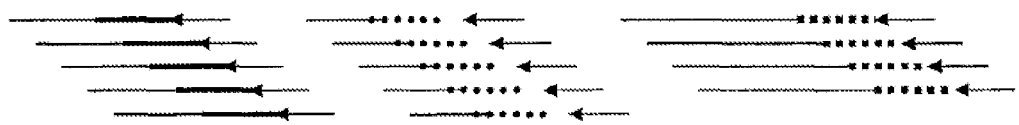

The invention provides methods, compositions, and kits for an improved nucleic amplification procedure. In a method such as an amplification method in which two primers containing single-stranded RNA are used, an enzyme capable of cleaving single-stranded RNA is employed to degrade single-stranded RNA of the first primer, prior to addition of a second single-stranded RNA containing primer. It is often desirable to remove a first single-stranded RNA containing primer (i.e., one or a multiplicity of first primers) prior to addition of a second single-stranded RNA containing primer to reduce the concentration of excess first primer as a reaction mixture component, for example, in a procedure in which the first primer contains RNA sequences that could compete with the second primer for binding at a site to which the second primer is designed to hybridize.

An excess of a first primer could be removed from a reaction mixture by purification or separation of the reaction product from the primer (or primers) prior to incubation with the second primer. However, such a step is cumbersome and may increase variability in an amplification procedure. An "add and incubate" protocol is more advantageous and highly desirable for automation of the process. The methods of the invention do not require purification of a primer extension product from a single-stranded RNA-containing primer. According to the methods of the invention, an enzyme capable of degrading single-stranded RNA may be added to the primer extension reaction mixture for degradation of the primer prior to addition of a second primer. In the event that it is desirable to remove other competing or inhibitory components of the previous reaction prior to amplification, the removal of such other components may be achieved with various purification methods, which are well known in the art.

A major advantage afforded by the use of primers that contain an RNA portion, in addition to their utility in the isothermal amplification schemes described herein, is their unique susceptibility to RNA degrading enzymes which specifically recognize RNA sequences when free or hybridized to RNA or DNA complementary sequences. RNase H, which specifically degrades RNA sequences in an RNA/DNA heteroduplex, is employed in isothermal amplification methods described herein, i.e., DNA and RNA isothermal amplification methods employing chimeric DNA/RNA primers. The specific recognition of RNA when hybridized to a complementary DNA sequence ensures the degradation of the RNA in the heteroduplex, for example, with RNase H, without affecting the RNA portion of unhybridized primer. The specific degradation of single-stranded RNA by an enzyme capable of specifically cleaving single-stranded RNA, e.g., RNase I, RNase A, or RNase T, when not hybridized to form a DNA/RNA heteroduplex or an RNA/RNA hybrid, is advantageously used in the methods of the invention to remove or reduce the amount of excess, unhybridized single-stranded RNA containing primer. Often, RNase I is used in the methods of the invention, because it advantageously recognizes all four ribonucleotides, and thus its activity is not limited by sequence considerations. This enzyme is also heat labile and is easily inactivated by heat treatment, i.e., incubation of the reaction mixture at an elevated temperature for a duration known to completely inactivate the enzyme. An added advantage of the use of RNase I for the degradation of the excess single-stranded RNA containing primer is its lack of requirement for specific divalent ions. Thus, RNase I is active within a reaction buffer mixture which is typically employed for the generation of double-stranded cDNA that can be subsequently amplified using a chimeric DNA/RNA amplification primer, DNA polymerase with strand-displacement activity, and RNase H activity.

In an amplification procedure comprising a first composite primer and a second composite primer, wherein the first composite primer comprises an RNA portion and a 3' DNA portion, wherein the second composite primer comprises an RNA portion and a 3' DNA portion, and wherein the second composite primer comprises a sequence that is hybridizable to a polynucleotide comprising a complement of the first composite primer, excess first composite primer can compete with the second composite primer when carried over into an amplification reaction using the second composite primer. This can be relieved by degradation of the RNA portion of the first chimeric primer prior to addition of the second composite primer to the reaction mixture. In an amplification procedure as described herein in which a first composite primer is used to generate a double-stranded cDNA with a RNA/DNA heteroduplex at one end, the RNA incorporated into the heteroduplex is not susceptible to degradation with an enzyme that specifically cleaves single-stranded RNA, such as RNase I. The remaining chimeric primer that was not consumed in the primer extension reaction is free in solution and its single-stranded 5'-RNA portion is susceptible degradation by RNase I, or another enzyme with single-stranded RNA specificity. Thus, the RNA portion of the remaining free first chimeric primer (or primers) can be degraded by incubation of the reaction mixture with RNase I.

In another embodiment of the invention, primer and RNA may be cleaned up following preparation of double stranded cDNA with a single stranded DNA at the 3'-end of the second strand cDNA. Preparation and utility of these partial duplexes have been previously described (U.S. Patent Application No. 2003/0215926). Treatment of the reaction mixture with one or more RNase enzyme specific for single-stranded RNA, e.g., RNase I, achieves both removal of remaining primer(s) and the RNA target. Both free primer(s) and RNA may interfere with subsequent applications. The potential interference by the remaining free primer(s) is based on competition for binding to the 3'-end single-stranded DNA sequence of the partial duplex.

In a further embodiment of the invention, an enzyme that specifically cleaves single-stranded RNA, such as RNase I, may also be used for cleavage of the remaining ribose residues at the 5' end of RNA in an RNA/DNA heteroduplex after cleavage with an enzyme that cleaves RNA in such a heteroduplex, such as RNase H, in a single primer isothermal amplification procedure, such as the procedure described in U.S. Pat. Nos. 6,251,639 and 6,692,918. It is well known that not all ribose residues of an RNA sequence are degraded by RNase H, when hybridized to a complementary DNA sequence. Thus, amplification products generated by the method utilizing a chimeric DNA/RNA primer, DNA polymerase with strand-displacement activity and RNase H, may include one or more ribose residue(s) at the 5'-end, which were incorporated with the partially hydrolyzed primer. Treatment of the amplification products by incubation with an enzyme capable of cleaving single-stranded RNA, such as RNase I, will advantageously remove residual ribose residues from the 5'-end to generate amplification products with a defined 5'-end sequence. This is particularly important when using the amplification methods described herein to produce amplification products for sequencing, where the sequencing ladders are better resolved when the 5' ends of the products are well defined.

General Techniques

The practice of the invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular CloningA Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., eds., 1994).

Primers, oligonucleotides and polynucleotides employed in the invention can be generated using standard techniques known in the art.

Definitions

A "template," "template strand," "template polynucleotide," "template DNA," "target sequence," "target nucleic acid," or "target DNA," "target polynucleotide," "template RNA," or "target RNA," as used herein, is a polynucleotide for which amplification is desired. The template polynucleotide can comprise DNA or RNA. The template sequence may be known or not known, in terms of its actual sequence. Generally, the terms "target," "template," and variations thereof, are used interchangeably.

"Amplification," or "amplifying," as used herein, generally refers to the process of producing multiple copies of a desired sequence or its complement. "Multiple copies" means at least 2 copies. A "copy" does not necessarily mean perfect sequence complementarity or identity to the template sequence. For example, copies can include nucleotide analogs such as deoxyinosine, intentional sequence alterations (such as sequence alterations introduced through a primer comprising a sequence that is hybridizable, but not complementary, to the template, or a non-target sequence introduced through a primer), and/or sequence errors that occur during amplification. "Amplifying" a sequence may generally refer to making copies of a sequence or its complement, with the understanding that, as stated above, copying does not necessarily mean perfect sequence complementarity or identity with respect to the template sequence.

"Polynucleotide," or "nucleic acid," as used interchangeably herein, refers to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine,
psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s).
Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping groups moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, a-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(0)S("thioate"), P(S)S ("dithioate"), "(0)NR2 ("amidate"), P(0)R, P(0) OR', CO or $CH_2$ ("formacetal"), in which each R or R' is independently H or substituted or unsubstituted alkyl (1-20 C) optionally containing an ether (-0-) linkage, aryl, alkenyl, cycloalkyl, cycloalkenyl or araldyl. Not all linkages in a polynucleotide need be identical. The preceding description applies to all polynucleotides referred to herein, including RNA and DNA.
A "labeled dNTP," or "labeled rNTP," as used herein, refers, respectively, to a dNTP or rNTP, or analogs thereof, that is directly or indirectly attached with a label. For example, a "labeled" dNTP or rNTP, may be directly labeled with, for example, a dye and/or a detectable moiety, such as a member of a specific binding pair (such as biotinavidin). A "labeled" dNTP or rNTP, may also be indirectly labeled by its attachment to, for example, a moiety to which a label is/can be attached. A dNTP or rNTP, may comprise a moiety (for example, an amine group) to which a label may be attached following incorporation of the dNTP or rNTP into an extension product. Useful labels in the present invention include fluorescent dyes (e.g., fluorescein isothiocyanate, Texas red, rhodamine, green fluorescent protein and the like), radioisotopes (e.g., $^3H$, $^{35}S$, $^{32}P$, $^{33}P$, $^{125}I$, or $^{14}C$), enzymes (e.g., LacZ, horseradish peroxidase, alkaline phosphatase,), digoxigenin, and colorimetric labels such as colloidal gold or colored glass or plastic (e.g., polystyrene, polypropylene, latex, etc.) beads. Various anti-ligands and ligands can be used (as labels themselves or as a means for attaching a label).

In the case of a ligand that has a natural anti-ligand, such as biotin, thyroxine and cortisol, the ligand can be used in conjunction with labeled anti-ligands.
The "type" of dNTP or rNTP, as used herein, refers to the particular base of a nucleotide, namely adenine, cytosine, thymine, uridine, or guanine
"Nucleotide terminator," "polynucleotide chain terminator," "chain terminator" or "terminator" used herein refers to a nucleotide that when incorporated into a primer extension product prevents the further extension of such primer extension product. When the nucleotide terminator includes a ribofuranose sugar, the 3'-position must not have a hydroxyl group capable of being utilized by a polymerase enzyme to incorporate additional nucleotides. Examples of such nucleotide terminators include dideoxyadenosine triphoshate (ddATP), dideoxycytosine triphosphate (ddCTP), dideoxyguanosine triphosphate (ddGTP), dideoxythymidine triphosphate (ddTTP), and dideoxyuridine triphosphate (ddUTP). Alternatively, a ribofuranose analog may be used, such as arabinose. Reversible nucleotide terminators and acyclic terminators also may be used A "labeled" nucleotide terminator includes a detectable label, as described above.
"Oligonucleotide," as used herein, generally refers to short, generally single stranded, generally synthetic polynucleotides that are generally, but not necessarily, less than about 200 nucleotides in length. Oligonucleotides in the invention include composite primers and auxiliary primers. The terms "oligonucleotide" and "polynucleotide" are not mutually exclusive. The description above for polynucleotides is equally and fully applicable to oligonucleotides.
A "primer," as used herein, refers to a nucleotide sequence, generally with a free 3'-OH group, that hybridizes with a template sequence (such as a target polynucleotide, target DNA, or a primer extension product) and is capable of promoting polymerization of a polynucleotide complementary to the template. A "primer" can be, for example, an oligonucleotide.
To "inhibit" is to decrease or reduce an activity, function, and/or amount as compared to a reference.
A "random primer," as used herein, is a primer that comprises a sequence that is designed not necessarily based on a particular or specific sequence in a sample, but rather iexpectation (or an empirical observation) that the sequence of the random primer is hybridizable (under a given set of conditions) to one or more sequences in the sample. The sequence of a random primer (or its complement) may or may not be naturally-occurring, or may or may not be present in a pool of sequences in a sample of interest. The amplification of a plurality of nucleic acid species in a single reaction mixture would generally, but not necessarily, employ a multiplicity, preferably a large multiplicity, of random primers. As is well understood in the art, a "random primer" can also refer to a primer that is a member of a population of primers (a plurality of random primer) which collectively are designed to hybridize to a desired and/or a significant number of target sequences. A random primer may hybridize at a plurality of sites on a nucleic acid sequence. The use of random primers provides a method for generating primer extension products complementary to a target polynucleotide which does not require prior knowledge of the exact sequence of the target. Random primers may comprise a random sequence at the 3' end, but are not limited to 3' random sequences.
An "arbitrary primer" refers to a primer that hybridizes to a multiplicity of target sequences. The arbitrary hybridization of such a primer to target sequences may be achieved via partial complementarity to a multiplicity of sequences along the polynucleotide target.

"Protopromoter sequence," and "propromoter sequence," as used herein, refer to a single-stranded DNA sequence region which, in double-stranded form is capable of mediating RNA transcription. In some contexts, "protopromoter sequence," "protopromoter," "propromoter sequence," "propromoter," "promoter sequence," and "promoter" are used interchangeably.

A "propromoter polynucleotide," as used herein, refers to a polynucleotide comprising a propromoter sequence. Example of a propromoter polynucleotide is a propromoter template oligonucleotide (PTO).

"Propromoter template oligonucleotide (PTO)" and "promoter template oligonucleotide (PTO)" as used herein, refer to an oligonucleotide that comprises a propromoter sequence and a portion, generally a 3' portion, that is hybridizable (under a given set of conditions) to the 3' region of a primer extension product. The propromoter sequence and the hybridizable portion may be the same, distinct or overlapping nucleotides of an oligonucleotide.

As used herein, "complex comprising an RNA/DNA partial heteroduplex" generally refers to a population of intermediate complexes that generally includes (a) copies of template polynucleotide and/or copies of the complement of template polynucleotide sequence appended to composite primer sequences; and (b) copies of template polynucleotide and/or copies of the complement of template polynucleotide appended to the complement of composite primer sequences. By virtue of the presence of composite primer sequence in the intermediate complexes, the complexes comprise at least a RNA/DNA partial heteroduplex. The RNA portion of the partial heteroduplex generally is introduced (via extension) by the RNA portion of the composite primer, and the DNA portion of the partial heteroduplex comprises the complement of the RNA portion of the composite primer. As discussed herein, the complex comprising an RNA/DNA partial heteroduplex functions as a substrate for further amplification during the single primer isothermal amplification phase of the methods. Generally, RNA in the RNA/DNA partial heteroduplex is cleaved, generating a 3' single stranded portion with sequences that are complementary to RNA in a composite amplification primer (and thus forming a binding site for a composite amplification primer). Thus, reference to "a complex comprising a 3' single stranded portion" generally refers to the complex comprising an RNA/DNA partial heteroduplex when its RNA is cleaved.

A "complex" is an assembly of components. A complex may or may not be stable and may be directly or indirectly detected. For example, as is described herein, given certain components of a reaction, and the type of product(s) of the reaction, existence of a complex can be inferred. For purposes of this invention, a complex is generally an intermediate with respect to the final amplification product(s). An example of a complex is a complex of composite primer extension product and second composite primer extension product, as described herein.

A "portion" or "region," used interchangeably herein, of a polynucleotide or oligonucleotide is a contiguous sequence of 2 or more bases. In other embodiments, a region or portion is at least about any of 3, 5, 10, 15, 20, 25 or more contiguous nucleotides.

A region, portion, or sequence which is "adjacent" to another sequence directly abuts that region, portion, or sequence. For example, an RNA portion which is adjacent to a 5' DNA portion of a composite primer directly abuts that region.

A "reaction mixture" is an assemblage of components, which, under suitable conditions, react to form a complex (which may be an intermediate) and/or a product(s).

"A", "an" and "the", and the like, unless otherwise indicated include plural forms. "A" fragment means one or more fragments.

Conditions that "allow" an event to occur or conditions that are "suitable" for an event to occur, such as hybridization, strand extension, and the like, or "suitable" conditions are conditions that do not prevent such events from occurring. Thus, these conditions permit, enhance, facilitate, and/or are conducive to the event. Such conditions, known in the art and described herein, depend upon, for example, the nature of the nucleotide sequence, temperature, and buffer conditions. These conditions also depend on what event is desired, such as hybridization, cleavage, and/or strand extension.

Sequence "mutation," as used herein, refers to any sequence alteration in a sequence of interest in comparison to a reference sequence. A reference sequence can be a wild type sequence or a sequence to which one wishes to compare a sequence of interest. A sequence mutation includes single nucleotide changes, or alterations of more than one nucleotide in a sequence, due to mechanisms such as substitution, transversion, deletion or insertion. Single nucleotide polymorphism (SNP) is also a sequence mutation as used herein.

"Microarray" and "array," as used interchangeably herein, comprise a surface with an array, preferably ordered array, of putative binding (e.g., by hybridization) sites for a biochemical sample (target) which often has undetermined characteristics. In a preferred embodiment, a microarray refers to an assembly of distinct polynucleotide or oligonucleotide probes immobilized at defined locations on a substrate. Arrays are formed on substrates fabricated with materials such as paper, glass, plastic (e.g., polypropylene, nylon, polystyrene), polyacrylamide, nitrocellulose, silicon, optical fiber or any other suitable solid or semi-solid support, and configured in a planar (e.g., glass plates, silicon chips) or three-dimensional (e.g., pins, fibers, beads, particles, microtiter wells, capillaries) configuration. Probes forming the arrays may be attached to the substrate by any number of ways including (i) in situ synthesis (e.g., high-density oligonucleotide arrays) using photolithographic techniques (see, Fodor et al., *Science* (1991), 251:767-773; Pease et al., *Proc. Natl. Acad. Sci. U.S.A.* (1994), 91:5022-5026; Lockhart et al., *Nature Biotechnology* (1996), 14:1675; U.S. Pat. Nos. 5,578, 832; 5,556,752; and 5,510,270); (ii) spotting/printing at medium to low-density (e.g., cDNA probes) on glass, nylon or nitrocellulose (Schena et al, *Science* (1995), 270:467-470, DeRisi et al, *Nature Genetics* (1996), 14:457-460; Shalon et al., *Genome Res.* (1996), 6:639-645; and Schena et al., *Proc. Natl. Acad. Sci. U.S.A.* (1995), 93:10539-11286); (iii) by masking (Maskos and Southern, *Nuc. Acids. Res.* (1992), 20:1679-1684) and (iv) by dot-blotting on a nylon or nitrocellulose hybridization membrane (see, e.g., Sambrook et al., Eds., 1989, Molecular Cloning: A Laboratory Manual, 2nd ed., Vol. 1-3, Cold Spring Harbor Laboratory (Cold Spring Harbor, N.Y.)). Probes may also be noncovalently immobilized on the substrate by hybridization to anchors, by means of magnetic beads, or in a fluid phase such as in microtiter wells or capillaries. The probe molecules are generally nucleic acids such as DNA, RNA, PNA, and cDNA but may also include proteins, polypeptides, oligosaccharides, cells, tissues and any permutations thereof which can specifically bind the target molecules.

The term "3'" generally refers to a region or position in a polynucleotide or oligonucleotide 3' (downstream) from another region or position in the same polynucleotide or oligonucleotide.

The term "5'" generally refers to a region or position in a polynucleotide or oligonucleotide 5' (upstream) from another region or position in the same polynucleotide or oligonucleotide.

The term "3'-DNA portion," "3'-DNA region," "3'-RNA portion," and "3'-RNA region," refer to the portion or region of a polynucleotide or oligonucleotide located towards the 3' end of the polynucleotide or oligonucleotide, and may or may not include the 3' most nucleotide(s) or moieties attached to the 3' most nucleotide of the same polynucleotide or oligonucleotide. The 3' most nucleotide(s) can be preferably from about 1 to about 50, more preferably from about 10 to about 40, even more preferably from about 20 to about 30 nucleotides.

The term "5'-DNA portion," "5'-DNA region," "5'-RNA portion," and "5'-RNA region," refer to the portion or region of a polynucleotide or oligonucleotide located towards the 5' end of the polynucleotide or oligonucleotide, and may or may not include the 5' most nucleotide(s) or moieties attached to the 5' most nucleotide of the same polynucleotide or oligonucleotide. The 5' most nucleotide(s) can be preferably from about 1 to about 50, more preferably from about 10 to about 40, even more preferably from about 20 to about 30 nucleotides.

"Absent" or "absence" of product, and "lack of detection of product" as used herein includes insignificant, or de ininimus levels, generally due to lack of significant accumulation of product.

Amplification Methods of the Invention

The following are examples of the nucleic acid amplification methods of the invention. It is understood that various other embodiments may be practiced, given the general description provided above. For example, reference to using a composite primer means that any of the composite primers described herein may be used.

In one embodiment, the invention provides nucleic acid amplification methods in which an RNA/DNA composite primer is used. In some embodiments, the method includes global amplification using a composite primer that is capable of binding to multiple sites within a template polynucleotide, including DNA and RNA template polynucleotides. In some embodiments, the method includes amplification of mRNA using a composite primer containing a 3' poly-dT sequence. In some embodiments, the method includes amplification of a nucleic acid template with a composite primer containing at least one random nucleotide at the 3' end or an arbitrary nucleotide sequence. In some embodiments, a multiplicity of first primers is used. In some embodiments, the first primer is a tailed primer comprising a 5' portion which is not hybridizable to the template under conditions in which the first primer hybridizes to the template.

Generally, the methods of the invention involve two phases: (a) hybridization of a first primer to a polynucleotide target sequence, wherein the first primer is a composite primer comprising an RNA portion and a 3' DNA portion, primer extension to form a first primer extension product, and extension of a second primer to form a second primer extension product, whereby a complex comprising the first and second extension products in an RNA/DNA partial heteroduplex is generated; and (b) composite-primer dependent single primer isothermal amplification using a composite amplification primer which comprises a sequence that is hybridizable to a polynucleotide comprising a complement of the first composite primer, wherein the composite amplification primer comprises an RNA portion and a 3' DNA portion. In the methods of the invention, an enzyme capable of cleaving single-stranded RNA is added to remove or reduce the amount of excess first composite primer which was not incorporated into the first primer extension product and subsequently into the partial heteroduplex of first and second primer extension products, before addition of the composite amplification primer.

Formation of a Complex of First and Second Primer Extension Products

Using the first primer extension product as a template, a second primer extension product complementary to the first primer extension product is generated by extension of a second primer with a DNA-dependent DNA polymerase along the DNA portion of the first primer extension product, and extension by an RNA-dependent DNA polymerase along the 5' RNA portion of the first primer extension product, generating a double stranded complex comprising a RNA/DNA complex at the end. Generation of second primer extension product may be primed with a second primer comprising a random sequence or may be primed by the 3' end of a different composite primer extension product. In some embodiments, second strand production is primed by exogenous (added) primers and/or by fragments of template RNA (endogenous primers). In some embodiments, second primer extension product is primed with specific exogenous primer(s), which may be composite primer(s) or non-composite primer(s).

Incubation with an Enzyme Capable of Cleaving Single-Stranded RNA

RNA sequences of unhybridized first primer are degraded by incubation of a reaction mixture containing complexes of first and second primer extension products and excess first primer, with an enzyme capable of cleaving single-stranded RNA, such as RNase I. The enzyme is inactivated or removed from the reaction mixture prior to addition of a second composite primer for amplification. Single primer isothermal amplification using a complex comprising an RNA/DNA partial heteroduplex as a template In a further phase of the methods, after cleavage of RNA of the first primer with an enzyme capable of cleaving single-stranded RNA and inactivation or removal of the enzyme, the complex comprising an RNA/DNA partial heteroduplex is a substrate for amplification using a single primer isothermal amplification procedure as follows: An enzyme which cleaves RNA sequence from an RNA/DNA hybrid (such as RNase H) cleaves RNA from the partial heteroduplex of first and second primer extension products, leaving a partially double stranded polynucleotide complex comprising a 3' single stranded DNA sequence. The 3' single stranded sequence (formed by cleavage of RNA in the complex comprising an RNA/DNA partial heteroduplex) is generally the complement of the RNA sequence in the first composite primer, and thus forms a specific binding site for a composite amplification primer (which may or may not be the same as the first composite primer, i.e., the first primer and the composite amplification primer may be the same or different). In some embodiments, the first primer comprises a random sequence in the 3' DNA portion, and the composite amplification primer does not comprise the random sequence. In some embodiments, the composite amplification primer comprises a shorter total polynucleotide sequence length than the first primer, for example, a shorter length 3' DNA portion. In some embodiments, the composite amplification primer comprises a sequence that is the same as the RNA portion of the first composite primer. In some embodiments, a plurality of first composite primers are used wherein the RNA portions of the first composite primers are identical and the DNA portions of the first composite primers comprise different sequences.

Extension of a bound composite amplification primer by a DNA-dependent DNA polymerase with strand displacement activity produces a primer extension product, which displaces the previously bound cleaved primer extension product, whereby polynucleotide (generally, DNA) product accumulates. See, for example, U.S. Pat. Nos. 6,251,639, 6,692,918, and 6,946,251.

Amplification using a complex comprising an RNA/DNA partial heteroduplex as a template for further amplification (also termed single primer isothermal amplification) generally occurs under conditions permitting composite amplification primer hybridization, primer extension, cleavage of RNA from an RNA/DNA hybrid and strand displacement. Insofar as the composite primer hybridizes to the 3' single stranded portion (of the partially double stranded polynucleotide which is formed by cleaving RNA in the complex comprising an RNA/DNA partial heteroduplex) comprising, generally, the complement of at least a portion of the composite primer sequence, composite primer hybridization may be under conditions permitting specific hybridization. Thus, in some embodiments, the reaction conditions permit stringent hybridization (i.e., hybridization of sequences that are generally complementary). As is evident from the description herein, in other embodiments, the reaction conditions are less stringent (i.e., permit hybridization of sequences that are less than fully complementary).

Generally, the methods of the invention result in amplification of a multiplicity, a large multiplicity, or a very large multiplicity of template polynucleotide sequences. In some embodiments, essentially all of the template polynucleotide present in the initial sample (e.g., all of the mRNA or all of the genomic DNA) is amplified. In other embodiments, at least 50, at least 100, at least 200, at least 300, or more distinct sequences (such as a gene or other subsegment of a polynucleotide, a marker (such as a SNP or other polymorphism) are amplified, and assessed, e.g., by analysis of marker sequences known to be present in the template sample under analysis, using methods known in the art.

Template polynucleotide sequences that are amplified may be present on the same polynucleotide (e.g., a chromosomes or portion of a chromosome for genomic DNA template or on the same RNA for RNA template) or on different template polynucleotides (e.g., different chromosome or portions of chromosomes for DNA template, or different RNAs for RNA template). In some embodiments, the template polynucleotide sequences that are amplified comprise a multiplicity of target polynucleotides representing non-related nucleic acid sequences, such as mixtures of bacterial or viral DNA or RNA targets.

For convenience, reference is made to a polynucleotide product. In some embodiments, amplified product is a mixture of sense and antisense copies of a given template polynucleotide. For example, if the template polynucleotide is double stranded DNA, the amplification product will correspond to each strand. If the template polynucleotide is single stranded (e.g., RNA or single stranded DNA), amplification product may be produced that is the copy of template polynucleotide (sense copy) and the complement of the template polynucleotide (antisense copy). In the case of global amplification of genomic DNA employing arbitrary primer(s), amplification to produce copies of both strands of the genomic targets is expected. The amplification product of different senses can be annealed to form a double stranded (or partially double stranded) complex, or can be prevented from annealing (or subsequently denatured) to produce a mixture of single stranded amplification products. The amplified products may be of differing lengths.

As illustrated in these embodiments, the methods of the invention are composite-primer dependent (i.e., amplification is not observed in the absence of the composite primer) and all steps are isothermal (in the sense that thermal cycling is not required), although the temperatures for each of the steps may or may not be the same. It is understood that various other embodiments may be practiced, given the general description provided above. For example, as described and exemplified herein, certain steps may be performed as temperature is changed (e.g., raised, or lowered).

Amplification of RNA Sequences

In one aspect, the invention provides methods for amplification of a single RNA species or a pool of RNA species. Some methods provide for generation of multiple copies of DNA comprising sequences complementary to an RNA sequence of interest. Other methods provide for generation of multiple copies of an RNA sequence of interest. These methods are suitable for, for example, generation of cDNA libraries and subtractive hybridization probes. Single stranded DNA or RNA products are generated, which are readily suitable for a variety of uses including expression profiling, e.g., by multiplex analysis by microarray technologies, as well as electrophoresis-based technologies such as differential display. The methods are amenable to automation and do not require thermal cycling.

The methods of the invention are directed to the amplification of one or more species of RNA, such as a pool of RNA sequences, and are especially suitable for the amplification of all RNA (such as mRNA or the whole transcriptome) sequences in a preparation of total RNA from a biological sample. Thus, one of the major advantages of the methods of the invention is the ability to amplify an entire pool of sequences, which is essential for the ability to analyze the gene expression profile in cells, such as the cells in a biological sample of interest. The methods of the invention may also be used to amplify a specific RNA sequence of interest, or a multiplicity of RNAs, for example, members of a family of related RNAs. The methods of the invention also are suitable for amplifying a large multiplicity, and most preferably all RNA (such as mRNA) sequences in a sample.

Insofar as many mRNAs have a unique poly-A 3'-end, amplification initiated from the 3'-end sequence of mRNAs is commonly performed for preparation of cDNA libraries and subsequent sequence analysis for determination of gene expression profiling or other applications. The methods of the invention are similarly suited for preparation of libraries of amplified 3'-portions of mRNAs. A composite primer used in the methods of invention can be designed to be hybridizable to a multiplicity, or all, of the RNA or all mRNA species in the sample by using a composite primer comprising random sequences, according to methods known in the art. Alternatively, if a selected RNA or family of related RNAs are to be amplified, the composite primer will comprise sequence(s) hybridizable to the selected RNA or family of related RNAs.

The methods generally comprise using specially-designed primers, generally one or more RNA/DNA composite primers, to generate a complex of first and second strand cDNAs that comprise a portion with a particular characteristic (e.g., cleavable by an enzyme). As used herein, it is understood that "_cDNA" refers to a polynucleotide primer extension product. Generally, the complex comprises an RNA/DNA heteroduplex at an end of the double stranded cDNA complex. The RNA/DNA heteroduplex at an end of the double stranded cDNA complex may comprise a defined end sequence, generally introduced by the RNA portion of the composite primer. The composite primer according to the methods of the invention comprises a 3'-DNA portion that generally is designed to be hybridizable to a target RNA(s). The remaining portion(s) (such as the 5' RNA portion) of the composite primer generally, but not necessarily, comprises a sequence that is not hybridizable to a target RNA (which would constitute a tail when the primer is bound to a target RNA). Thus, and as the description herein makes clear, reference to a primer that hybridizes to a sequence (or hybridization template) encompasses embodiments in which at least a portion of the primer is hybridized, as well as those embodiments in which an entire primer is hybridized.

After production of a complex of first and second primer extension products, the reaction mixture containing the complex and excess first primer, if any, is contacted with an enzyme capable of cleaving single-stranded RNA. In one embodiment, the enzyme is RNase I. The enzyme capable of cleaving single-stranded RNA is inactivated or removed prior to addition of a composite amplification primer. In one embodiment, the enzyme is inactivated by heat.

The double stranded cDNA complex is a substrate for linear amplification as follows: An enzyme which cleaves RNA from an RNA/DNA hybrid (such as RNase H) cleaves RNA sequence from the hybrid, leaving a 3' DNA sequence on the second strand cDNA available for binding by a composite amplification primer which may or may not be the same as the first composite primer. Extension of a bound composite amplification primer by DNA polymerase with strand displacement activity produces a primer extension product, which displaces the previously bound cleaved first primer extension product, whereby single stranded DNA product accumulates. The single stranded DNA product is a copy of the complement of the target RNA (or "antisense" DNA). This linear amplification is described in Kurn et al., U.S. Pat. Nos. 6,251,639, 6,692,918, and 6,946,251.

In one aspect, the invention works as follows: A composite RNA/DNA primer forms the basis for replication of the template RNA The composite primer (also referred to herein as "first composite primer" or "first primer") hybridizes to template RNA which comprises the RNA sequence(s) of interest, and the composite primer is extended by an RNA-dependent DNA polymerase to form a first primer extension product (interchangeably called "composite primer extension product", or "first-strand cDNA"). After cleavage of the template RNA, a second primer extension product (interchangeably called "second-strand cDNA") is formed (as described below) in a complex with the first primer extension product. The complex of first and second primer extension products is composed of an RNA/DNA hybrid at one end due to the presence of the composite primer in the first primer extension product. An agent such as an enzyme which cleaves RNA from an RNA/DNA hybrid (such as RNase H) cleaves RNA sequence from the hybrid, leaving a sequence on the second primer extension product available for binding by another composite primer (also referred to as "second composite primer" or "composite amplification primer" herein), which may comprise a sequence that is hybridizable to a polynucleotide comprising a complement of the first composite primer. Prior to addition of the composite amplification primer, excess first composite primer (i.e., unhybridized and unincorporated into first primer extension product) is degraded by an enzyme capable of cleaving single-stranded RNA, and the enzyme capable of cleaving single-stranded RNA is then inactivated or removed. The composite amplification primer hybridizes to the single-stranded DNA sequence produced by treatment of the complex of first and second extension products with the agent which cleaves RNA from an RNA/DNA hybrid (e.g., RNase H), and is extended with a DNA polymerase having strand displacement activity, which displaces the previously bound cleaved first primer extension product, resulting in displaced cleaved first primer extension product.

In some embodiments of the invention, the second primer extension product is formed as follows: Following cleavage of the RNA template, a second primer is then hybridized to the first primer extension product and extended to form a second primer extension product in a complex with the first primer extension product. The complex of first and second primer extension products is composed of an RNA/DNA hybrid at one end due to the presence of the composite primer in the first primer extension product. The second primer is any sequence that is hybridizable to the first DNA strand such that it is capable of being extended by a DNA polymerase along a first primer extension product to create a second primer extension product. Thus, in some embodiments, the second primer is an oligonucleotide, which may or may not comprise a random sequence (i.e., a sequence designed to be hybridizable (under a given set of conditions) to one or more sequences in the sample). In other embodiments, the second primer comprises a sequence of the first DNA strand (generally at the 3' end) that is hybridized to a sequence in the first DNA strand (for example, a hairpin or self-annealed structure).

In another aspect of the amplification methods, one or more fragments of the target RNA serves as the primer of the second primer extension product. The target RNA in the initial complex comprising the target RNA and first primer extension product is cleaved with an agent (such as RNase H or heat) such that at least one fragment of the template RNA remains hybridized to the first primer extension product. In this aspect of the invention, one (or more) template RNA fragments(s) serves as a second "primer" in the manner described above, to generate a fragment extension product which has the same function as the second primer extension product in the amplification methods described above. A suitable RNA fragment in the methods of the invention is long enough such that it does not dissociate from the first strand cDNA, preferably from about 3 to about 30, more preferably from about 5 to about 25, even more preferably from about 10 to about 20, and most preferably from about 12 to about 17, nucleotides in length.

In embodiments involving transcription (referred to herein as "enhanced" methods), the second primer may further comprise a sequence such that displaced first primer extension products (other than the very first composite primer extension product) contain a sequence to which a polynucleotide comprising a propromoter (also referred to herein as "propromoter polynucleotide") is capable of hybridizing. Hybridization of the propromoter polynucleotide to a displaced primer extension product and extension of the 3' end of the displaced first primer extension product (if there is an overhang) results in a double stranded promoter region that drives transcription (via DNA-dependent RNA polymerase) to produce sense RNA products. This "enhanced" approach is described in Kurn et al., U.S. Pat. Nos. 6,251,639, 6,692,918, and 6,946, 251.

Accordingly, the invention provides methods of producing at least one copy of a polynucleotide sequence complementary to an RNA sequence of interest comprising combining and reacting the following: (a) a target RNA comprising an RNA sequence of interest; (b) a first (composite) primer comprising an RNA portion and a 3' DNA portion;

(c) a second primer that is hybridizable to an extension product of the composite primer;
(d) an RNA-dependent DNA polymerase; and (e) a DNA-dependent DNA polymerase; whereby a complex of first and second primer extension products is produced. The reaction mixture comprising the complexes of first and second primer extension products and excess first primer, if any, is contacted with an enzyme capable of cleaving single stranded RNA to reduce or remove single-stranded RNA of the first primer. The enzyme capable of cleaving single stranded RNA is then inactivated or removed from the reaction mixture. The following are then combined and reacted: (f) an enzyme that cleaves RNA from an RNA/DNA hybrid; (g) deoxyribonucleoside triphosphates or suitable analogs (which may or may not be labeled); (h) a composite amplification primer comprising an RNA portion and a 3' DNA portion; and (i) a DNA polymerase with strand displacement activity. This combination is subjected to suitable conditions for composite amplification primer hybridization, extension of the primer, RNA cleavage, and displacement of the first primer extension product, wherein RNA from the first composite primer is cleaved and a composite amplification primer binds in the site vacated by the cleaved RNA.

In embodiments that include transcription (i.e., the enhanced methods), the
following are also included in the amplification reaction (either at the same time as the components listed above or added separately): (j) a propromoter polynucleotide comprising a propromoter and a region which hybridizes to an extension product of the first primer (a displaced primer extension product); (k) an RNA polymerase; and (l) ribonucleoside triphosphates or suitable analogs (which may or may not be labeled), in place of (g). In embodiments that include transcription, conditions employed are also suitable for hybridization of the propromoter polynucleotide to the displaced cleaved first primer extension product, extension of the 3' end of the cleaved first primer extension product (if necessary) to generate a double-stranded promoter region, and RNA transcription driven by the promoter.

As described and exemplified herein, the above-described reaction mixtures may be subdivided into two or more different reaction mixtures for separate, generally sequential, incubations that correspond to different aspects of the amplification process.

In some embodiments, the invention provides methods of producing at least one copy of a polynucleotide sequence complementary to an RNA sequence of interest comprising combining and reacting the following: (a) complex of first and second primer
extension products comprising an RNA/DNA heteroduplex at one end, produced as described above, wherein the reaction mixture comprising the complex of first and second extension products and first primer is contacted with an enzyme capable of cleaving single stranded RNA and the enzyme is inactivated or removed prior to contact with a composite amplification primer; (b) a composite amplification primer comprising an RNA portion and a 3' DNA portion; (c) a DNA-dependent DNA polymerase having strand displacement activity; (d) an enzyme that cleaves RNA from an RNA/DNA hybrid; and (e) deoxyribonucleoside triphosphates or suitable analogs (which may or may not be labeled). In embodiments that include transcription, the following are also included in the amplification reaction (either at the same time as the components listed above or added separately): (f) a propromoter polynucleotide comprising a propromoter and a region which hybridizes to an extension product of the first primer (a displaced primer extension product); (g) an RNA polymerase; and (h) ribonucleoside triphosphates or suitable analogs (which may or may not be labeled) in place of (e). The combination is subjected to suitable conditions for composite amplification primer hybridization, extension of the primer, RNA cleavage, and displacement of the first primer extension product wherein its RNA from the in the RNA/DNA heteroduplex of the complex of first and second primer extension products is cleaved and another composite amplification primer binds in the site on the second primer extension product vacated by the cleaved RNA. In embodiments that include transcription, conditions employed are also suitable for hybridization of the propromoter polynucleotide to the displaced first primer extension product, extension of the 3' end of the first primer extension product (if necessary) to generate a double-stranded promoter region, and RNA transcription driven by the promoter.

In another aspect, the invention provides methods of producing single stranded antisense and sense DNA copies of an RNA sequence of interest using a first composite primer, a second composite primer (termed the "reverse composite" primer), and a target RNA fragment. The method involves the following: (a) formation of a double stranded cDNA comprising a RNA-DNA heteroduplex at each end of the double stranded cDNA; and (b) linear amplification of first strand (sense) cDNA and second strand (antisense) cDNA by primer extension from two composite primers and strand displacement. Single stranded first and second strand cDNA product is produced. This product is useful in, e.g., producing cDNA libraries. As is evident, in this aspect of the invention, the second primer extension product is primed by a composite primer.

Use of Enzyme that Cleaves Single Stranded RNA to Cleave Ribose Residues of Amplification Products or Non-Specific Primer Extension Products In one embodiment, the invention provides a method for removing ribose residues from the 5' ends of amplification products. In methods for amplification of a polynucleotide using a double stranded polynucleotide with a heteroduplex at one end and cleavage of the RNA portion of the heteroduplex to provide a binding site for an amplification primer, for example, as described in U.S. Pat. Nos. 6,251,639, 6,692,918, and 6,946,251, the cleavage may be incomplete, resulting in an amplification product comprising one or more ribose residues at the 5' end. An enzyme that cleaves single-stranded RNA may be used to cleave the remaining ribose residues from the 5' end of the amplification products. Treatment of the amplification products with an enzyme capable of cleaving single-stranded RNA, such as RNase I, will advantageously remove the residual ribose residues from the 5' end to generate amplification products with a defined 5' end sequence. This is particularly advantageously for nucleic acid sequencing applications, where the sequencing ladders are better resolved when the 5' ends of the amplification products are well defined, or any other applications which similarly depend on analyzing the amplification products where the size of the amplification products is essential for the analysis.

In another embodiment, the invention provides methods for degrading the 5' RNA portion of non-specific primer extension products. In methods in which a composite primer is used for generation of a primer extension product from a template polynucleotide, undesirable non-specific hybridization of the primer to a polynucleotide template other than the target polynucleotide can occur. For example, the first primer could hybridize to the first primer extension product. Such undesired hybridization, followed by extension by a polymerase, results in formation of a double-stranded polynucleotide with an RNA/DNA hetero duplex at one end and single-stranded RNA at the other end. The single-stranded RNA end could be copied in the downstream amplification steps to form a double-stranded product with a heteroduplex at both ends. These products will serve as amplification substrates and thus lead to generation of undesired amplification products. Treatment with an enzyme that specifically cleaves single-stranded RNA will cleave the single-stranded RNA portion of the undesired first and second primer extension products and prevent the generation of undesired amplification products in the downstream amplification steps.

Thus, the RNA portion of the nonspecifically hybridized primers can be cleaved with an enzyme that cleaves single stranded RNA, minimizing or eliminating the ability of these undesirable products to interfere with the amplification reaction by generating nonspecific amplification products.

Applications

The methods of the invention include methods using the amplified products (so-called "applications"). In some embodiments, the invention provides methods of sequencing polynucleotide sequences. For sequencing methods based on methods described herein wherein the amplified product is DNA, the appropriate dNTPs, or analogs thereof, which may be labeled or unlabeled, are used. For sequencing methods based on methods described herein wherein the amplified product is RNA, the appropriate rNTPs, or analogs thereof which may be labeled or unlabeled, may be used. In some embodiments, a nucleotide terminator, such as a labeled nucleotide terminator, is incorporated during amplification.

In other embodiments, the invention provides methods of detecting nucleic acid sequence mutations. In one embodiment, the amplified products are used to detect and/or identify single strand conformation polymorphisms in a target polynucleotide.

The invention provides methods to characterize (for example, detect presence or absence of and/or quantify) a polynucleotide (e.g., RNA) sequence of interest by generating DNA or RNA products using amplification methods of the invention, and analyzing the products by detection/quantification methods such as those based on array technologies or solution phase technologies. These amplified products may be labeled or unlabeled.

In yet another embodiment, the invention provides methods for immobilizing nucleic acids, including methods for generating microarrays of nucleic acids (DNA or RNA) using amplified products of the amplification methods of the invention.

In another embodiment, the invention provides methods of generating cDNA libraries, methods of generating subtractive hybridization probes, and methods of generating subtractive hybridization libraries.

Various methods for the detection and quantification of gene expression levels are known in the art. For example, microarrays, in which either defined cDNAs or oligonucleotides are immobilized at discrete locations on, for example, solid or semi-solid substrates, or on defined particles, enable the detection and/or quantification of the expression of a multitude of genes in a given specimen.

Using these previously known methods to detect presence of absence of and/or quantify, and analyzing, multiple mRNA species in a sample, which in turn is used as a measure of gene expression profiling, generally requires direct labeling of cDNA, which requires a large amount of input total RNA, in part because mRNA represents only a small subset of the total RNA pool. Thus, when using total RNA preparations, or isolated mRNA, from a given cell or tissue sample, the analysis of gene expression in the sample using methods such as arrays requires a substantial amount of input RNA, which generally ranges from 50 to 200 µg. Similarly, 2 to 5 µg of mRNA purified from a total RNA preparation would generally be required for a single analysis of gene expression profiling using array technologies. This is a clear limitation of methods such as those based on array technology, insofar as the number of cells, or size of tissue specimen required is very large, and these cells or tissue specimens are often scarcely available for testing or are too precious. This limitation is especially severe in the study of clinical specimens, where the cells to be studied are rare and/or difficult to cultivate in vitro, and in high throughput screening of libraries of effector molecules. Also, previous transcription-based methods of amplification of mRNA (described in, for example, Lockhart et al, *Nature Biotechnology* (1996), 14, 1675-1680); van Gelder et al., U.S. Pat. No. 5,716,785), are limited to the amplification efficiency of DNA-dependent RNA polymerases and some of these methods require multiple steps. Moreover, the process by which the polymerase promoter sequence is incorporated is prone to result in non-specific amplification.

The methods of the invention offer the ability to efficiently amplify mRNA under conditions that provide for high specificity of target amplification and which is generally reflective of the distribution in the input RNA. Thus, the utility of the detection/quantification methods which can be used with the amplification products of the invention, such as those based on the powerful array technology, real time PCR, quantitative TaqMan, quantitative PCR using molecular beacons and the like, should be greatly enhanced.

The linear aspect of the amplification methods of the invention significantly increases the specificity of target amplification. Since generation of multiple copies of a sequence of interest is not dependent nor based on cyclical, exponential, amplification of amplification products, the specificity of products obtained is greatly enhanced. The distribution of the various species of amplified products is generally reflective of the distribution in the input polynucleotide, e.g., RNA.

The methods of the invention do not require thermocycling and all of the steps can be performed isothermally, although the various steps may be carried out a different temperatures. This feature provides numerous advantages, including facilitating automation and adaptation for high through-put procedures. The isothermal reaction is faster than that afforded by thermal cycling and is suitable for performing the methods of the invention in miniaturized devices.

The intermediate double stranded cDNA complex comprising an RNA/DNA heteroduplex provides a substrate for linear amplification. Cleavage of the RNA portion of the RNA/DNA heteroduplex permits further amplification without the need to denature the double stranded cDNA intermediate complex. Moreover, since the cleaved double stranded cDNA complex is mostly double stranded, it is less likely that the secondary structure of a single stranded template will interfere with subsequence amplification.

Finally, most of the methods of the invention produce products that are single stranded, thus rendering them more accessible to binding to probes, either in a homogeneous manner, i.e. in solution, or binding to probes immobilized on solid supports. The double stranded products of the methods of the invention are useful for, e.g., production of cDNA libraries.

The ability to efficiently amplify polynucleotides, such as mRNA (or any other desired RNA species or population) under conditions that provides for high specificity of target amplification and which will generally not alter the representation of the various polynucleotide, e.g., mRNA, species in the preparation, will greatly enhance the utility of the detection/quantification methods such as those based on the powerful array technology.

Components and Reaction Conditions Used in the Methods of the Invention

Template Nucleic Acid

The nucleic acid (NA) target to be amplified includes nucleic acids from any source in purified or unpurified form, which can be DNA (dsDNA and ssDNA) or RNA, including tRNA, mRNA, rRNA, mitochondrial DNA and RNA, chloroplast DNA and RNA, DNA-RNA hybrids, or mixtures thereof; genes, chromosomes, plasmids, the genomes of biological material such as microorganisms, e.g., bacteria, yeasts, viruses, viroids, molds, fungi, plants, animals, humans, and fragments thereof. Preferred target polynucleotide includes DNA (e.g., genomic DNA, including human genomic DNA, and mammalian genomic DNA (such as mouse, rat)) and RNA (e.g., mRNA, ribosomal RNA, and total RNA). It should be understood that template RNA includes coding and non-coding RNA. The sequences can be naturally occurring or recombinant nucleic acid targets, including cloned nucleic fragments of interest.

The target nucleic acid can be only a minor fraction of a complex mixture such as a biological sample and can be obtained from various biological material by procedures well known in the art. Nucleic acid can be obtained from sources containing very small quantities of nucleic acid, such a single cell, small numbers of cells, patient samples, forensic samples, and archeological samples. Obtaining and purifying nucleic acids use standard techniques in the art, including methods designed to isolate one or a very small number of cells, such a cell sorting or laser capture micro-dissection. The methods of the invention are particularly suited for use with genomic DNA (e.g., human and other mammalian genomic DNA), as well as RNA (e.g., total RNA or mRNA samples). Amplification of an RNA target may be accomplished by initial cDNA synthesis, as known in the art, followed by amplification from the cDNA template.

The target polynucleotide(s) can be known or unknown and may contain more than one desired specific nucleic acid sequence of interest, each of which may be the same or different from each other. If the target polynucleotide is double stranded (e.g., double stranded DNA or a double stranded DNA/RNA hybrid, such as is produced by first strand cDNA synthesis), the target may first be treated to render it single stranded (e.g., by denaturation or by cleavage of the RNA portion of a DNA/RNA hybrid). Denaturation may also be carried out to remove secondary structure present in a single stranded target molecule (e.g., RNA). In some cases, double stranded DNA target polynucleotide may be first cleaved by one or more restriction endonuclease enzymes.

When the target polynucleotide is double stranded (ds) DNA, the initial step of the amplification of a target nucleic acid sequence may be to render the target single stranded. If the target nucleic acid is a double stranded (ds) DNA, the initial step can be target denaturation, for example, by target denaturation. The denaturation step may be thermal denaturation or any other method known in the art, such as alkali treatment. If the target nucleic acid is present in an DNA-RNA hybrid, the initial step can be denaturation of the hybrid to obtain a DNA, or removal of the RNA strand using other means known in the art, such as thermal treatment, digestion with an enzyme that cleaves RNA from an RNA/DNA hybrid (such as RNase H) or alkali treatment, to generate single stranded DNA. When the target is RNA, the initial step may be the synthesis of a single stranded cDNA. Techniques for the synthesis of cDNA from RNA are known in the art, and include reverse transcription of RNA strand using a primer that binds to a specific target, such as the poly-A tail of eukaryotic mRNAs or other specific or consensus sequences. In addition, reverse transcription can be primed by a population of degenerate or partially degenerate primers. First strand cDNA can be separated from the complex of RNA and first strand cDNA as described herein.

RNAs can be from any source in purified or unpurified form, which can be RNA such as total RNA, tRNA, mRNA, rRNA, mitochondrial RNA, chloroplast RNA, DNA-RNA hybrids, or mixtures thereof, from any source and/or species, including human, animals, plants, and microorganisms such as bacteria, yeasts, viruses, viroids, molds, fungi, plants, and fragments thereof. It is understood that the RNA can be coding or noncoding RNA (such as untranslated small RNAs). RNAs can be obtained and purified using standard techniques in the art. Use of a DNA target (including genomic DNA target) would require initial transcription of the DNA target into RNA form, which can be achieved using methods disclosed in Kurn, U.S. Pat. No. 6,251,639 B1, and by other techniques (such as expression systems) known in the art. Thus, RNA template can be itself generated from a DNA source (such as genomic DNA), using methods known in the art, including Kurn, U.S. Pat. No. 6,251,639. RNA copies of genomic DNA would generally include untranscribed sequences generally not found in mRNA, such as introns, regulatory and control elements, etc. RNA targets may also be generated from cloned genomic DNA sequences that can be subjected to in vitro transcription. Use of a DNA-RNA hybrid would require denaturation of the hybrid to obtain a single stranded RNA, denaturation followed by transcription of the DNA strand to obtain an RNA, or other methods known in the art such as digestion with an RNase H to generate single stranded DNA.

Composite Primer

The methods of the invention generally employ two primers each having at least one single-stranded RNA portion, a first primer that hybridizes to template polynucleotide and is extended with a polymerase to form a primer extension product and an a composite amplification primer. In some embodiments, the primers are composite primers that contain RNA and DNA portions, e.g., an RNA portion and a 3' DNA portion. One or both of the composite primers may comprise a 5' RNA portion and a 3' DNA portion. One or both of the composite primers may comprise a 5' RNA portion that is adjacent to the 3' DNA portion.

In some embodiments, the first primer is a composite primer having partial nucleic acid sequence homology to a multiplicity of genomic DNA sequences, particularly in the 3' sequences of the composite primer, when analyzed using standard nucleic acid comparison algorithms. In some embodiments, the first composite primer contains a random sequence, for example, in the 3' DNA portion. In some embodiments, for example, for amplification of mRNA sequences, the primer is a composite primer having a 3' poly-dT sequence, and optionally containing at least one random nucleotide at the 3'end. In some embodiments, the first primer comprises a multiplicity of different sequences. In some embodiments, the 3' DNA portion of the first primer is a random sequence, for example, a random hexamer, or a longer random sequence, for example, between 5 and 12 nucleotides.

For development of a first primer having partial nucleic acid sequence homology to a multiplicity of genomic DNA sequences, a composite primer sequence can be used as a query sequence in Blast, to search the human genomic DNA database (or other suitable database, such as a mammalian genomic DNA database). Generally, the search is performed using search parameters suitable for identification of partial or "low stringency" alignments, generally the least stringent conditions provided by the program. Such parameters are known in the art and include use of the NCBI Blast program for searching "short, nearly exact matches," with word size=7 (conditions permitting as few as 7 consecutive nucleotide perfect matches at any position in the primer sequence). See, e.g., www ncbi.nlm.nhi.goviblast/Blast.cgi?ALIGNMENTS=50& ALIGNMENT_VIEW= Pairwise&AUTOFOR.MAT=Semiauto&CLIENT=web&DATABASE= nr&DESCRIPTIO NS=100&ENTREZ_QUERY=>(none) &EXPECT=1000&FORMAT_BLOCK_ONRESP AGE=None&FORMAT_ENTREZ_QUERY=(none) &FORMAT_OBJECT=Alignment&F ORMATTYPE=HTML&LAYOUT=TwoWindows& NCBI_GI=on&PAGE=Nucleotides &PROGRAM=blastn&SERVICE=plain&SET DEFAULTS.x=16&SET DEFAULTS.y=8 &SHOW_OVERVIEW=on&WORD_SIZE=7&END_ OF_HTTPGET=Yes. First primers useful in the methods of the invention (i.e., that randomly hybridize to template polynucleotide) generally exhibit high partial homology rate with genomic DNA sequences, for example homology of stretches of 7 nucleotides with about 100 genomic DNA sequences, with about 70% of the hits located at the 3' end of the composite primer. A first primer with a very unique sequence (i.e., low levels of homology with target genomic DNA sequences) did not function efficiently in the methods of the invention when used with genomic DNA template.

As is evident from the discussion above, reference to a primer that binds (hybridizes to) a sequence (or template) encompasses embodiments in which at least a portion of the primer is hybridized, embodiments in which two (or more portions) of the primer are hybridized (separated by unhybridized (looped out) portions of the primer), and embodiments in which the entire primer is hybridized. In certain embodiments, a 5'-portion, commonly the 5'-most portion, of the composite primer is designed such that the particular 5'-portion is not expected to randomly hybridize to template polynucleotide (composite primers of this configuration are referred to as "tailed" primers, in reference to the 'tail' of unhybridized primer). In some embodiments, the tail portion of the composite primer is the entire 5' RNA portion of the composite primer. Thus, according to the methods of the invention, only a portion of the 3'-end of the composite primer must be hybridized in order for initiation of primer extension by DNA polymerase. In some embodiments, for example, only 1, 2, 3, 4, 5, 6, 7 or more nucleotides of the 3' end of the primer must hybridize in order for primer extension to be initiated. It is understood that hybridization of the 3'-most portion of the composite primer may be stabilized to various extents by further hybridization of another portion of the primer (with or without looping out of intervening primer portions). A DNA polymerase can be included during primer hybridization to enhance (e.g., stabilize) hybridization of composite primer by initiation of primer extension, and thus, stabilization of primer hybridization.

Random composite primer hybridization and/or generation of composite primer extension product is promoted by use of conditions designed to permit random (nonspecific) primer hybridization. Such conditions are well known in the art, and are further discussed below, and include: decreased stringency during primer hybridization and/or first strand synthesis (including reduced temperature and/or buffer conditions of reduced stringency, such as reduced ionic strength); composite primer selection and/or design (discussed further herein); composite primer and template concentration, presence or absence of an agent that stabilizes a 3' hybridized primer (such as a DNA polymerase), and presence or absence of agents such as DMSO that lower the temperature requirements for stable hybridization. It is understood that the selection of reaction conditions may be used to control the frequency of composite primer hybridization, and thus control coverage and/or representation of template polynucleotide sequences in amplification product.

Generally, the composite primer is also designed so that there is no primer-dimer formation capability, as determined using software routinely available to one of ordinary skill in the art, e.g. Oligo Primer Analysis Software from Molecular Biology Insight, and references therein. One of skill in the art will understand that other factors affect nucleic acid hybridization affinities. For example, any and all of the guanosine-cytosine content of the primer-target and primer-primer duplexes, minor groove binders, 0-methylation or other modification of nucleotides, temperature, and salt are potentially important factors in constructing primers with the requisite differences in binding energies. Another factor in designing and constructing primers is the free energy parameters of hybridization of given sequences under a given set of hybridization conditions. The free energy parameters for the formation of a given hybrid may be calculated by methods known in the art (see, e.g., Tinoco et al. *Nature* (1973) 246: 40-41 and Freier et al., *Proc. Natl. Acad. Sci. USA* (1986) 83:9373-9377; computer programs, e.g., Oligo Primer Analysis Software from Molecular Biology Insight, and references therein), and it is possible to predict, for a given oligonucleotide template, primer sequences for which the required free energy changes for formation of various complexes will be met.

The composite primers should be extendable by DNA polymerase, i.e., a DNA-dependent DNA polymerase for extension of the primer along a DNA target polynucleotide, or an RNA-dependent DNA polymerase for extension of the primer along an RNA target polynucleotide.

Generation of primers suitable for extension by polymerization is well known in the art, such as described in PCT Pub. No. WO99/42618 (and references cited therein). Generally, the primer should permit high efficiency of amplification of a synthetic target that contains a specific primer target binding site (e.g., the complementary sequence to the primer), for example, permitting amplification of about $10^6$ to $10^9$ using methods described in Kurn, U.S. Pat. No. 6,251,639. The composite amplification primer is designed such that subsequent displacement of the primer extension product by binding of a new (additional) composite primer and the extension of the new primer by the polymerase can be achieved. In addition, cleavage of the RNA portion of the primer extension product leads to generation of amplification product which is not a substrate for amplification by the composite amplification primer. It is understood that, in the following section that generally describes aspects of the composite primers used in the methods of the invention, characteristics described may be applicable to the primers if used for hybridizing and initiating the polynucleotide amplification (production of composite extension product) and/or for single primer amplification as described herein.

In some embodiments, first and second different composite primers are used in the methods of the invention. In some embodiments, the second composite primer comprises a sequence that is hybridizable to a polynucleotide comprising a complement of the first composite primer.

For use in single primer amplification and/or composite primer extension product formation, a composite amplification primer comprises at least one RNA portion that is capable of (a) binding (hybridizing) to a sequence on the single stranded portion of the complex (formed by cleavage of RNA in the complex comprising a RNA/DNA partial heteroduplex) (in some embodiments, on second primer extension product) independent of hybridization of the DNA portion(s) to a sequence on the same single stranded portion; and (b) being cleaved with an agent such as a ribonuclease when hybridized to the single stranded portion. The composite primers bind to the single stranded portion, and are extended by DNA polymerase to form a RNA/DNA partial heteroduplex in which only the RNA portion of the primer is cleaved upon contact with an agent which cleaves RNA in an RNA/DNA hybrid, such as an enzyme, such as a ribonuclease (such as RNase H), while the composite primer extension product remains intact, thus enabling annealing of another composite primer.

When used for the single primer amplification described herein, the composite primers also comprise a 3' DNA portion that is capable of hybridization to a sequence on the 3' single stranded portion of the complex such that its hybridization to the 3' single stranded portion is favored over that of the nucleic acid strand that is displaced from the complex by the DNA polymerase. Such primers can be rationally designed based on well known factors that influence nucleic acid binding affinity, such as sequence length and/or identity, as well as hybridization conditions. In a preferred embodiment, hybridization of the 3' DNA portion of the composite primer to its complementary sequence in the complex (e.g., in the second primer extension product) favored over the hybridization of the homologous sequence in the 5' end of the displaced strand to the composite primer extension product.

The composite primer comprises a combination of RNA and DNA (see definition above), with the 3'-end nucleotide being a nucleotide suitable for nucleic acid extension. The 3'-end nucleotide can be any nucleotide or analog that when present in a primer, is extendable by a DNA polymerase. Generally, the 3'-end nucleotide has a 3'-OH. Suitable primers include those that comprise at least one portion of RNA and at least one portion of DNA. For example, composite primers can comprise a 5'-RNA portion and a 3'-DNA portion (in which the RNA portion is adjacent to the 3'-DNA portion); or 5'- and 3'-DNA portions with an intervening RNA portion. Accordingly, in one embodiment, the composite primer comprises a 5' RNA portion and a 3'-DNA portion, preferably wherein the RNA portion is adjacent to the 3'-DNA portion. In another embodiment, the composite primer comprises 5'- and 3'-DNA portions with at least one intervening RNA portion (i.e., an RNA portion between the two DNA portions). In yet another embodiment, the composite primer of the invention comprises a 3'-DNA portion and at least one intervening RNA portion (i.e., an RNA portion between DNA portions).

The length of an RNA portion in a composite primer comprising a 3'-DNA portion and an RNA portion can be preferably from about 1 to about 50, preferably about 18 to about 30, more preferably from about 3 to about 20, even more preferably from about 4 to about 15, and most preferably from about 5 to about 10 nucleotides. In some embodiments of a composite primer comprising a 3'-DNA portion and an RNA portion, an RNA portion can be at least about any of at least about 1, 3, 4, 5, 10, 15, or 18 nucleotides, with an upper limit of about any of 10, 14, 15, 20, 25, 30, 50 nucleotides. In certain embodiments, the composite primer has an RNA portion of about 5, 10, 15, 20, 25, 30, 35, 40, 45, or 50 nucleotides.

The length of the 5'-RNA portion in a composite primer comprising a 5'-RNA portion and a 3'-DNA portion can be preferably from about 3 to about 50 nucleotides, preferably about 18 to about 30 nucleotides, more preferably from about 5 to about 20 nucleotides, even more preferably from about 7 to about 18 nucleotides, preferably from about 8 to about 17 nucleotides, and most preferably from about 5 to about 50 nucleotides. In other embodiments of a composite primer comprising a 5'-RNA portion and a 3'-DNA portion, the 5'-RNA portion can be at least about any of 3, 5, 7, 8, 10, 15, or 18 nucleotides, with an upper limit of about any of 14, 15, 17, 18, 20, 30, or 50 nucleotides. In certain embodiments, the composite primer has an RNA portion of about 5, 10, 15, 20, 25, 30, 35, 40, 45, or 50 nucleotides.

In embodiments of a composite primer comprising a 5'-RNA portion and a 3'-DNA portion further comprising non-5'-RNA portion(s), a non-5'-RNA portion can be preferably from about 1 to about 7 nucleotides, more preferably from about 2 to about 6 nucleotides, and most preferably from about 3 to about 5 nucleotides. In certain embodiments of a composite primer comprising a 5'-RNA portion and a 3'-DNA portion further comprising non-5'-RNA portion(s), a non-5'-RNA portion can be at least about any of 1, 2, 3, 5, with an upper limit of about any of 5, 6, 7, 10 nucleotides.

In embodiments of a composite primer comprising a 5'-RNA portion and a 3'-DNA portion, in which the 5'-RNA portion is adjacent to the 3'-DNA portion, the length of the 5'-RNA portion can be preferably from about 3 to about 50 nucleotides, about 18 to about 30, more preferably from about 5 to about 20 nucleotides, even more preferably from about 7 to about 18 nucleotides, preferably from about 8 to about 17 nucleotides, and most preferably from about 5 to about 50 nucleotides. In certain embodiments of a composite primer comprising a 5'-RNA portion and a 3'-DNA portion, in which the 5'-RNA portion is adjacent to the 3'-DNA portion, the 5'-RNA portion can be at least about any of 3, 5, 7, 8, 10, 15, or 18 nucleotides, with an upper limit of about any of 14, 15, 17, 18, 20, 30, or 50 nucleotides. In certain embodiments, the composite primer has an RNA portion of about 5, 10, 15, 20, 25, 30, 35, 40, 45, or 50 nucleotides.

The length of an intervening RNA portion in a composite primer comprising 5'- and 3'-DNA portions with at least one intervening RNA portion can be preferably from about 1 to about 7 nucleotides, more preferably from about 2 to about 6 nucleotides, and most preferably from about 3 to about 5 nucleotides. In some embodiments of a composite primer comprising 5'- and 3'-DNA portions with at least one intervening RNA portion, an intervening RNA portion can be at least about any of 1, 2, 3, 5 nucleotides, with an upper limit of about any of 5, 6, 7, 10 nucleotides. The length of an intervening RNA portion in a composite primer comprising a 3'-DNA portion and at least one intervening RNA portion can be preferably from about 1 to about 7 nucleotides, more preferably from about 2 to about 6 nucleotides, and most preferably from about 3 to about 5 nucleotides. In some embodiments of a composite primer comprising a 3'-DNA portion and at least one intervening RNA portion, an intervening RNA portion can be at least about any of 1, 2, 3, 5 nucleotides, with an upper limit of about any of 5, 6, 7, 10 nucleotides. In a composite primer comprising a 3'-DNA portion and at least one intervening RNA portion, further comprising a 5'-RNA portion, the 5'-RNA portion can be preferably from about 3 to about 25 nucleotides, more preferably from about 5 to about 20 nucleotides, even more preferably from about 7 to about 18 nucleotides, preferably from about 8 to about 17 nucleotides, and most preferably from about 10 to about 15 nucleotides. In some embodiments of a composite primer comprising a 3'-DNA portion and at least one intervening RNA portion, further comprising a 5'-RNA portion, the 5'-RNA portion can be at least about any of 3, 5, 7, 8, 10 nucleotides, with an upper limit of about any of 15, 17, 18, 20 nucleotides.

The length of the 3'-DNA portion in a composite primer comprising a 3'-DNA portion and an RNA portion can be preferably from about 1 to about 20, preferably from about 6 to about 12, preferably from about 5 to about 20, more preferably from about 3 to about 18, even more preferably from about 5 to about 15, and most preferably from about 7 to about 12 nucleotides. In some embodiments of a composite primer comprising a 3'-DNA portion and an RNA portion, the 3'-DNA portion can be at least about any of 1, 3, 5, 6, 7, or 10 nucleotides, with an upper limit of about any of 10, 12, 15, 18, 20, 22 nucleotides. In one embodiment, the composite primer has a 3'-DNA portion of 1 nucleotide, or any of about 5, 6, 10, 12, 15, or 20 nucleotides.

The length of the 3'-DNA portion in a composite primer comprising a 5'-RNA portion and a 3'-DNA portion can be preferably from about 1 to about 20 nucleotides, preferably from about 6 to about 12, preferably from about 5 to about 20, more preferably from about 3 to about 18 nucleotides, even more preferably from about 5 to about 15 nucleotides, and most preferably from about 7 to about 12 nucleotides. In some embodiments of a composite primer comprising a 5'-RNA portion and a 3'-DNA portion, the 3' DNA portion can be at least about any of 1, 3, 5, 6, 7, 10 nucleotides, with an upper limit of about any of 10, 12, 15, 18, 20, 22 nucleotides. In one embodiment, the composite primer has a 3'-DNA portion of 1 nucleotide, or any of about 5, 6, 10, 12, 15, or 20 nucleotides.

In embodiments of a composite primer comprising a 5'-RNA portion and a 3'-DNA portion, further comprising non-3'-DNA portion(s), a non-3'-DNA portion can be preferably from about 1 to about 10 nucleotides, more preferably from about 2 to about 8 nucleotides, and most preferably from about 3 to about 6 nucleotides. In some embodiments of a composite primer comprising a 5'-RNA portion and a 3'-DNA portion, further comprising non-3'-DNA portion(s), a non-3'-DNA portion can be at least about any of 1, 2, 3, 5 nucleotides, with an upper limit of about any of 6, 8, 10, 12 nucleotides.

In embodiments of a composite primer comprising a 5'-RNA portion and a 3'-DNA portion in which the 5'-RNA portion is adjacent to the 3'-DNA portion, the length of the 3'-DNA portion can be preferably from about 1 to about 20 nucleotides, preferably from about 6 to about 12, preferably from about 5 to about 20 nucleotides, more preferably from about 3 to about 18 nucleotides, even more preferably from about 5 to about 15 nucleotides, and most preferably from about 7 to about 12 nucleotides. In certain embodiments of the primer comprising a 5'-RNA portion and a 3'-DNA portion in which the 5'-RNA portion is adjacent to the 3'-DNA portion, the 3'-DNA portion can be at least about any of 1, 3, 5, 6, 7, 10 nucleotides, with an upper limit of about any of 10, 12, 15, 18, 20, 22 nucleotides. In one embodiment, the composite primer has a 3'-DNA portion of about 1 nucleotide, or any of about 5, 6, 10, 12, 15, or 20 nucleotides.

The length of a non-3'-DNA portion in a composite primer comprising 5'- and 3'-DNA portions with at least one intervening RNA portion can be preferably from about 1 to about 10 nucleotides, more preferably from about 2 to about 8 nucleotides, and most preferably from about 3 to about 6 nucleotides. In some embodiments of a primer comprising 5'- and 3'-DNA portions with at least one intervening RNA portion, a non-3'DNA portion can be at least about any of 1, 2, 3, 5 nucleotides, with an upper limit of about any of 6, 8, 10, 12 nucleotides.

The length of the 3'-DNA portion in a composite primer comprising 5'- and 3'-DNA portions with at least one intervening RNA portion can be preferably from about 1 to about 20 nucleotides, more preferably from about 3 to about 18 nucleotides, even more preferably from about 5 to about 15 nucleotides, and most preferably from about 7 to about 12 nucleotides. In some embodiments of a composite primer comprising 5'- and 3'-DNA portions with at least one intervening RNA portion, the 3'-DNA portion can be at least about any of 1, 3, 5, 7, 10 nucleotides, with an upper limit of about any of 10, 12, 15, 18, 20, 22 nucleotides. In one embodiment, the composite primer has a 3'-DNA portion of about 7 nucleotides.

The length of a non-3'-DNA portion (i.e., any DNA portion other than the 3'-DNA portion) in a composite primer comprising a 3'-DNA portion and at least one intervening RNA portion can be preferably from about 1 to about 10 nucleotides, more preferably from about 2 to about 8 nucleotides, and most preferably from about 3 to about 6 nucleotides. In some embodiments of a composite primer comprising a 3'-DNA portion and at least one intervening RNA portion, a non-3'-DNA portion can be at least about any of 1, 3, 5, 7, 10 nucleotides, with an upper limit of about any of 6, 8, 10, 12 nucleotides. The length of the 3'-DNA portion in a composite primer comprising a 3'-DNA portion and at least one intervening RNA portion can be preferably from about 1 to about 20 nucleotides, more preferably from about 3 to about 18 nucleotides, even more preferably from about 5 to about 15 nucleotides, and most preferably from about 7 to about 12 nucleotides. In some embodiments of a composite primer comprising a 3'-DNA portion and at least one intervening RNA portion, the 3'-DNA portion can be at least about any of 1, 3, 5, 7, 10 nucleotides, with an upper limit of about any of 10, 12, 15, 18, 20, 22 nucleotides. In one embodiment, the composite primer has a 3'-DNA portion of about 7 nucleotides. It is understood that the lengths for the various portions can be greater or less, as appropriate under the reaction conditions of the methods of this invention.

In some embodiments, the 5'-DNA portion of a composite primer includes the 5'-most nucleotide of the primer. In some embodiments, the 5'-RNA portion of a composite primer includes the 5' most nucleotide of the primer. In other embodiments, the 3'-DNA portion of a composite primer includes the 3' most nucleotide of the primer. In other embodiments, the 3'-DNA portion is adjacent to the 5'-RNA portion and includes the 3' most nucleotide of the primer (and the 5'-RNA portion includes the 5' most nucleotide of the primer). The total length of the composite primer can be preferably from about 10 to about 50 nucleotides, more preferably from about 15 to about 30 nucleotides, and most preferably from about 20 to about 25 nucleotides. In some embodiments, the length can be at least about any of 10, 15, 20, 25 nucleotides, with an upper limit of about any of 25, 30, 50, 60 nucleotides. In certain embodiments, the composite primer is about 21 or about 27 nucleotides in length. It is understood that the length can be greater or less, as appropriate under the reaction conditions of the methods of this invention.

As described herein, one or more different composite primers may be used in an amplification reaction.

DNA Polymerase, and an Agent Capable of Cleaving an RNA-DNA Hybrid

The amplification methods of the invention often employ the following enzymes: an RNA-dependent DNA polymerase, a DNA-dependent DNA polymerase, and an agent capable of cleaving an RNA strand of an RNA-DNA hybrid (for example, a ribonuclease such as RNase H). One or more of these activities may be found and used in a single enzyme.

For example, RNase H activity may be supplied by an RNA-dependent DNA polymerase (such as reverse transcriptase) or may be provided in a separate enzyme. Reverse transcriptases useful for this method may or may not have RNase H activity.

Many reverse transcriptases, such as those from avian myeloblastosis virus (AMV-RT), and Moloney murine leukemia virus (MMLV-RT) comprise more than one activity (for example, polymerase activity and ribonuclease activity) and can function in the formation of the double stranded cDNA molecules. However, in some instances, it is preferable to employ a reverse transcriptase which lacks the RNase H activity. Reverse transcriptase devoid of RNase H activity are known in the art, including those comprising a mutation of the wild type reverse transcriptase where the mutation eliminates the RNase H activity. In these cases, the addition of an RNase H from other sources, such as that isolated from E. coli, can be employed for the formation of the double stranded cDNA. The RNA-dependent DNA polymerase activity and DNA-dependent DNA polymerase activity may be provided by the same enzyme (for example, Bst polymerase), or these activities may be provided in separate enzymes.

Often, amplification methods of the invention involve formation of a complex comprising an RNA/DNA partial heteroduplex. This process generally utilizes the enzymatic activities of an RNA-dependent DNA polymerase and a DNA-dependent DNA polymerase. Generally, RNA in the RNA/DNA partial heteroduplex is cleaved by an agent (such as an enzyme, such as a ribonuclease) capable of cleaving RNA from an RNA/DNA hybrid, generating a 3' single stranded portion with sequences that are complementary to RNA in a composite primer (and thus forming a binding site for a composite primer).

RNA-dependent DNA polymerases for use in the methods and compositions of the invention are capable of effecting extension of a primer according to the methods of the invention. Accordingly, a preferred RNA-dependent DNA polymerase is one that is capable of extending a nucleic acid primer along a nucleic acid template that is comprised at least predominantly of ribonucleotides. Suitable RNA-dependent DNA polymerases for use in the methods and compositions of the invention include reverse transcriptase and, for example, a DNA polymerase that possesses both DNA-dependent and RNA-dependent DNA polymerase activity, such as Bst DNA polymerase.

DNA-dependent DNA polymerases for use in the methods and compositions of the invention are capable of effecting extension of the composite primer according to the methods of the invention. Accordingly, a preferred polymerase is one that is capable of extending a nucleic acid primer along a nucleic acid template that is comprised at least predominantly of deoxyribonucleotides. The formation of the complex comprising the RNA/DNA partial heteroduplex can be carried out by a DNA polymerase which comprises both RNA-dependent DNA polymerase and DNA-dependent DNA polymerase activities (such as Bst DNA polymerase, or a reverse transcriptase). Amplification of an RNA sequence according to methods of the invention involves the use of a DNA polymerase that is able to displace a nucleic acid strand from the polynucleotide to which the displaced strand is bound, and, generally, the more strand displacement capability the polymerase exhibits (i.e., compared to other polymerases which do not have as much strand displacement capability) is preferable. Preferably, the DNA polymerase has high affinity for binding at the 3'-end of an oligonucleotide hybridized to a nucleic acid strand. Preferably, the DNA polymerase does not possess substantial nicking activity. Generally, the DNA polymerase preferably has little or no 5'→3' exonuclease activity so as to minimize degradation of primer, or primer extension polynucleotides. Generally, this exonuclease activity is dependent on factors such as pH, salt concentration, whether the template is double stranded or single stranded, and so forth, all of which are familiar to one skilled in the art. Mutant DNA polymerases in which the 5'→3' exonuclease activity has been deleted, are known in the art and are suitable for the amplification methods described herein. Mutant DNA polymerases which lack both 5' to 3' nuclease and 3' to 5' nuclease activities have also been described, for example, exo$^{-/-}$ 1 (lenow DNA polymerase. It is preferred that the DNA polymerase displaces primer extension products from the template nucleic acid in at least about 25%, more preferably at least about 50%, even more preferably at least about 75%, and most preferably at least about 90%, of the incidence of contact between the polymerase and the 5' end of the primer extension product. In some embodiments, the use of thermostable DNA polymerases with strand displacement activity is preferred. Such polymerases are known in the art, such as described in U.S. Pat. No. 5,744,312 (and references cited therein). Preferably, the DNA polymerase has little to no proofreading activity.

Suitable DNA polymerases for use in the methods and compositions of the invention include those disclosed in U.S. Pat. Nos. 5,648,211 and 5,744,312, which include exo Vent (New England Biolabs), exo$^-$ Deep Vent (New England Biolabs), Bst (BioRad), exo Pfu (Stratagene), Bca (Panvera), sequencing grade Taq (Promega), exo$^{4-}$ Klenow DNA polymerase, and thermostable DNA polymerases from thermoanaerobacter thermohydrosulfuricus.

In some embodiments, the agent that is capable of cleaving RNA in an RNA/DNA hybrid for use in the methods and compositions of the invention is a ribonuclease that is capable of cleaving ribonucleotides in an RNA/DNA hybrid but is not capable of cleaving single-stranded RNA. Preferably, the ribonuclease cleaves ribonucleotides in an RNA/DNA hybrid regardless of the identity and type of nucleotides adjacent to the ribonucleotide to be cleaved. It is preferred that the ribonuclease cleaves independent of sequence identity. Examples of suitable ribonucleases for the methods and compositions of the invention are well known in the art, including ribonuclease H(RNase H), e.g., Hybridase.

As is well known in the art, DNA-dependent DNA polymerase activity, RNA-dependent DNA polymerase activity, and the ability to cleave RNA from a RNA/DNA hybrid may be present in different enzymes, or two or more activities may be present in the same enzyme. Accordingly, in some embodiments, the same enzyme comprises RNA-dependent DNA polymerase activity and cleaves RNA from an RNA/DNA hybrid. In some embodiments, the same enzyme comprises DNA-dependent DNA polymerase activity and cleaves RNA from an RNA/DNA hybrid. In some embodiments, the same enzyme comprises DNA-dependent DNA polymerase activity, RNA-dependent DNA polymerase activity and cleaves RNA from an RNA/DNA hybrid. In some embodiments, different enzymes comprise RNA-dependent DNA polymerase activity and DNA-dependent DNA polymerase activity. In some embodiments, different enzymes comprise RNA-dependent DNA polymerase activity and cleave RNA from an RNA/DNA hybrid. In some embodiments, different enzymes comprise DNA-dependent DNA polymerase activity and cleave RNA from an RNA/DNA hybrid.

Enzyme Capable of Cleaving Single-Stranded RNA

Methods of the invention employ an enzyme capable of cleaving single-stranded RNA. The enzyme may be used to cleave RNA in a first primer prior to addition of a second primer containing single-stranded RNA to a reaction mixture and/or to cleave single-stranded RNA from amplification products as described herein. In embodiments in which the enzyme is used to cleave single stranded RNA of a first composite primer, the enzyme capable of cleaving single-stranded RNA is generally added in an amount that is sufficient to degrade all or substantially all of the single-stranded RNA in the first RNA-containing primer.

RNase enzymes have been previously described in procedures for detecting mutations (Grange et al. (1990) *Nucleic Acids Res.* 18(14):4227-36; Goldrick (2001) *Hum Mutat.* 18(3):190-204; Murthy et al. (1995) *DNA Cell Biol.* 14(1): 87-94; U.S. Pat. No. 4,946,773), degradation of excess mRNA to enrich cDNA/mRNA hybrid after first strand cDNA synthesis (Carninci et al. (1999) *Methods Enzymol.* 303:19; PCT Application No. WO 98/20122), and for prevention of cross contamination in a PCR amplification reaction (Walder et al. (1993) *Nucleic Acids Res.* 21(18):4339-43, for the preparation of full length cDNA libraries (Carninci et al. (2000) *Genome Res.* 10(10):1617-30.

RNase I works well in the methods of the invention as described herein, since it has little or no sequence specificity, and is known to cleave the bond between any combination of ribo-nucleotides in a single-stranded RNA. RNase T may also be used although it is known to exhibit sequence specificity. Combinations of RNase enzymes may also be used. An important aspect in choosing a single-stranded RNA specific RNase enzyme suitable for use in the methods of the invention is the ability to easily inactivate the RNase activity prior to addition of a second RNA-containing primer, so as not to compromise the integrity of the RNA in the second primer, for example a DNA/RNA amplification primer. RNase I is easily inactivated at elevated temperature. In addition, RNase I is known to be insensitive to ion composition of the reaction mixture, and thus its use in the methods of the invention generally do not require buffer modification or exchange (i.e., to change to a buffer composition suitable for the cleavage of the RNA portion of the first strand RNA-containing primer).

RNase I may be inactivated by elevation of the temperature of the reaction mixture, for example, to 70° C. to 90° C. for 5 to 20 minutes.

RNase I may be used at a concentration of about 0.01 to about 0.11 units per In some embodiments, RNase I is used at a concentration of any of about 0.01, 0.02, 0.03, 0.04, 0.05, 0.06, 0.07, 0.08, 0.09, 0.10, or 0.11 units per 0. The reaction is usually carried out at 37° C. for about 30 minutes. Reaction buffer commonly comprises 10 mM Tris-HCl, pH 7.5, 100 mM NaCl. The enzyme is active at a wide range of concentration of divalent ions such as MgCl in the range of 0 to 6 mM or higher.

Reaction Conditions and Detection

Appropriate reaction media and conditions for carrying out the methods of the invention are those that permit nucleic acid amplification according to the methods of the invention. Such media and conditions are known to persons of skill in the art, and are described in various publications, such as U.S. Pat. Nos. 5,554,516; 5,716,785; 5,130,238; 5,194,370; 6,090,591; 5,409,818; 5,554,517; 5,169,766; 5,480,784; 5,399,491; 5,679,512; and PCT Pub. No. W099/42618. For example, a buffer may be Tris buffer, although other buffers can also be used as long as the buffer components are non-inhibitory to enzyme components of the methods of the invention. The pH is preferably from about 5 to about 11, more preferably from about 6 to about 10, even more preferably from about 7 to about 9, and most preferably from about 7.5 to about 8.5. The reaction medium can also include bivalent metal ions such as $Mg^{2+}$ or $Mn^{24-}$, at a final concentration of free ions that is within the range of from about 0.01 to about 15 mM, and most preferably from about 1 to 10 mM.

The reaction medium can also include other salts, such as KCl or NaCl, that contribute to the total ionic strength of the medium. For example, the range of a salt such as KCl is preferably from about 0 to about 125 mM, more preferably from about 0 to about 100 mM, and most preferably from about 0 to about 75 mM. The reaction medium can further include additives that could affect performance of the amplification reactions, but that are not integral to the activity of the enzyme components of the methods. Such additives include proteins such as BSA or acetylated BSA, single strand binding proteins (for e.g., T4 gene 32 protein), and non-ionic detergents such as NP40 or TRITON™. Reagents, such as DTT, that are capable of maintaining enzyme activities can also be included. Such reagents are known in the art. Where appropriate, an RNase inhibitor (such as Rnasin) that does not inhibit the activity of the RNase employed in the method can also be included. Any aspect of the methods of the invention can occur at the same or varying temperatures. Preferably, the amplification reactions (particularly, primer extension other than the composite and second primer extension product synthesis steps, and strand displacement) are performed isothermally, which avoids the cumbersome thermocycling process. The amplification reaction is carried out at a temperature that permits hybridization of the oligonucleotides (primer) of the invention to the template polynucleotide and primer extension products, and that does not substantially inhibit the activity of the enzymes employed. The temperature can be in the range of 0° C. to about 85° C., about 25° C. to about 85° C., about 30° C. to about 80° C., and about 37° C. to about 75° C.

Random priming and/or primer extension and/or isothermal amplification can be conducted under conditions of reduced stringency (i.e., permitting hybridization of sequences that are not fully complementary). For a given set of reaction conditions, the ability of two nucleotide sequences to hybridize with each other is based on the degree of complementarity of the two nucleotide sequences, which in turn is based on the fraction of matched complementary nucleotide pairs. The more nucleotides in a given sequence that are complementary to another sequence, the more stringent the conditions can be for hybridization and the more specific will be the binding of the two sequences. Conversely, the lower the stringency of the conditions for hybridization, the lower the complementarity necessary for binding between the hybridizing and/or partially hybridizing composite primer and template polynucleotide. Decreased stringency is achieved by any one or more of the following: reducing the temperature, decreasing the ratio of co-solvents, lowering the salt concentration, and the like. Conditions that increase or reduce the stringency of a hybridization reaction are widely known and published in the art. See, for example, Sambrook et al. (1989), and in Ausubel (1987), supra. Useful hybridization conditions are also provided in, e.g., Tijessen, 1993, Hybridization With Nucleic Acid Probes, Elsevier Science Publishers B. V. and Kricka, 1992, Nonisotopic DNA Probe Techniques, Academic Press San Diego, Calif. The hybridization conditions chosen depend on a variety of factors known in the art, for example the length and type (e.g., RNA, DNA, PNA) of primer and primer binding region of the oligonucleotide template, as well as the concentration of primer and template polynucleotides.

Insofar as it is convenient to use buffer conditions that are compatible with DNA polymerase activity and/or ribonuclease activity, stringency of hybridization of composite primers can be controlled by altering temperature of the reaction. Examples of relevant conditions include (in order of increasing stringency): incubation temperatures of approximately 15° C., 20° C., 25° C., 30° C., 37° C., 40° C., 45° C., 50° C., 60° C., or more. Accordingly, in some embodiments, composite primer random hybridization occurs at a reduced temperature, for example at 25° C.-37° C., followed at incubation at increased temperature(s) suitable for the amplification phase of the methods (such as about 50° C.). In some embodiments, temperature is increased at 5° C. increments. In other embodiments, temperature is shifted from low to high temperature.

Nucleotide and/or nucleotide analogs, such as deoxyribonucleoside triphosphates, that can be employed for synthesis of the primer extension products in the methods of the invention are provided in the amount of from preferably about 50 to about 2500 µM, more preferably about 100 to about 20001.1 M, even more preferably about 200 to about 1700 JIM, and most preferably about 250 to about 1500 µM. In some embodiments, a nucleotide or nucleotide analog whose presence in the primer extension strand enhances displacement of the strand (for example, by causing base pairing that is weaker than conventional AT, CG base pairing) is included. Such nucleotide or nucleotide analogs include deoxyinosine and other modified bases, all of which are known in the art.

The oligonucleotide components of the amplification reactions of the invention are generally in excess of the number of target nucleic acid sequence to be amplified. They can be provided at about or at least about any of the following: 10, $10^2$, $10^4$, $10^6$, $10^8$, $10^{10}$, $10^{12}$ times the amount of target nucleic acid. Composite primers can each be provided at about or at least about any of the following concentrations: 50 nM, 100 nM, 500 nM, 1 uM, 2.5 uM, 5 uM, 10 uM. Composite primer concentration also impacts frequency and/or position of composite primer hybridization. Generally, increased primer concentrations increased frequency of primer hybridization. Auxiliary primers can be provided at about or at least about any of the following concentrations: about 25 nM, about 50 nM, about 100 nM, about 500 nM, about 1 uM, about 2.5 uM, about 5 uM, about 10 uM, or more.

In one embodiment, the foregoing components are added simultaneously at the initiation of the amplification process. In another embodiment, components are added in any order prior to or after appropriate timepoints during the amplification process, as required and/or permitted by the amplification reaction. Such timepoints, some of which are noted below, can be readily identified by a person of skill in the art. The enzymes used for nucleic acid amplification according to the methods of the invention can be added to the reaction mixture either prior to the target nucleic acid denaturation step, following the denaturation step, or following hybridization of the primer to the target polynucleotide, as determined by their thermal stability and/or other considerations known to the person of skill in the art. In these embodiments, the reaction conditions and components may be varied between the different reactions.

The amplification process can be stopped at various timepoints, and resumed at a later time. Said timepoints can be readily identified by a person of skill in the art. One timepoint is at the end of random composite primer hybridization. Another timepoint is at the end of random composite primer hybridization and composite primer extension product synthesis. Another timepoint (in some embodiments) is following cleavage of template RNA. Another timepoint is following cleavage of excess first RNA-containing primer with an enzyme capable of cleaving single-stranded RNA, such as RNase I. Another timepoint is immediately prior to initiation of single primer amplification (which in some embodiments, may be initiated by addition of an enzyme (such as RNase H) that cleaves RNA from RNA/DNA heteroduplex, and optionally, DNA polymerase). Another timepoint is at the end of second primer extension product synthesis. Methods for stopping the reactions are known in the art, including, for example, cooling the reaction mixture to a temperature that inhibits enzyme activity or heating the reaction mixture to a temperature that destroys an enzyme. Methods for resuming the reactions are also known in the art, including, for example, raising the temperature of the reaction mixture to a temperature that permits enzyme activity, replenishing a destroyed (depleted) enzyme, or adding reagent(s) necessary for initiation of a step (for example, addition of RNase H and/or DNA polymerase to initiate the single primer amplification phase of the methods). In some embodiments, one or more of the components of the reactions is replenished prior to, at, or following the resumption of the reactions. For example, it may be necessary to replenish the composite primer prior to beginning the single primer amplification reaction if the same composite primer is being used. Alternatively, the reaction can be allowed to proceed (i.e., from start to finish) without interruption.

The reaction can be allowed to proceed without purification of intermediate complexes, for example, to remove primer. Products can be purified at various timepoints, which can be readily identified by a person of skill in the art. One timepoint is at the end of formation of the complex comprising an RNA/DNA partial heteroduplex. Another timepoint is at the end of composite primer hybridization.

The detection of the amplification product is indicative of the presence of the target sequence. Quantitative analysis is also feasible. Direct and indirect detection methods (including quantitation) are well known in the art. For example, by comparing the amount of product amplified from a test sample containing an unknown amount of a polynucleotide containing a target sequence to the product of amplification of a reference sample that has a known quantity of a polynucleotide that contains the target sequence, the amount of target sequence in the test sample can be determined.

Compositions and Kits of the Invention

The invention also provides compositions and kits used in the methods described herein. The compositions may be any component(s), reaction mixture and/or intermediate described herein, as well as any combination.

In one embodiment, the invention provides an enzyme capable of cleaving single-stranded RNA and one or more of a composite primer comprising an RNA portion and a 3'-DNA portion; a DNA-dependent and/or RNA-dependent polymerase; an enzyme that cleaves RNA from an RNA/DNA duplex; and auxiliary primers (for example, a population of random hexamer primers).

In some embodiments, the composition comprises a composite primer comprising 5'- and 3'-DNA portions with at least one intervening RNA portion. In other examples, the invention provides a composition comprising a composite primer as described herein, and auxiliary primers (for example, a population of randomized hexamer primers). In other examples, the composition comprises a composite primer that is derivatized by attachment of a moiety capable of effecting attachment of a polynucleotide comprising the composite primer to a solid substrate used in preparing nucleic acid microarrays. In some embodiments, the composite primer is further by attachment of a positively charged moiety such as an amine. In other embodiments, the composite primer is labeled, for example by derivatizing the composite primer with a detectable moiety, such as a label, or a moiety that can be covalently or non-covalently attached to a label. Labeled composite primers are further described herein.

In some embodiments, the composition further comprises a labeled dNTP, labeled rNTP and/or a nucleotide terminator, e.g., a labeled nucleotide terminator.

In still other embodiments, the composition comprises a non-canonical nucleotide (such as dUTP), and reagents suitable for labeling and/or fragmenting abasic sites, as described in co-pending U.S. Patent Application Publication Nos. 2004/0005614 and 2005/0208538, and U.S. provisional patent application No. 60/817,890. In methods of the invention in which amplification is performed in the presence of one or more non-canonical nucleotides, the amplified products may be contacted with an enzyme such as a glycosylase to cleave the base portion of the non-canonical nucleotide to generate an abasic site. The polynucleotides containing abasic sites may be contacted with an agent that cleaves polynucleotides at abasic sites to generate polynucleotide fragments. The polynucleotide fragments may be labeled at or near the abasic site.

In some embodiments, the compositions further comprise amplification products produced as described herein. Accordingly, the invention provides compositions comprising a population of polynucleotides which are copies or the complement of a target sequence, which are produced by any of the methods described herein (or compositions comprising the products). The invention also includes compositions and various configurations (such as arrays) of these populations, which may be homogeneous (same sequence) or heterogeneous (different sequence). These populations may be any assembly of sequences obtained from the methods described herein.

The compositions are generally in lyophilized or aqueous form, preferably in a suitable buffer.

The compositions are generally in a suitable medium, although they can be in lyophilized form. Suitable media include, but are not limited to, aqueous media (such as pure water or buffers).

The invention provides kits for carrying out the methods of the invention. Accordingly, a variety of kits are provided in suitable packaging. The kits may be used for any one or more of the uses described herein, and, accordingly, may contain instructions for any one or more of the following uses: methods of amplification; genotyping, nucleic acid mutation detection (including methods of genotyping), determining the presence or absence of a sequence of interest, quantitating a sequence of interest, preparation of an immobilized nucleic acid (which can be a nucleic acid immobilized on a microarray), comparative genomic hybridization, and characterizing nucleic acids using the amplified nucleic acid products generated by the methods of the invention, methods of expression profiling, subtractive hybridization and the preparation of probes for subtractive hybridization, and methods of preparing libraries (which may be cDNA and/or differential hybridization libraries).

The kits of the invention comprise one or more containers comprising an enzyme capable of cleaving single-stranded RNA, such as RNase I, RNase T, RNase A, or a combination thereof) and any combination of the components described herein. A kit may comprise any of the composite primers described herein. In some embodiments, a kit further comprises auxiliary primers, which may or may not be separately packaged. The composite primer may be labeled or unlabeled. Kits may also optionally further include any of one or more of the enzymes described herein (for example, DNA-dependent DNA polymerase, RNA-dependent DNA polymerase, a DNA polymerase that provides both DNA-dependent and RNA-dependent DNA polymerase activities, an enzyme capable of cleaving RNA from an RNA/DNA hybrid, such as RNase H, as well as deoxynucleoside triphosphates (labeled or unlabeled or derivatized). Kits may also include one or more suitable buffers (for example, as described herein). Kits may also include a labeled dNTP(s) and/or a non-canonical nucleotide (such as dUTP), as described in Kurn et al, co-pending U.S. patent application No. 2004-0005614.

One or more reagents in the kit can be provided as a dry powder, usually lyophilized, including excipients, which on dissolution will provide for a reagent solution having the appropriate concentrations for performing any of the methods described herein. Each component can be packaged in separate containers or some components can be combined in one container where cross-reactivity and shelf life permit.

The kits of the invention may optionally include a set of instructions, generally written instructions, although electronic storage media (e.g., magnetic diskette or optical disk) and/or reference to a website containing instructions are also acceptable, relating to the use of components of the methods of the invention for the intended nucleic acid amplification, and/or, as appropriate, for using the amplification products for purposes such as detection of sequence mutation. The instructions included with the kit generally include information as to reagents (whether included or not in the kit) necessary for practicing the methods of the invention, instructions on how to use the kit, and/or appropriate reaction conditions.

In another example, any of these kits further comprises one or more controls (which can be, for example, template polynucleotide (e.g., DNA template such as genomic DNA or RNA template such as total RNA or mRNA), composite primers, and/or auxiliary primer(s).

The component(s) of the kit may be packaged in any convenient, appropriate packaging. The components may be packaged separately, or in one or multiple combinations.

The relative amounts of the various components in the kits can be varied widely to provide for concentrations of the reagents that substantially optimize the reactions that need to occur to practice the methods disclosed herein and/or to further optimize the sensitivity of any assay.

The invention also provides systems for effecting the methods described herein. These systems comprise an enzyme capable of cleaving single-stranded RNA and various combinations of the components discussed above.

Any of the systems embodiments may also comprise a template (target) sequence, as described herein. A system generally includes one or more apparatuses for performing the amplification methods of the invention. Such apparatuses include, for example, heating devices (such as heating blocks or water baths) and apparatuses which effect automation of one or more steps of the methods described herein. The methods of the invention are particularly suitable for use with miniaturized devices, as thermal cycling is not required for any of the steps. A non-limiting example of suitable devices includes the BioAnalyzer (Agilent and Caliper) and the eSensor.

The invention also provides reaction mixtures (or compositions comprising reaction mixtures) which contain an enzyme capable of cleaving single-stranded RNA and various combinations of components described herein. Examples of reaction mixtures have been described. In some embodiments, the invention provides reaction mixtures comprising (a) a target polynucleotide; (b) a composite primer comprising a 3' DNA portion and an RNA portion; (c) a polymerase; and (d) an enzyme capable of cleaving single-stranded RNA, such as RNase I. As described herein, any of the composite primers may be in the reaction mixture (or a plurality of composite primers), including a composite primer that comprises a 5' RNA portion which is adjacent to the 3' DNA portion. The reaction mixture could also further comprise an enzyme which cleaves RNA from an RNA/DNA hybrid, such as RNase H.

Other reaction mixtures are described herein and are encompassed by the invention.

Figure 3A:
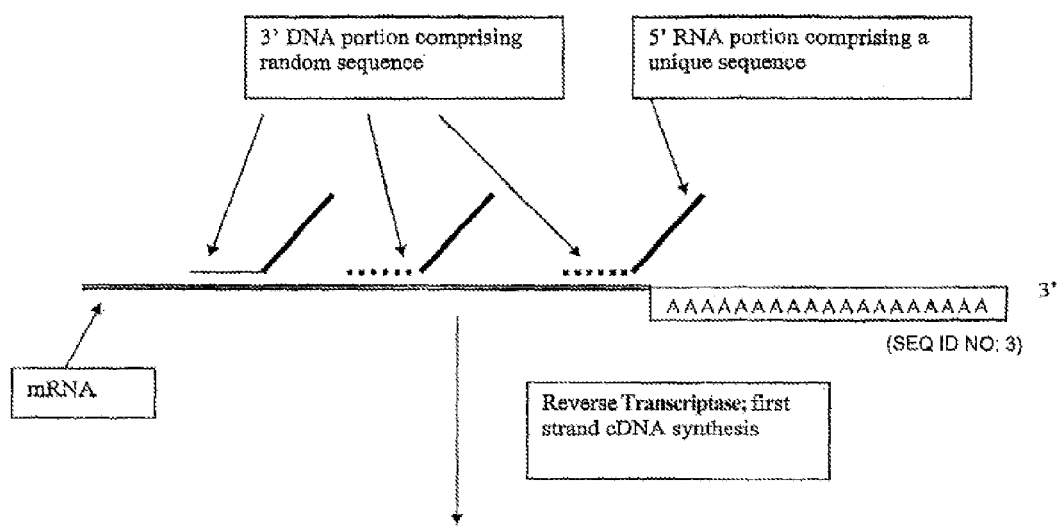
FIG. 3A: Hybridization of a plurality of first chimeric primers comprising a 3' DNA portion with a random sequence to an mRNA target.
Figure 3D:
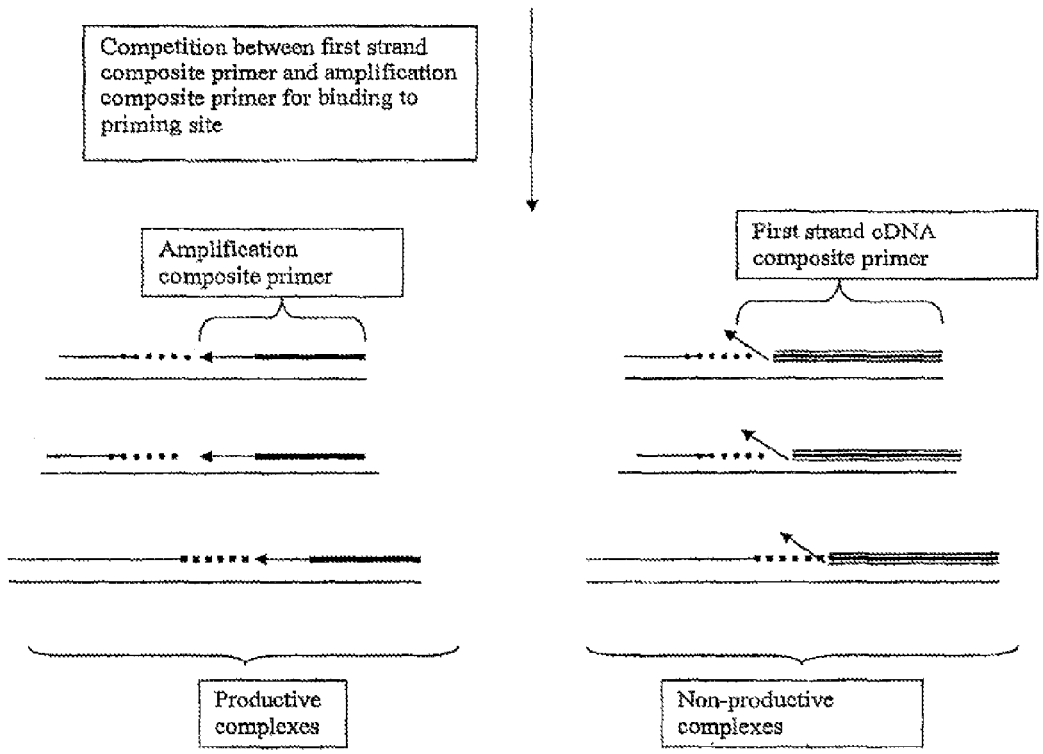
FIG. 3D: Amplification without prior incubation with enzyme capable of degrading single-stranded RNA.
Figure 3E:
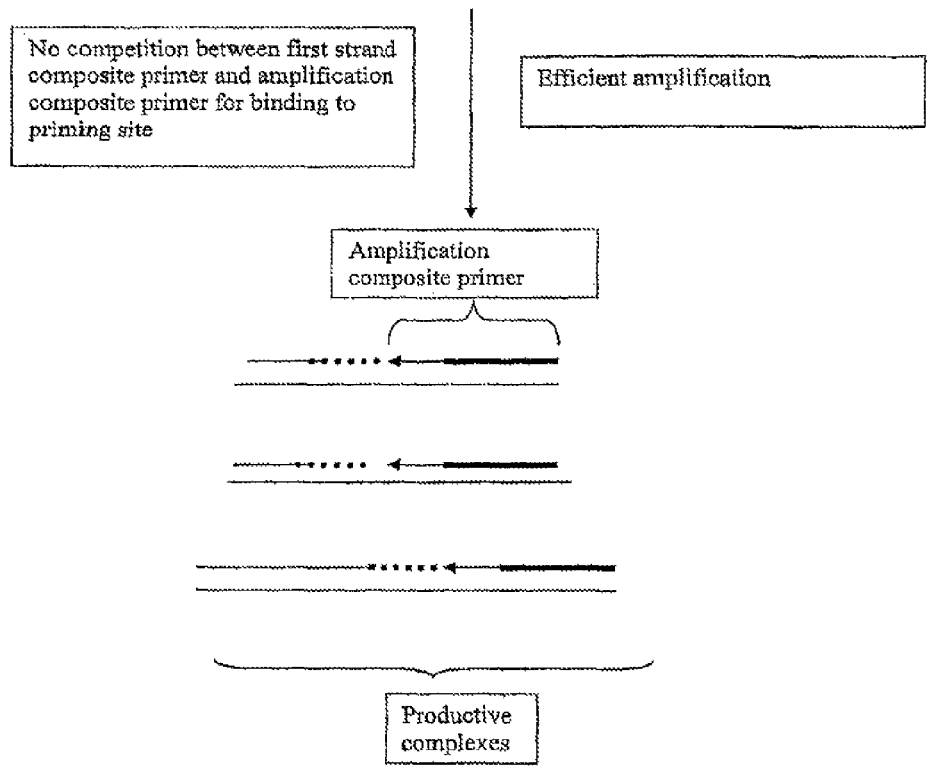
FIG. 3E: Amplification following treatment with RNase I to degrade excess first composite primers.

The invention also includes compositions comprising any of the complexes (which are intermediates in the methods described herein) described herein. Examples of such complexes are schematically depicted in FIGS. 1-3. As an example, one complex of the invention is a complex comprising: (a) a target polynucleotide strand; and (b) a composite primer, said composite primer comprising a 3' DNA portion and an RNA portion. The composite primer may have an RNA portion which is 5' and adjacent to the 3' DNA portion. As another example, a complex of the invention is a complex comprising: (a) a composite primer extension product; and (b) a target polynucleotide.

In yet another example, a complex of the invention is a complex comprising a RNA/DNA partial heteroduplex, prepared by any of the methods described herein. In some embodiments, the complex further comprises a second RNA/DNA partial heteroduplex at a second end. In yet another example, the complex of the invention is a complex comprising a 3' single stranded DNA portion produced by any of the methods described herein. In some embodiments, the complex further comprises a second 3' single stranded region. In another example, the complex of the invention is (a) a complex comprising a 3' single stranded DNA portion, and (b) a composite primer hybridized to the 3' single stranded portion.

The following Example is intended to illustrate, but not limit, the invention.

EXAMPLE

An RNA target is amplified using a method involving two chimeric RNA/DNA primers with degradation of the RNA portion of the first chimeric primer prior to addition of the second chimeric primer for improved amplification efficiency as described below.

First Strand cDNA Synthesis

First stand cDNA synthesis is initiated randomly across the length of RNA transcripts using chimeric primers having a 3'-DNA portion that includes a random, for example, a random hexamer sequence, and a 5'-RNA portion that includes a sequence that is not complementary to the target RNA. 1 to 2 pl of total RNA sample (0.5 to 5Ong total RNA purified from a sample to be analyzed), is mixed with 1 to 2 pl chimeric first strand cDNA primer mixture (5 to 40 uM final concentration), and the mixture was transferred to a heating block or a thermal cycler, and incubated at 50° C. to 65° C. for 5 minutes, for denaturation. The mixture is removed from the heating block or thermocycler and placed on ice.

A mixture of reverse transcriptase and a buffer containing Mg, salt, RNase inhibitor (Rnasin or any other commercially available RNase inhibitor commonly used for cDNA synthesis) and all four dNTPs, in volume of up to 10111, is added to the chimeric primer mixture and the reaction is incubated at 25° C. (range of 16 to 30° C.) for 10 minutes (range of 5 to 20 minutes), followed by incubation at 42° C. (range 37° C. to 48° C.) for 15 minutes (range 5 to 60 minutes), and a short incubation at 65° C. for 2 to 5 minutes for inactivation of the reverse transcriptase and nicking of the RNA in the newly synthesized RNA-cDNA heteroduplex, as previously described (see, for example, U.S. Patent Application No. 2003/0087251). The reaction mixture is placed on ice.

Second Strand Synthesis

A mixture of DNA polymerase (Klenow exo-, Bst large fragment, BCA or any other polymerase suitable for second strand cDNA synthesis) in a suitable buffer containing a suitable ion composition for activity of the polymerase used, RNase inhibitor (Rnasin or any other commercially available RNase inhibitor commonly used for cDNA synthesis), and all four dNTPs is added to the first strand synthesis reaction mixture (to a total volume of 10 to 201.11). The reaction mixture is incubated at 25° C. for 5 to 10 minutes followed by incubation at a temperature appropriate for the DNA polymerase used (37° C. to 50° C.) for 30 to 60 minutes. At the end of this second strand cDNA synthesis step, the reaction mixture is incubated at 75° C. (65 to 85° C.) for 5 to 15 minutes for inactivation of the polymerase and RNase inhibitor (Rnasin). The inactivation of the RNase inhibitor prior to progressing to the next step is particularly important when using an RNase which is known to be inhibited by the inhibitor used in this step of the reaction.

Degradation of the RNA Portion of the First Strand cDNA Chimeric Primers by Treatment with Single-Strand Specific RNase The degradation of the 5'-RNA portion of the chimeric first strand cDNA primers which have not been incorporated into the double stranded cDNA to form an RNA/DNA heteroduplex at one end of the double-stranded cDNA products can be carried out with an enzyme that is capable of degrading single-stranded RNA, for example, RNase I.

Cleavage of single-stranded RNA is initiated by the addition of RNase Ito the second strand cDNA reaction mixture (following the heat inactivation step at the end of the second strand cDNA synthesis reaction) and incubation of the reaction mixture at 37° C. for 15 minutes (10 to 30 minutes range). For convenience and accuracy of pipetting, the stock RNase I (which is usually supplied in storage buffer comprising 50% glycerol) can be diluted with the buffer used in the second strand cDNA synthesis step. 1 to 51.11 of the diluted mixture is added to the reaction mixture for a final concentration of 0.01 to 0.11 Units per pl reaction volume. The enzyme is inactivated by incubation of the reaction mixture at elevated temperature (70° C. to 90° C.) for 5 to 20 minutes.

Amplification

Amplification is carried out according to the previously described method for RNA amplification using chimeric primers, for example, as described in U.S. Patent Application Nos. 2003/0087251 or 2004/0005614, or at www.nugeninc.com. An example of amplification reaction conditions is as follows:

5 pl of the second strand cDNA reaction mixture is mixed with 20 i_tl reaction mixture containing:

2 pl of 1 ox buffer (200 mM Tris-HCl, pH 8.5, 50 mM MgCl2, 1% NP-40)

0.2 pl of dATP, dGTP, dCTP and dTTP (25 mM) 0.2 pl of amplification chimeric primer (100 p.M)

5 pl of amplification enzyme mixture comprising DNA polymerase, RNase H, T4 Gene 32 protein and Rnasin. DEPC-treated water to a total volume of 20 µl.

The reaction is carried out at 50° C. for 60 minutes, and amplification is stopped by heating at 80° C. for 5 minutes.

Although the foregoing invention has been described in some detail by way of illustration and examples for purposes of clarity of understanding, it will be apparent to those skilled in the art that certain changes and modifications may be practiced without departing from the spirit and scope of the invention. Therefore, the description should not be construed as limiting the scope of the invention.

All publications, patents and patent applications cited herein are hereby incorporated by reference in their entirety for all purposes to the same extent as if each individual publication, patent or patent application were specifically and individually indicated to be so incorporated by reference.

whereby multiple copies of a primer extension product comprising sequence complementary to the target sequence are produced; and (c) incubating the multiple copies of the primer extension product comprising sequence complementary to the target sequence with an enzyme that is capable of cleaving single-stranded RNA, wherein residual single-stranded

We claim:

1. A method for amplifying a polynucleotide sequence complementary to a target polynucleotide sequence, comprising:

(a) extending a composite amplification primer in a complex comprising (i) a polynucleotide template comprising the target sequence, wherein the polynucleotide template comprising the target sequence is DNA; and (ii) the composite amplification primer, wherein the composite amplification primer comprises an RNA portion and a 3' DNA portion, wherein the composite amplification primer is hybridized to the polynucleotide template;

(b) cleaving the RNA portion of the annealed composite amplification primer with an enzyme that cleaves RNA from an RNA/DNA hybrid such that another composite amplification primer hybridizes to the template and repeats primer extension and strand displacement, RNA from the composite amplification primer in the primer extension product comprising sequence complementary to the target sequence is cleaved.

2. A method of generating multiple copies of a polynucleotide sequence complementary to an RNA sequence of interest, the method comprising:

(a) extending a composite amplification primer in a complex comprising:

(i) a complex of first and second primer extension products, wherein the first primer extension product is produced by extension of a first primer hybridized to a target RNA with at least one enzyme comprising RNA-dependent DNA polymerase activity, wherein the first primer is a composite primer comprising an RNA portion and a 3' DNA portion, wherein the second primer extension product is generated by extension of a second primer hybridized to the first primer extension product, wherein the second primer is different from the first primer, and wherein RNA from the complex of first and second primer extension products is cleaved with at least one enzyme that cleaves RNA from an RNA/DNA hybrid; and (ii) a composite amplification primer, the composite amplification primer comprising an RNA portion and a 3' DNA portion, wherein the composite amplification primer is hybridized to the second primer extension product;

whereby the first primer extension product is displaced, RNA is cleaved from the composite amplification primer and another composite amplification primer hybridizes such that primer extension and strand displacement are repeated, whereby multiple copies of a primer extension product comprising polynucleotide sequence complementary to the RNA sequence of interest are generated; and (b) contacting the multiple copies of the primer extension product comprising sequence complementary to the RNA sequence of interest with an enzyme that is capable of cleaving single-stranded RNA, wherein residual single-stranded RNA from the composite primer in the primer extension product comprising sequence complementary to the RNA sequence of interest is cleaved.

3. The method of claim 1, wherein the enzyme capable of cleaving single-stranded RNA is RNase I.

4. The method of claim 2, wherein the enzyme capable of cleaving single-stranded RNA is RNase I.

5. The method of claim 1, wherein the first primer is hybridizable to a multiplicity of template polynucleotide sites.

6. The method of claim 2, wherein the first primer is hybridizable to a multiplicity of template polynucleotide sites.

7. The method of claim 1, wherein the RNA portion of the composite amplification primer is 5' with respect to the 3' DNA portion.

8. The method of claim 2, wherein the RNA portion of the composite amplification primer is 5' with respect to the 3' DNA portion.

9. The method of claim 1, wherein the at least one enzyme that cleaves RNA from a double-stranded RNA-DNA hybrid is RNase H.

10. The method of claim 2, wherein the at least one enzyme that cleaves RNA from a double-stranded RNA-DNA hybrid is RNase H.

* * * * *